(12) United States Patent
Accili et al.

(10) Patent No.: US 10,487,314 B2
(45) Date of Patent: Nov. 26, 2019

(54) INHIBITION OF SEROTONIN EXPRESSION IN GUT ENTEROENDOCRINE CELLS RESULTS IN CONVERSION TO INSULIN-POSITIVE CELLS

(71) Applicant: THE TRUSTEES OF COLUMBIA UNIVERSITY IN THE CITY OF NEW YORK, New York, NY (US)

(72) Inventors: Domenico Accili, New York, NY (US); Ryotaro Bouchi, Shinjuku-ku (JP)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/321,504

(22) PCT Filed: Jun. 26, 2015

(86) PCT No.: PCT/US2015/038186
§ 371 (c)(1),
(2) Date: Dec. 22, 2016

(87) PCT Pub. No.: WO2015/200901
PCT Pub. Date: Dec. 30, 2015

(65) Prior Publication Data
US 2017/0204375 A1    Jul. 20, 2017

Related U.S. Application Data

(60) Provisional application No. 62/017,405, filed on Jun. 26, 2014.

(51) Int. Cl.
*C12N 5/071* (2010.01)
*C12N 15/113* (2010.01)
*A61K 35/38* (2015.01)
*A61K 38/28* (2006.01)
*A61L 27/36* (2006.01)
*A61L 27/38* (2006.01)
*C07K 14/62* (2006.01)
*C07K 16/40* (2006.01)

(52) U.S. Cl.
CPC ............ *C12N 5/0679* (2013.01); *A61K 35/38* (2013.01); *A61K 38/28* (2013.01); *A61L 27/3687* (2013.01); *A61L 27/383* (2013.01); *A61L 27/3813* (2013.01); *A61L 27/3882* (2013.01); *C07K 14/62* (2013.01); *C07K 16/40* (2013.01); *C12N 15/113* (2013.01); *C12N 15/1137* (2013.01); *C12Y 114/16004* (2013.01); *C12Y 401/01028* (2013.01); *A61L 2430/22* (2013.01); *C12N 2310/11* (2013.01); *C12N 2310/12* (2013.01); *C12N 2310/14* (2013.01); *C12N 2310/531* (2013.01); *C12N 2506/23* (2013.01)

(58) Field of Classification Search
CPC .. A61K 35/38; C12N 15/113; C12N 2310/14; A01K 2207/05
See application file for complete search history.

(56) References Cited

U.S. PATENT DOCUMENTS

| | | |
|---|---|---|
| 4,426,330 A | 1/1984 | Sears |
| 4,522,811 A | 6/1985 | Epptein et al. |
| 4,534,899 A | 8/1985 | Sears |
| 4,946,778 A | 8/1990 | Ladner et al. |
| 4,987,071 A | 1/1991 | Cech et al. |
| 5,013,556 A | 5/1991 | Woodle et al. |
| 5,013,830 A | 5/1991 | Ohtsuka et al. |
| 5,108,921 A | 4/1992 | Low et al. |
| 5,116,742 A | 5/1992 | Cech et al. |
| 5,149,797 A | 9/1992 | Pederson et al. |
| 5,213,804 A | 5/1993 | Martin et al. |

(Continued)

FOREIGN PATENT DOCUMENTS

| | | |
|---|---|---|
| EP | 2028269 A1 | 2/2009 |
| EP | 2093108 | 8/2009 |

(Continued)

OTHER PUBLICATIONS

International Search Report and Written Opinion for the corresponding PCT Application No. PCT/US15/38186, dated Oct. 19, 2015, pp. 1-11.

(Continued)

Primary Examiner — Brian Whiteman
(74) Attorney, Agent, or Firm — Beusse Wolter Sanks & Maire; Timothy H. Van Dyke; Judith A. Evans

(57) ABSTRACT

Disclosed herein are methods involving the targeting of 5HT biosynthesis in gut insulin-negative cells to convert them into insulin-positive cells. Also disclosed are methods for treating a disease or disorder in a mammal, preferably a human, associated with impaired pancreatic endocrine function, by administering a therapeutically effective amount of an enumerated active agent that reduces the expression, biosynthesis, signaling or biological activity of serotonin or increases its degradation, wherein administering comprises delivering the agent to Gut Ins− cells in the mammal. Other embodiments of the method are directed to therapy wherein an agent that significantly reduces FOXO1 expression, biosynthesis, signaling or biological activity or increases its degradation is administered in addition to the agent that reduces serotonin, or alternatively an agent that reduces FOXO1 expression is targeted to serotonin-positive gut enteroendocrine cells.

9 Claims, 35 Drawing Sheets
(23 of 35 Drawing Sheet(s) Filed in Color)
Specification includes a Sequence Listing.

(56) References Cited

U.S. PATENT DOCUMENTS

| | | | |
|---|---|---|---|
| 5,220,007 A | 6/1993 | Pederson et al. | |
| 5,227,170 A | 7/1993 | Sullivan | |
| 5,256,775 A | 10/1993 | Froehler | |
| 5,264,221 A | 11/1993 | Tagawa et al. | |
| 5,354,844 A | 10/1994 | Beug et al. | |
| 5,356,633 A | 10/1994 | Woodle et al. | |
| 5,366,878 A | 11/1994 | Pederson et al. | |
| 5,395,619 A | 3/1995 | Zalipsky et al. | |
| 5,403,711 A | 4/1995 | Walder et al. | |
| 5,416,016 A | 5/1995 | Low et al. | |
| 5,417,978 A | 5/1995 | Tari et al. | |
| 5,459,127 A | 10/1995 | Felgner et al. | |
| 5,462,854 A | 10/1995 | Coassin et al. | |
| 5,469,854 A | 11/1995 | Unger et al. | |
| 5,491,133 A | 2/1996 | Walder et al. | |
| 5,512,295 A | 4/1996 | Kornberg et al. | |
| 5,521,291 A | 5/1996 | Curiel et al. | |
| 5,527,528 A | 6/1996 | Allen et al. | |
| 5,534,259 A | 7/1996 | Zalipsky et al. | |
| 5,543,152 A | 8/1996 | Webb et al. | |
| 5,543,158 A | 8/1996 | Gref et al. | |
| 5,547,932 A | 8/1996 | Curiel et al. | |
| 5,556,948 A | 9/1996 | Tagawa et al. | |
| 5,565,350 A | 10/1996 | Kmiec | |
| 5,580,575 A | 12/1996 | Unger et al. | |
| 5,583,020 A | 12/1996 | Sullivan | |
| 5,591,721 A | 1/1997 | Agrawal et al. | |
| 5,595,756 A | 1/1997 | Bally et al. | |
| 5,623,065 A | 4/1997 | Cook et al. | |
| 5,652,355 A | 7/1997 | Metelev et al. | |
| 5,652,356 A | 8/1997 | Agrawal | |
| 5,700,922 A | 12/1997 | Cook | |
| 5,877,293 A | 3/1999 | Adair et al. | |
| 5,886,152 A | 3/1999 | Nakatani et al. | |
| 6,054,297 A | 4/2000 | Carter et al. | |
| 6,355,276 B1 | 3/2002 | Illum et al. | |
| 6,560,471 B1 | 5/2003 | Heller et al. | |
| 7,431,943 B1 | 10/2008 | Villa et al. | |
| 7,563,884 B2 | 7/2009 | Cowsert et al. | |
| 7,807,649 B2 | 10/2010 | Dobie et al. | |
| 8,470,885 B2 | 6/2013 | Szewczyk | |
| 9,457,079 B2 * | 10/2016 | Talchai | G01N 33/5008 |
| 2003/0157071 A1 | 8/2003 | Wolfe et al. | |
| 2004/0023390 A1 | 2/2004 | Davidson et al. | |
| 2004/0214321 A1 | 10/2004 | Taniguchi et al. | |
| 2006/0148079 A1 | 7/2006 | Paunescu et al. | |
| 2007/0238649 A1 | 10/2007 | Kadowaki et al. | |
| 2008/0153767 A1 | 6/2008 | Dobie et al. | |
| 2008/0248995 A1 | 10/2008 | Karnieli et al. | |
| 2008/0260700 A1 | 10/2008 | Accili et al. | |
| 2013/0216554 A1 | 8/2013 | Talchai et al. | |
| 2015/0020223 A1 | 1/2015 | Zhang et al. | |

FOREIGN PATENT DOCUMENTS

| | | |
|---|---|---|
| EP | 2963108 | 8/2009 |
| JP | 2004-201595 | 7/2004 |
| WO | 85/02092 A1 | 5/1985 |
| WO | 03/100026 A2 | 12/2003 |
| WO | 2004/009630 A1 | 1/2004 |
| WO | 2004/031350 A2 | 4/2004 |
| WO | 2004031350 | 4/2004 |
| WO | 2005/037226 A2 | 7/2005 |
| WO | 2007/008982 A2 | 1/2007 |
| WO | 2007/149550 A2 | 12/2007 |
| WO | 2011/143511 A2 | 11/2011 |
| WO | 2014/153620 A1 | 10/2014 |

OTHER PUBLICATIONS

Geisauber et al., "Transplantation of Enteric Cells into the Rodent Stomach with Basic Fibroblast Growth Factor," J. Cell Sci. Ther., 2011, pp. 1-6, vol. 2.

Paulmann, N., et al., "Intracellular Serotonin Modulates Insulin Secretion from Pancreatic Beta-Cells by Protein Serotonylation," PLoS Biol., 2009, pp. 1-10, vol. 10.

Sato, T., et al., "Long-Term Expansion of Epithelial Organiods from Human Colon, Adenoma, Adenocarcinoma, and Barrett's Epithelium," Gastroenterology, 2011, pp. 1-11, vol. 141.

Aagaard, L. and Rossi, J.J., "RNAi therapeutics: principles, prospects and challenges," Adv Drug Deliv Rev 2007, pp. 75-86, vol. 59, No. 2-3.

Accili, D., et al., "FoxOs at the crossroads of cellular metabolism, differentiation, and transformation," Cell 2004, pp. 421-426, vol. 117, No. 4, Publisher: Cell Press, Published in: http://www.cell.com/abstract/S0092-8674(04)00452-0.

Alikhani, M., et al., "FOXO1 functions as a master switch that regulates gene expression necessary for tumor necrosis factor-induced fibroblast apoptosis," J Biol Chem. 2005, pp. 12096-12102, vol. 280, No. 13.

Al-Masri, M., et al., "Effect of forkhead box O1 (FOXO1) on beta cell development in the human fetal pancreas," Diabetologia 2010, pp. 699-711, vol. 53, No. 4, DOI: 10.1007/s00125-009-1632-0.

Bassett, A., et al., "Mutagenesis and homologous recombination in *Drosophila* cell lines using CRISPR/Cas9," Biology Open 2013, pp. 1-8, pii: bio.20137120v1. doi: 10.1242/bio.20137120.

Behl, Y., et al., "FOXO1 plays an important role in enhanced microvascular cell apoptosis and microvascular cell loss in type 1 and type 2 diabetic rats," Diabetes 2009, pp. 917-925, vol. 58, No. 4.

Blum, B., et al., "Functional beta-cell maturation is marked by an increased glucose threshold and by expression of urocortin 3," Nature Biotechnology 2012, pp. 261-264, vol. 30, No. 3, DOI: 10.1038/nbt.2141.

Bouchi, R., et al., "FOXO1 inhibition yields functional insulin-producing cells in human gut organoid cultures," Nat Commun 2014, pp. 1-11, vol. 5, No. 4242, Publisher: Macmillan Publishers Limited.

Brown, M., et al., "Tolerance to Single, but Not Multiple, Amino Acid Replacements in Antibody VH CDR2," J. Immunol. 1996, pp. 3285-3291, vol. 156, No. 9.

Chen, Y.J., et al., "De Novo Formation of Insulin-Producing "Neo-beta Cell Islets" from Intestinal Crypts," Cell Reports 2014, pp. 1046-1058, vol. 6, Publisher: The Authors.

Cheng, A., et al., "Multiplexed activation of endogenous genes by CRISPR-on, an RNA-guided transcriptional activator system," Cell Research 2013, pp. 1163-1171, vol. 23.

Dickinson, D.J., et al., "Engineering the Caenorhabditis elegans Genome Using Cas9Triggered Homologous Recombination," Nat. Methods. 2013, pp. 1028-1034, vol. 10, No. 10, DOI: 10.1038/nmeth.2641.

Dorsett, Y. and Tuschl, T., "siRNAs: applications in functional genomics and potential as therapeutics," Nat Rev Drug Discov. 2004, pp. 318-329, vol. 3, No. 4.

Dumitrascu, R., et al., "Terguride ameliorates monocrotaline-induced pulmonary hypertension in rats," Eur Respir J 2011, pp. 1104-1118, vol. 37.

Fujita, T. and Fujii, H., "Efficient isolation of specific genomic regions and identification of associated proteins by engineered DNA-binding molecule-mediated chromatin immunoprecipitation (enChIP) using CRISPR," Biochem. Biophys. Res. Commun. 2013, pp. 132-136, vol. 439, DOI: 10.1016/j.bbrc.2013.08.013, Publisher: Elsevier Inc.

Fujita, T. and Fujii, H., "Identification of Proteins Associated with an IFNgamma-Responsive Promoter by a Retroviral Expression System for enChIP Using CRISPR," PLoS One 2014, pp. 1-9, vol. 9, Issue 7, e103084, DOI: 10.1371/journal.pone.0103084.

Fujita, Y., et al., "Differential processing of pro-glucose-dependent insulinotropic polypeptide in gut," Am J Physiol Gastrointest Liver Physiol 2010, pp. G608-G614, vol. 298, DOI: 0.1152/ajpgi.00024.2010.

Fujita, Y., et al., "Harnessing the gut to treat diabetes," Pediatric Diabetes 2004, pp. 57-69, vol. 5, No. 2, Publisher: John Wiley & Sons, Published in: http://www.ncbi.nlm.nih.gov/pubmed/15601375.

(56) References Cited

OTHER PUBLICATIONS

Gagnon, J., et al., "Expression of PCSK1 (PC1/3), PCSK2 (PC2) and PCSK3 (furin) in mouse small intestine," Regulatory Peptides 2009, pp. 54-60, vol. 152, Issues 1-3.

Glauser, D.A. and Schlegel, W., "FoxO proteins in pancreatic β-cells as potential therapeutic targets in diabetes," Expert Review of Endocrinology & Metabolism 2008, pp. 175-185, vol. 3, DOI: doi/full/10.1586/17446651.3.2.175.

Goldfine, I.D., et al., "The endocrine secretion of human insulin and growth hormone by exocrine glands of the gastrointestinal tract," Nature Biotechnology 1997, pp. 1378-1382, vol. 15, Publisher: Nature Publishing Group, Published in: http://www.nature.com/nbt/journal/v15/n13/abs/nbt1297-1378.html.

Goodrich, A.D., et al., "In vivo generation of β-cell-like cells from CD34+ cells differentiated from human embryonic stem cells," Experimental Hematology 2010, pp. 516-525, vol. 38.

Gradwohl, G., et al., "Neurogenin3 is required for the development of the four endocrine cell lineages of the pancreas," Proc Natl Acad Sci USA 2000, pp. 1607-1611, vol. 97, No. 4.

Gratz, S.J., et al., "Genome engineering of *Drosophila* with the CRISPR RNA-guided Cas9 nuclease," Genetics 2013, pp. 1029-1035, vol. 194, No. 4, DOI: 10.1534/genetics.113.152710.

Habib, A.M., et al., "Overlap of endocrine hormone expression in the mouse intestine revealed by transcriptional profiling and flow cytometry," Endocrinology 2012, pp. 3054-3065, vol. 153, No. 7.

Haeusler, R.A., et al., "FoxOs function synergistically to promote glucose production," Journal of Biological Chemistry 2010, pp. 35245-35248, vol. 285, No. 46, Publisher: The American Society for Biochemistry and Molecular Biology, Inc., Published in: http://www.jbc.org/content/285/46/35245.full.

Han, J., et al., "Engineered Enteroendocrine Cells Secrete Insulin in Response to Glucose and Reverse Hyperglycemia in Diabetic Mice," Molecular Therapy 2007, pp. 1195-1202, vol. 15, Issue 6.

Heinrich, G., et al., "Preserved Energy Balance in Mice Lacking FoxO1 in Neurons of Nkx2.1 Lineage Reveals Functional Heterogeneity of FoxO1 Signaling Within the Hypothalamus, Diabetes 2014, pp. 1572-1582, vol. 63.

Hou, Z., et al., "Efficient genome engineering in human pluripotent stem cells using Cas9 from Neisseria meningitides," Proc Natl Acad Sci U S A 2013, pp. 15644-15649, vol. 110, No. 39.

EPO: Examination Report, European Patent Application No. 11781319.6, dated Jan. 25, 2017, 5 pages.

EPO: Examination Report, European Patent Application No. 11781319.6, dated Apr. 19, 2016, 7 pages.

EPO: Extended Search Report, European Patent Application No. 11781319.6, dated Mar. 17, 2015, 12 pages.

EPO: Partial Supplementary Search Report, European Patent Application No. 11781319.6, dated Nov. 27, 2014, 8 pages.

Ilkova, H., et al., "Induction of Long-Term Glycemic Control in Newly Diagnosed Type 2 Diabetic Patients by Transient Intensive Insulin Treatment," Diabetes Care 1997, pp. 1353-1356, vol. 20, No. 9.

ISA/US: International Search Report and Written Opinion, International Patent Application No. PCT/US2011/036360, dated Nov. 10, 2011, pp. 1-11.

ISA/US: International Search Report and Written Opinion, International Patent Application No. PCT/US2016/039569, dated Dec. 20, 2016, pp. 1-14.

Jao, L., et al., "Efficient multiplex biallelic zebrafish genome editing using a CRISPR nuclease System," Proc Natl Acad Sci. 2013, pp. 13904-13909, vol. 110, No. 34.

Jeon, K., et al., "Differentiation and transplantation of functional pancreatic beta cells generated from induced pluripotent stem cells derived from a type 1 diabetes mouse model," Stem Cells and Transport 2012, pp. 2642-2655, vol. 21, No. 14, Publisher: Mary Ann Liebert, Inc.

Jiang, W., et al., "RNA-guided editing of bacterial genomes using CRISPR-Cas systems," Nature Biotechnology 2013, pp. 233-239, vol. 31, DOI: 10.1038/nbt.2508.

Jinek, M., et al., "A programmable dual-RNA-guided DNA endonuclease in adaptive bacterial immunity," Science 2012, pp. 816-821, vol. 337.

JPO: Notice for Reasons of Refusal, Japanese Patent Application No. 257672/2015, dated Nov. 15, 2016, 14 pages.

JPO: Notice of Reasons for Refusal, Japanese Patent Application No. 510326/2013, dated Feb. 3, 2015, 7 pages (includes English translation).

JPO: Notice of Reasons for Refusal, Japanese Patent Application No. 510326/2013, dated Aug. 11, 2015, 3 pages (English translation only).

Kamagate, A., et al., "FoxO1 mediates insulin-dependent regulation of hepatic VLDL production in mice," J. Clin. Invest. 2008, pp. 2347-2364, vol. 118, No. 6.

Katic, I., et al., "CRISPR/Cas9 Genome Editing in Caenorhabditis elegans: Evaluation of Templates for Homology-Mediated Repair and Knock-Ins by Homology-Independent DNA Repair," G3 2015, pp. 1649-1656, vol. 5, DOI: 10.1534/g3.115.019273.

Kawamori, D., et al., "The forkhead transcription factor Foxo1 bridges the JNK pathway and the transcription factor PDX-1 through its intracell," The Journal of Biological Chemistry 2006, pp. 1091-1098, vol. 281, No. 2, Publisher: American Society for Biochemistry and Molecular Biology, Published in: http://www.jbc.org/content/281/2/1091.short.

Kim, M.S., et al., "Role of hypothalmic Foxo1 in the regulation of food intake and energy homeostasis," Nature Neuroscience 2006, pp. 901-906, vol. 9, Publisher: The Nature Publishing Group, Published in: http://www.nature.com/neuro/journal/v9/n7/full/nn1731.html.

Kitamura, T., et al., "A Foxo/Notch pathway controls myogenic differentiation and fiber type specification," J Clin Invest. 2007, pp. 2477-2485, vol. 117, No. 9.

Kitamura, T., et al., "Forkhead protein FoxO1 mediates Agrp-dependent targs of leptin on food intake," Nature Medicine 2006, pp. 534-540, vol. 12, Publisher: Nature Publishing Group, Published in: http://www.nature.com/nm/journal/v12/n5/full/nm1392.html.

Kitamura, T., et al., "Regulation of pancreatic juxtaductal endocrine cell formation by FoxO1," Molecular and Cellular Biology 2009, pp. 4417-4430, vol. 29, No. 16, Publisher: American Society for Microbiology, Published in: http://www.ncbi.nlm.nih.gov/pmc/articles/PMC2725741/.

Kitamura, T., et al., "The forkhead transcription factor Foxo1 links insulin signaling to Pdx1 regulation of pancreatic beta cell growth," Journal of Clinical Investigation 2002, pp. 1839-1847, vol. 110, No. 12, Publisher: American Society for Clinical Investigation, Published in: http://www.jci.org/articles/view/16857.

Kitamura, Y.I., et al., "FoxO1 protects against pancreatic beta cell failure through NeuroD and MafA induction," Cell Metabolism 2005, pp. 153-163, vol. 2, No. 3, Publisher: Elsevier Inc., Published in: http://www.cell.com/cell-metabolism/retrieve/pii/S1550413105002329.

Konner, A.C., et al., "Insulin Action in AgRP-Expressing Neurons Is Required for Suppression of Hepatic Glucose Production," Cell Metabolism 2007, pp. 438-449, vol. 5, No. 6, Publisher: Cell Press, Published in: http://www.cell.com/cell-metabolism/retrieve/pii/S1550413107001313.

Kroon, E., et al., "Pancreatic endoderm derived from human embryonic stem cells generates glucose-responsive insulin-secreting cells in vivo," Nat Biotechnol. 2008, pp. 443-452, vol. 26, No. 4, DOI: 10.1038/nbt1393.

Lee, C.S., et al., "Neurogenin 3 is essential for the proper specification of gastric enteroendocrine cells and the maintenance of gastric epithelial cell identity," Genes Development 2002, pp. 1488-1497, vol. 16, No. 12, Publisher: CSHL Press, Published in: http://www.ncbi.nlm.nih.gov/pmc/articles/PMC186338/.

Lu, Y. and Ding, D., "Current researches and clinical application prospects of stem cells in gut," Shanghai First People's Hospital 2006, www.cqvip.com, pp. 1-14 (includes English translation).

Ma, C., "Animal Models of Disease," Modern Drug Discovery 2004, pp. 30-36, vol. 7, No. 6.

(56) References Cited

OTHER PUBLICATIONS

Maehr, R., et al., "Generation of pluripotent stem cells from patients with type 1 diabetes," Proc Natl Acad Sci U S A 2009, pp. 15768-15773, vol. 106, No. 37, DOI: 10.1073pnas.0906894106.
Mali, P., et al., "RNA-Guided Human Genome Engineering via Cas9," Science 2013, pp. 823-826, vol. 339, No. 6121, DOI: 10.1126/science.1232033.
Matsumoto, M, et al., "Impaired regulation of hepatic glucose production in mice lacking the forkhead transcription factor Foxo1 in liver," Cell Metabolism 2007, pp. 208-216, vol. 6, No. 3, Publisher: Cell Press.
Matsumoto, M., et al., "Dual role of transcription factor FoxO1 in controlling hepatic insulin sensitivity and lipid metabolism," The Journal of Clinical Investigation 2006, pp. 2464-2472, vol. 116, No. 9.
Mayhew, C.N. and Wells, J.M., "Converting human pluripotent stem cells into beta-cells: recent advances and future challenges," Curr Opin Organ Transplant. 2010, pp. 54-60, vol. 15, Issue 1.
Mccracken, K.W., et al., "Generating human intestinal tissue from pluripotent stem cells in vitro," Nature Protocols 2011, pp. 1920-1928, DOI: 10.1038/nprot.2011.410.
Mellitzer, G., et al., "Pancreatic islet progenitor cells in neurogenin 3-yellow fluorescent protein knock-add-on mice," Mol Endocrinol. 2004, pp. 2765-2776, vol. 18, No. 11.
Micallef, S.J., et al., "INSGFP/w human embryonic stem cells facilitate isolation of in vitro derived insulin-producing cells," Diabetologia 2012, pp. 694-706, vol. 55, DOI: 10.1007/s00125-011-2379-y.
Nakae, J., et al., "Regulation of insulin action and pancreatic beta-cell function by mutated alleles of the gene encoding forkhead transcription factor Foxo1," Nature Genetics 2002, pp. 245-253, vol. 32, No. 2, Publisher: Nature Publishing Group, Published in: http://www.nature.com/ng/journal/v32/n2/abs/ng890.html.
Nakae, J., et al., "The forkhead transcription factor Foxo1 (Fkhr) confers insulin sensitivity onto glucose-6-phosphatase expression," The Journal of Clinical Investigation 2001, pp. 1359-1367, vol. 8, No. 9, DOI:10.1172/JCI200112876.
Nielsen, L.B., et al., "Co-localisation of the Kir6.2/SUR1 channel complex with glucagonlike peptide-1 and glucose-dependent insulinotrophic polypeptide expression in human ileal cells and implications for glycaemic control in new onset type 1 diabetes," Eur J Endocrinol 2007, pp. 663-671, vol. 156.
Ohara-Imaizumi, M., et al., "Serotonin regulates glucose-stimulated insulin secretion from pancreatic beta cells during pregnancy," Proc Natl Acad Sci U S A 2013, pp. 19420-19425, vol. 110, No. 48.
Ohta, Y., et al., "Convergence of the insulin and serotonin programs in the pancreatic beta-cell," Diabetes 2011, pp. 3208-3216, vol. 60.
Okamoto, H., et al., "Role of the forkhead protein FoxO1 in beta cell compensation to insulin resistance," Journal of Clinical Investigation 2006, pp. 775-782, vol. 116, No. 3, Publisher: American Society for Clinical Investigation, Published in: http://www.jci.org/articles/view/24967/pdf.
Pajvani, U.B., et al., "Inhibition of Notch signaling amerliorates insuin resistance in a FoxO1-dependent manner," Nature Medicine 2011, pp. 961-967, vol. 17, Publisher: Nature Publishing Group, Published in: http://www.nature.com/nm/journal/v17/n8/abs/nm.2378.html.
Plum, L., et al., "The obesity susceptibility gene Cpe links FoxO1 signaling in hypothalamic pro-opiomelanocortin neurons with regulation of food intake," Nature Medicine 2009, pp. 1195-1201, vol. 15, Publisher: Nature Publishing Group, Published in: http://www.nature.com/nm/journal/v15/n10/abs/nm.2026.html.
Potente, M., et al., "Involvement of Foxo transcription factors in angiogenesis and postnatal neovascularization," J. Clin. Invest. 2005, pp. 2382-2392, vol. 115, DOU: 10.1172/JCI23126.
Qian, S., et al., "Neither agouti-related protein nor neuropeptide Y is critically required for the regulation of energy homeostasis in mice," Molecular and Cellular Biology 2002, pp. 5027-5032, vol. 22, No. 14, Publisher: American Society for Microbiology, Published in: http://mcb.asm.org/content/22/14/5027.abstract.
Ropelle, E.R., et al., "Inhibition of hypothalamic Foxo1 expression reduced food intake in diet-induced obesity rats," J Physiol 2009, pp. 2341-2351, vol. 587, No. 10, Published in doi: 10.1113/jphysiol.2009.170050.
Samarin, J., et al., "FoxO Proteins Mediate Hypoxic Induction of Connective Tissue Growth Factor in Endothelial Cells," The Journal of Biological Chemistry 2010, pp. 4328-4336, vol. 285, No. 7, Publisher: The American Society for Biochemistry and Molecular Biology, Inc.
Samuel, V.T., et al., "Targeting Foxo1 in Mice Using Antisense Oligonucleotide Improves Hepatic and Peripheral Insulin Action," Diabetes 2006, pp. 2042-2050, vol. 55, No. 7, DOI: 10.2337/db05-0705.
Schonhoff, S.E., et al., "Neurogenin 3-expressing progenitor cells in the gastrointestinal tract differentiate into both endocrine and non-endocrine cell types," Developmental Biology 2004, pp. 443-454, vol. 270, No. 2, Publisher: Elsevier Science, Published in: http://www.sciencedirect.com/science/article/pii/S0012160604002015.
Schulz, T.C., et al, "A scalable system for production of functional pancreatic progenitors from human embryonic stem cells," PLoS One 2012, pp. 1-17, vol. 7, Issue 5, e37004.
Schwitzgebel, V.M., et al., "Expression of neurogenin3 reveals an islet cell precursor population in the pancreas," Development 2000, pp. 3533-3542, vol. 127; Publisher: The Company of Biologists Limited 2000.
Scoville, D.H., et al., "Current view: intestinal stem cells and signaling," Gastroenterology 2008, pp. 849-864, vol. 134, Issue 3.
SIPO: Decision of Rejection, Chinese Patent Application No. 2011800345425, dated Jun. 27, 2016, 8 pages (includes English translation).
SIPO: Text of First Office Action, Chinese Patent Application No. 2011800345425, dated Sep. 16, 2014, 4 pages (English translation only).
SIPO: Text of Reexamination, Chinese Patent Application No. 2011800345425, dated May 25, 2017, 9 pages (includes English translation).
SIPO: Text of Second Office Action, Chinese Patent Application No. 2011800345425, dated Apr. 24, 2015, 3 pages (English translation only).
SIPO: Text of Third Office Action, Chinese Patent Application No. 2011800345425, dated Jan. 4, 2016, 6 pages (includes English translation).
Spence, J.R., et al., "Directed differentiation of human pluripotent stem cells into intestinal tissue in vitro," Nature 2011, pp. 105-109, vol. 470, DOI: 1038/nature09691.
Takahashi, K.A. and Cone, R.D., "Fasting Induces a Large, Leptin-Dependent Increase in the Intrinsic Action Potential Frequency of Orexigenic Arcuate Nucleus Neuropeptide Y/Agouti-Related Protein Neurons," Endocrinology 2005, pp. 1043-1047, vol. 146, No. 3, Publisher: Endocrine Society, Published in: http://endo.endojournals.org/content/146/3/1043.long.
Talchai, C., et al., "Generation of functional insulin-producing cells in the gut by Foxo1 ablation," Nature Genetics 2012, pp. 406-412, vol. 44, No. 4, DOI: 10.1038/ng.2215.
Talchai, C., et al., "Genetic and biochemical pathways of beta-cell failure in type 2 diabetes," Diabetes, Obesity, and Metabolism 2009, pp. 38-45, vol. 11, No. 4, Publisher: Blackwell Publishing Ltd, Published in: http://onlinelibrary.wiley.com/doi/10.1111/j.1463-1326.2009.01115.x/abstract.
Talchai, C., et al., "Pancreatic beta Cell Dedifferentiation as a Mechanism of Diabetic beta Cell Failure," Cell 2012, pp. 1223-1234, vol. 150, No. 6.
Talchai, S.C. and Accili, D., "Legacy Effect of Foxo1 in Pancreatic Endocrine Progenitors on Adult Beta-Cell Mass and Function," Diabetes 2015, pp. 2868-2879, vol. 64, No. 8.
Tanaka, H., et al., "Effects of the novel Foxo1 inhibitor AS1708727 on plasma glucose and triglyceride levels in diabetic db/db mice," Eur J Pharmacol 2010, pp. 185-191, vol. 645, Issues 1-3.
Teo, A. K. K., et al., "Derivation of human induced pluripotent stem cells from patients with maturity onset diabetes of the young," J Biol Chem. 2013, pp. 5353-5356, vol. 288, No. 8, Publisher: The American Society for Biochemistry and Molecular Biology, Inc.

(56) References Cited

OTHER PUBLICATIONS

Thaler, J.P. and Cummings, D.E., "Minireview: Hormonal and metabolic mechanisms of diabetes remission after gastrointestinal surgery," Endocrinology 2009, pp. 2518-2525, vol. 150, No. 6, Publisher: The Endocrine Society, Published in: http://endo.endojournals.org/content/150/6/2518.long.

Thorel, F., et al., "Conversion of adult pancreatic alpha-cells to beta-cells after extreme beta-cell loss," Nature 2010, pp. 1149-1154, vol. 464, No. 7292, DOI: 10.1038/nature08894.

Vajdos, F.F. et al., "Comprehensive Functional Maps of the Antigen-Binding Site of an Anti-ErbB2 Antibody Obtained With Shotgun Scanning Mutagenesis," J Mol Bio 2002, pp. 415-428, vol. 320, No. 2.

Van Der Flier, L.G., et al., "OLFM4 is a robust marker for stem cells in human intestine and marks a subset of colorectal cancer cells," Gastroenterology 2009, pp. 15-17, vol. 137, No. 1, DOI: 10.1053/j.gastro.2009.05.035.

Villasenor, A., et al., "EphB3 marks delaminating endocrine progenitor cells in the developing pancreas," Dev Dyn 2012, pp. 1008-1019, vol. 241, No. 5, DOI: 0.1002/dvdy.23781.

Wang, T., et al., "Genetic screens in human cells using the CRISPR-Cas9 system," Science 2014, pp. 80-84, vol. 343, DOI: 10.1126/science.1246981.

Warzocha, K. and Wotowiec, D., "Antisense Strategy: Biological Utility and Prospects in the Treatment of Hematological Malignancies," Leuk Lymphoma 1997, pp. 267-281, vol. 24, No. 3-4.

Wideman, R.D., et al., "Insulin-expressing engineered cell lines and primary cells: surrogate [beta] cells from liver, gut, and other sources," Current Opinion in Organ Transplantation 2007, pp. 67-72, vol. 12, No. 1, Publisher: Wolters Kuwer Lippincot: Williams & Wilkins, Published in: http://journals.lww.com/co-transplantation/Abstract/2007/02000/Insulin_expressing_engineered_cell_lines_and.13.aspx.

Xu, X., et al., "Beta cells can be generated from endogenous progenitors in injured adult mouse pancreas," Cell 2008, pp. 197-207, vol. 132, Issue 2.

Yin, X., et al., "Niche-independent high-purity cultures of Lgr5+ intestinal stem cells and their progeny," Nature Methods 2014, pp. 106-112, vol. 11, DOI: 1038/nmeth.2737.

Ziegler, T.R., et al., "A comparison of rat small intestinal insulin and insulin-like growth factor I receptors during fasting and refeeding," Endocrinology 1995, pp. 5148-5154, vol. 136, No. 11, Publisher: The Endocrine Society, Published in: http://www.ncbi.nlm.nih.gov/pubmed/7588253.

Nagashima, T., et al., "Discovery of a Novel Forkhead Box 01 Inhibitors for Treating Type 2 Diabetes: Improvement of Fasting Glycemia in Diabetic db/db Mice," Molecular Pharmacology, vol. 78, No. 5, Aug. 24, 2010, pp. 961-970.

EP Supplemental Search Report for EP Appln. No. 15811242.5, dated Jan. 4, 2018, pp. 1-14.

* cited by examiner

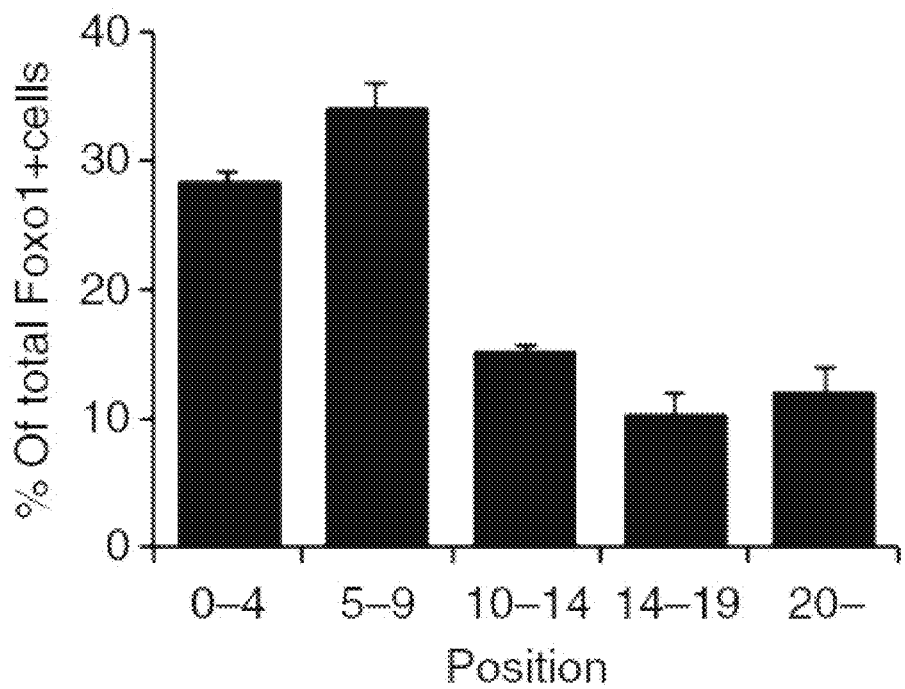
FIG. 2A
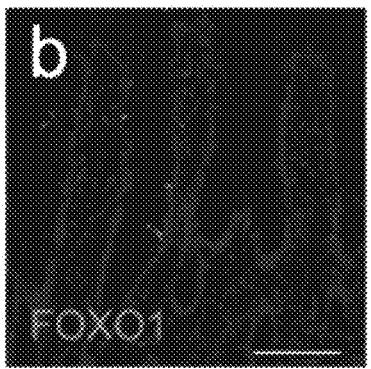 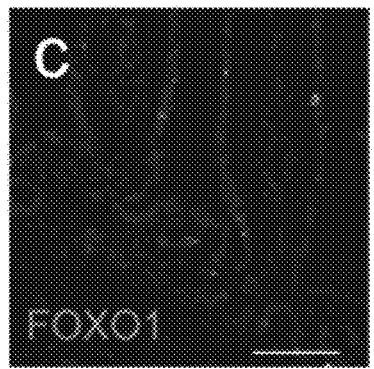 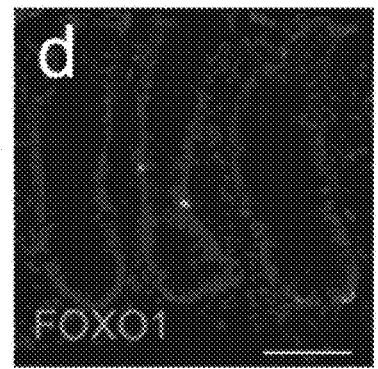
FIG. 2B        FIG. 2C        FIG. 2D FIG. 7D 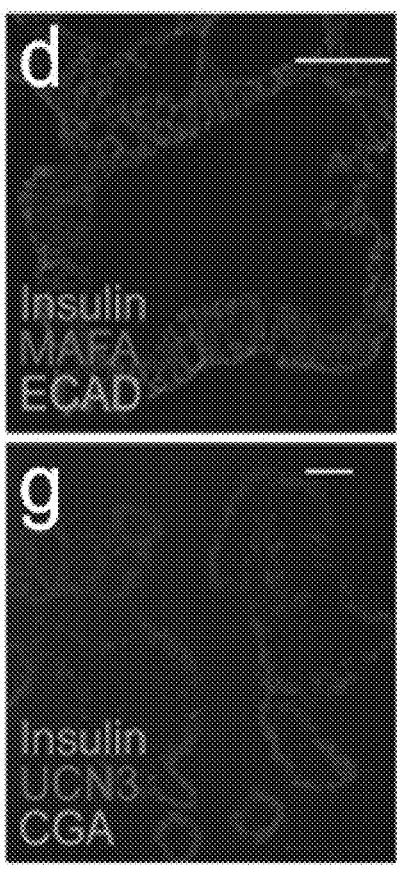 FIG. 7E
FIG. 7G 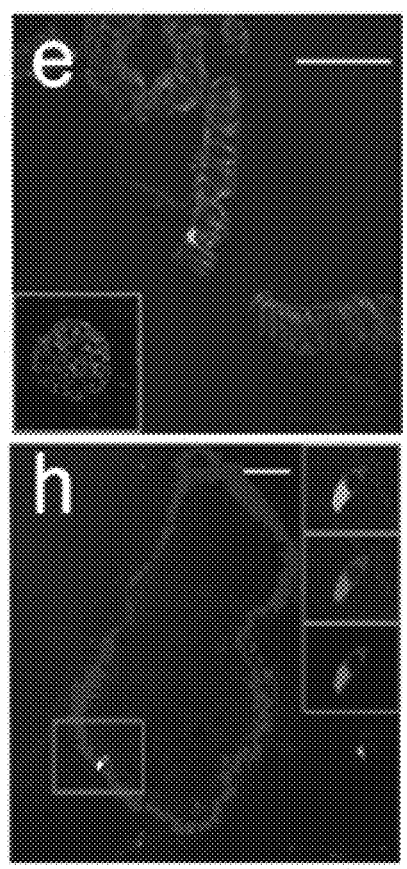 FIG. 7H Control    Δ256

Control　　　Δ256

```
                      SEQUENCE LISTING

<160> NUMBER OF SEQ ID NOS: 105

<210> SEQ ID NO 1
<211> LENGTH: 21
<212> TYPE: DNA
<213> ORGANISM: Artificial Sequence
<220> FEATURE:
<223> OTHER INFORMATION: Synthetic: Foxo1 target sequence

<400> SEQUENCE: 1
gcaccgactt tatgagcaac c                                                 21

<210> SEQ ID NO 2
<211> LENGTH: 17
<212> TYPE: DNA
<213> ORGANISM: Artificial Sequence
<220> FEATURE:
<223> OTHER INFORMATION: Synthetic: FOXO1-antisense

<400> SEQUENCE: 2
ttgggtcagg cggttca                                                      17

<210> SEQ ID NO 3
<211> LENGTH: 20
<212> TYPE: DNA
<213> ORGANISM: Artificial Sequence
<220> FEATURE:
<223> OTHER INFORMATION: Synthetic: FOXO3a-sense

<400> SEQUENCE: 3
cccagcctaa ccagggaagt                                                   20

<210> SEQ ID NO 4
<211> LENGTH: 16
<212> TYPE: DNA
<213> ORGANISM: Artificial Sequence
<220> FEATURE:
<223> OTHER INFORMATION: Synthetic: FOXO3a-antisense

<400> SEQUENCE: 4
```

```
agcgccctgg gtttgg                                                     16

<210> SEQ ID NO 5
<211> LENGTH: 21
<212> TYPE: DNA
<213> ORGANISM: Artificial Sequence
<220> FEATURE:
<223> OTHER INFORMATION: Synthetic: FOXO4-sense

<400> SEQUENCE: 5
cctgcacagc aagttcatca a                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic: FOXO4-antisense

<400> SEQUENCE: 6
ttcagcatcc accaagagct t                                               21

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer sequence for INSULIN

<400> SEQUENCE: 7
ccagctggta gagggagcag at                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer sequence for INSULIN

<400> SEQUENCE: 8
tacctagtgt gcggggaacg ag                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer sequence for NEUROGENIN3

<400> SEQUENCE: 9
tacatctggg cgctgactca aa                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic Primer sequence for NEUROGENIN3

<400> SEQUENCE: 10
agcctgggag actggggagt ag                                              22

<210> SEQ ID NO 11
<211> LENGTH: 22
<212> TYPE: DNA
<213> ORGANISM: Artificial Sequence
```

```
<220> FEATURE:
<223> OTHER INFORMATION: Synthetic Primer sequence for CHROMOGRANIN A

<400> SEQUENCE: 11
gctccctgtg aacagcccta tg                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer sequence for CHROMOGRANIN A

<400> SEQUENCE: 12
cgaggtcttg gagctccttc ag                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer sequence for FOXO1

<400> SEQUENCE: 13
gatggtcaag agcgtgccct ac                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer sequence for FOXO1

<400> SEQUENCE: 14
tggattgagc atccaccaag aa                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic Primer sequence for FOXO3

<400> SEQUENCE: 15
ttgcgtgccc tacttcaagg at                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic Primer sequence for FOXO3

<400> SEQUENCE: 16
agagctcttg ccagttccct ca                                              22

<210> SEQ ID NO 17
<211> LENGTH: 22
<212> TYPE: DNA
<213> ORGANISM: Artificial Sequence
<220> FEATURE:
<223> OTHER INFORMATION: Synthetic Primer sequence for FOXO4

<400> SEQUENCE: 17
tcaaggacaa gggtgacagc aa                                              22
```

<210> SEQ ID NO 18
<211> LENGTH: 22
<212> TYPE: DNA
<213> ORGANISM: Artificial Sequence
<220> FEATURE:
<223> OTHER INFORMATION: Synthetic Primer sequence for FOXO4

<400> SEQUENCE: 18
agggttcagc atccaccaag ag        22

<210> SEQ ID NO 19
<211> LENGTH: 22
<212> TYPE: DNA
<213> ORGANISM: Artificial Sequence
<220> FEATURE:
<223> OTHER INFORMATION: Synthetic Primer sequence for VILLIN

<400> SEQUENCE: 19
cagtacccac caagcacaca gg        22

<210> SEQ ID NO 20
<211> LENGTH: 22
<212> TYPE: DNA
<213> ORGANISM: Artificial Sequence
<220> FEATURE:
<223> OTHER INFORMATION: Synthetic Primer sequence for VILLIN

<400> SEQUENCE: 20
atggatgtgg catcgaactt ca        22

<210> SEQ ID NO 21
<211> LENGTH: 22
<212> TYPE: DNA
<213> ORGANISM: Artificial Sequence
<220> FEATURE:
<223> OTHER INFORMATION: Synthetic Primer sequence for LYSOZYME

<400> SEQUENCE: 21
tggctacagg ggaatcagcc ta        22

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer sequence for LYSOZYME

<400> SEQUENCE: 22
ttaactgctc ctggggtttt gc        22

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer sequence for MUC2

<400> SEQUENCE: 23
gtggagtcca gcacgggcat        20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer sequence for MUC2

```
<400> SEQUENCE: 24
tcaccaccat gtggtcccgc                                         20

<210> SEQ ID NO 25
<211> LENGTH: 22
<212> TYPE: DNA
<213> ORGANISM: Artificial Sequence
<220> FEATURE:
<223> OTHER INFORMATION: Synthetic Primer sequence for CDX2

<400> SEQUENCE: 25
atcgagtggt gtacacggac ca                                      22

<210> SEQ ID NO 26
<211> LENGTH: 22
<212> TYPE: DNA
<213> ORGANISM: Artificial Sequence
<220> FEATURE:
<223> OTHER INFORMATION: Synthetic Primer sequence for CDX2

<400> SEQUENCE: 26
ctctcctttg ctctgcggtt ct                                      22

<210> SEQ ID NO 27
<211> LENGTH: 22
<212> TYPE: DNA
<213> ORGANISM: Artificial Sequence
<220> FEATURE:
<223> OTHER INFORMATION: Synthetic Primer sequence for PC1

<400> SEQUENCE: 27
ataatcacaa atgcggggtt gg                                      22

<210> SEQ ID NO 28
<211> LENGTH: 22
<212> TYPE: DNA
<213> ORGANISM: Artificial Sequence
<220> FEATURE:
<223> OTHER INFORMATION: Synthetic Primer sequence for PC1

<400> SEQUENCE: 28
atcatcatta gggccccagc tt                                      22

<210> SEQ ID NO 29
<211> LENGTH: 22
<212> TYPE: DNA
<213> ORGANISM: Artificial Sequence
<220> FEATURE:
<223> OTHER INFORMATION: Synthetic Primer sequence for PC2

<400> SEQUENCE: 29
ttgcataaag ggggagagga ca                                      22

<210> SEQ ID NO 30
<211> LENGTH: 22
<212> TYPE: DNA
<213> ORGANISM: Artificial Sequence
<220> FEATURE:
<223> OTHER INFORMATION: Synthetic Primer sequence for PC2

<400> SEQUENCE: 30
cttcctgctg caaagccatc tt                                      22

<210> SEQ ID NO 31
```

```
<211> LENGTH: 22
<212> TYPE: DNA
<213> ORGANISM: Artificial Sequence
<220> FEATURE:
<223> OTHER INFORMATION: Synthetic Primer sequence for GLUT2

<400> SEQUENCE: 31
tgggatgttt gtttgtgcca tc                                              22

<210> SEQ ID NO 32
<211> LENGTH: 22
<212> TYPE: DNA
<213> ORGANISM: Artificial Sequence
<220> FEATURE:
<223> OTHER INFORMATION: Synthetic Primer sequence for GLUT2

<400> SEQUENCE: 32
caggacgtgg tccttgactg aa                                              22

<210> SEQ ID NO 33
<211> LENGTH: 22
<212> TYPE: DNA
<213> ORGANISM: Artificial Sequence
<220> FEATURE:
<223> OTHER INFORMATION: Synthetic Primer sequence for GCK

<400> SEQUENCE: 33
tgagtgcatc tccgacttcc tg                                              22

<210> SEQ ID NO 34
<211> LENGTH: 22
<212> TYPE: DNA
<213> ORGANISM: Artificial Sequence
<220> FEATURE:
<223> OTHER INFORMATION: Synthetic Primer sequence for GCK

<400> SEQUENCE: 34
cgtttgatag cgtctcgcag aa                                              22

<210> SEQ ID NO 35
<211> LENGTH: 22
<212> TYPE: DNA
<213> ORGANISM: Artificial Sequence
<220> FEATURE:
<223> OTHER INFORMATION: Synthetic Primer sequence for KIR6.2

<400> SEQUENCE: 35
ttgatgccaa cagcccactc ta                                              22

<210> SEQ ID NO 36
<211> LENGTH: 22
<212> TYPE: DNA
<213> ORGANISM: Artificial Sequence
<220> FEATURE:
<223> OTHER INFORMATION: Synthetic Primer sequence for KIR6.2

<400> SEQUENCE: 36
tcctcagcta caatgggcac aa                                              22

<210> SEQ ID NO 37
<211> LENGTH: 22
<212> TYPE: DNA
<213> ORGANISM: Artificial Sequence
<220> FEATURE:
<223> OTHER INFORMATION: Synthetic Primer sequence for SUR1

<400> SEQUENCE: 37
```

-continued agtggccaca cacattgctc at                                            22

<210> SEQ ID NO 38
<211> LENGTH: 22
<212> TYPE: DNA
<213> ORGANISM: Artificial Sequence
<220> FEATURE:
<223> OTHER INFORMATION: Synthetic Primer sequence for SUR1

<400> SEQUENCE: 38
gaaggagtgg atgctggtga ca                                            22

<210> SEQ ID NO 39
<211> LENGTH: 22
<212> TYPE: DNA
<213> ORGANISM: Artificial Sequence
<220> FEATURE:
<223> OTHER INFORMATION: Synthetic Primer sequence for PAX6

<400> SEQUENCE: 39
actctgcgct tggccaagaa ct                                            22

<210> SEQ ID NO 40
<211> LENGTH: 22
<212> TYPE: DNA
<213> ORGANISM: Artificial Sequence
<220> FEATURE:
<223> OTHER INFORMATION: Synthetic Primer sequence for PAX6

<400> SEQUENCE: 40
gggctgaggg gtccatcaaa gg                                            22

<210> SEQ ID NO 41
<211> LENGTH: 22
<212> TYPE: DNA
<213> ORGANISM: Artificial Sequence
<220> FEATURE:
<223> OTHER INFORMATION: Synthetic Primer sequence for PAX4

<400> SEQUENCE: 41
gggctgactg taccaagggt tg                                            22

<210> SEQ ID NO 42
<211> LENGTH: 22
<212> TYPE: DNA
<213> ORGANISM: Artificial Sequence
<220> FEATURE:
<223> OTHER INFORMATION: Synthetic Primer sequence for PAX4

<400> SEQUENCE: 42
gcagggcttg agacaggctt ta                                            22

<210> SEQ ID NO 43
<211> LENGTH: 22
<212> TYPE: DNA
<213> ORGANISM: Artificial Sequence
<220> FEATURE:
<223> OTHER INFORMATION: Synthetic Primer sequence for NKX2.2

<400> SEQUENCE: 43
ttctacgaca gcagcgacaa cc                                            22

<210> SEQ ID NO 44
<211> LENGTH: 22
<212> TYPE: DNA

```
<213> ORGANISM: Artificial Sequence
<220> FEATURE:
<223> OTHER INFORMATION: Synthetic Primer sequence for NKX2.2

<400> SEQUENCE: 44
ttgtcattgt ccggtgactc gt                                          22

<210> SEQ ID NO 45
<211> LENGTH: 22
<212> TYPE: DNA
<213> ORGANISM: Artificial Sequence
<220> FEATURE:
<223> OTHER INFORMATION: Synthetic Primer sequence for NKX6.1

<400> SEQUENCE: 45
gcctattcgt tgggatgac ag                                           22

<210> SEQ ID NO 46
<211> LENGTH: 22
<212> TYPE: DNA
<213> ORGANISM: Artificial Sequence
<220> FEATURE:
<223> OTHER INFORMATION: Synthetic Primer sequence for NKX6.1

<400> SEQUENCE: 46
cgagttggga tccagaggct ta                                          22

<210> SEQ ID NO 47
<211> LENGTH: 22
<212> TYPE: DNA
<213> ORGANISM: Artificial Sequence
<220> FEATURE:
<223> OTHER INFORMATION: Synthetic Primer sequence for ARX

<400> SEQUENCE: 47
gaaacgcaaa cagaggcgct ac                                          22

<210> SEQ ID NO 48
<211> LENGTH: 22
<212> TYPE: DNA
<213> ORGANISM: Artificial Sequence
<220> FEATURE:
<223> OTHER INFORMATION: Synthetic Primer sequence for ARX

<400> SEQUENCE: 48
ggttctggaa ccagacctgg ac                                          22

<210> SEQ ID NO 49
<211> LENGTH: 22
<212> TYPE: DNA
<213> ORGANISM: Artificial Sequence
<220> FEATURE:
<223> OTHER INFORMATION: Synthetic Primer sequence for NEUROD1

<400> SEQUENCE: 49
aagagacgcg gcccccaaaaa ga                                         22

<210> SEQ ID NO 50
<211> LENGTH: 22
<212> TYPE: DNA
<213> ORGANISM: Artificial Sequence
<220> FEATURE:
<223> OTHER INFORMATION: Synthetic Primer sequence for NEUROD1

<400> SEQUENCE: 50
tcttggccaa gcgcagagtc tc                                          22
```

```
<210> SEQ ID NO 51
<211> LENGTH: 22
<212> TYPE: DNA
<213> ORGANISM: Artificial Sequence
<220> FEATURE:
<223> OTHER INFORMATION: Synthetic Primer sequence for MAFA

<400> SEQUENCE: 51
tccttgtaca ggtcccgctc tt                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic Primer sequence for MAFA

<400> SEQUENCE: 52
cagtgccaac tcgctcttag gc                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic Primer sequence for MAFB

<400> SEQUENCE: 53
gttgctcgcc atccagtaca ga                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic Primer sequence for MAFB

<400> SEQUENCE: 54
tggattgagc atccaccaag aa                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic Primer sequence for PDX1

<400> SEQUENCE: 55
ctgcctttcc catggatgaa gt                                              22

<210> SEQ ID NO 56
<211> LENGTH: 22
<212> TYPE: DNA
<213> ORGANISM: Artificial Sequence
<220> FEATURE:
<223> OTHER INFORMATION: Synthetic Primer sequence for PDX1

<400> SEQUENCE: 56
cggccgtgag atgtacttgt tg                                              22

<210> SEQ ID NO 57
<211> LENGTH: 22
<212> TYPE: DNA
<213> ORGANISM: Artificial Sequence
<220> FEATURE:
```

<223> OTHER INFORMATION: Synthetic Primer sequence for ISLET1

<400> SEQUENCE: 57
agcagcagcc caatgacaaa ac                                              22

<210> SEQ ID NO 58
<211> LENGTH: 22
<212> TYPE: DNA
<213> ORGANISM: Artificial Sequence
<220> FEATURE:
<223> OTHER INFORMATION: Synthetic Primer sequence for ISLET1

<400> SEQUENCE: 58
cagttgctga aaagcaggct ga                                              22

<210> SEQ ID NO 59
<211> LENGTH: 22
<212> TYPE: DNA
<213> ORGANISM: Artificial Sequence
<220> FEATURE:
<223> OTHER INFORMATION: Synthetic Primer sequence for RFX6

<400> SEQUENCE: 59
atcagcagca ttcgttcact gc                                              22

<210> SEQ ID NO 60
<211> LENGTH: 22
<212> TYPE: DNA
<213> ORGANISM: Artificial Sequence
<220> FEATURE:
<223> OTHER INFORMATION: Synthetic Primer sequence for RFX6

<400> SEQUENCE: 60
ggaagaagga attggggttt gc                                              22

<210> SEQ ID NO 61
<211> LENGTH: 22
<212> TYPE: DNA
<213> ORGANISM: Artificial Sequence
<220> FEATURE:
<223> OTHER INFORMATION: Synthetic Primer sequence for SLC30A-8

<400> SEQUENCE: 61
gagcgcctgc tgtatcctga tt                                              22

<210> SEQ ID NO 62
<211> LENGTH: 22
<212> TYPE: DNA
<213> ORGANISM: Artificial Sequence
<220> FEATURE:
<223> OTHER INFORMATION: Synthetic Primer sequence for SLC30A-8

<400> SEQUENCE: 62
atgcacaaaa gcagctctga cg                                              22

<210> SEQ ID NO 63
<211> LENGTH: 22
<212> TYPE: DNA
<213> ORGANISM: Artificial Sequence
<220> FEATURE:
<223> OTHER INFORMATION: Synthetic Primer sequence for UROCORTIN3

<400> SEQUENCE: 63
aggcctcccc cacaagttct ac                                              22

```
<210> SEQ ID NO 64
<211> LENGTH: 22
<212> TYPE: DNA
<213> ORGANISM: Artificial Sequence
<220> FEATURE:
<223> OTHER INFORMATION: Synthetic Primer sequence for UROCORTIN3

<400> SEQUENCE: 64
ttctctttgc cctcctcctc ct                                              22

<210> SEQ ID NO 65
<211> LENGTH: 22
<212> TYPE: DNA
<213> ORGANISM: Artificial Sequence
<220> FEATURE:
<223> OTHER INFORMATION: Synthetic Primer sequence for LGR5

<400> SEQUENCE: 65
ttcctcaaac cgtctgcaat ca                                              22

<210> SEQ ID NO 66
<211> LENGTH: 22
<212> TYPE: DNA
<213> ORGANISM: Artificial Sequence
<220> FEATURE:
<223> OTHER INFORMATION: Synthetic Primer sequence for LGR5

<400> SEQUENCE: 66
ggaggctaag caactgctgg aa                                              22

<210> SEQ ID NO 67
<211> LENGTH: 22
<212> TYPE: DNA
<213> ORGANISM: Artificial Sequence
<220> FEATURE:
<223> OTHER INFORMATION: Synthetic Primer sequence for OLFM4

<400> SEQUENCE: 67
tggctctgaa gaccaagctg aa                                              22

<210> SEQ ID NO 68
<211> LENGTH: 22
<212> TYPE: DNA
<213> ORGANISM: Artificial Sequence
<220> FEATURE:
<223> OTHER INFORMATION: Synthetic Primer sequence for OLFM4

<400> SEQUENCE: 68
gtaatcccta ccccaagcac ca                                              22

<210> SEQ ID NO 69
<211> LENGTH: 22
<212> TYPE: DNA
<213> ORGANISM: Artificial Sequence
<220> FEATURE:
<223> OTHER INFORMATION: Synthetic Primer sequence for BMI1

<400> SEQUENCE: 69
tgctgccaat ggctctaatg aa                                              22

<210> SEQ ID NO 70
<211> LENGTH: 22
<212> TYPE: DNA
<213> ORGANISM: Artificial Sequence
<220> FEATURE:
<223> OTHER INFORMATION: Synthetic Primer sequence for BMI1
```

-continued

```
<400> SEQUENCE: 70
ttgctgctgg gcatcgtaag ta                                              22

<210> SEQ ID NO 71
<211> LENGTH: 22
<212> TYPE: DNA
<213> ORGANISM: Artificial Sequence
<220> FEATURE:
<223> OTHER INFORMATION: Synthetic Primer sequence for MATH1

<400> SEQUENCE: 71
aatggggtgc agaagcagag ac                                              22

<210> SEQ ID NO 72
<211> LENGTH: 22
<212> TYPE: DNA
<213> ORGANISM: Artificial Sequence
<220> FEATURE:
<223> OTHER INFORMATION: Synthetic Primer sequence for MATH1

<400> SEQUENCE: 72
tcggacaagg cgttgatgta ga                                              22

<210> SEQ ID NO 73
<211> LENGTH: 22
<212> TYPE: DNA
<213> ORGANISM: Artificial Sequence
<220> FEATURE:
<223> OTHER INFORMATION: Synthetic Primer sequence for SUBSTANCE P

<400> SEQUENCE: 73
tacgacagcg accagatcaa gg                                              22

<210> SEQ ID NO 74
<211> LENGTH: 22
<212> TYPE: DNA
<213> ORGANISM: Artificial Sequence
<220> FEATURE:
<223> OTHER INFORMATION: Synthetic Primer sequence for SUBSTANCE P

<400> SEQUENCE: 74
gagcctttaa cagggccact tg                                              22

<210> SEQ ID NO 75
<211> LENGTH: 22
<212> TYPE: DNA
<213> ORGANISM: Artificial Sequence
<220> FEATURE:
<223> OTHER INFORMATION: Synthetic Primer sequence for GHRL

<400> SEQUENCE: 75
aaaggagtcg aagaagccac ca                                              22

<210> SEQ ID NO 76
<211> LENGTH: 22
<212> TYPE: DNA
<213> ORGANISM: Artificial Sequence
<220> FEATURE:
<223> OTHER INFORMATION: Synthetic Primer sequence for GHRL

<400> SEQUENCE: 76
tgctggtact gaacccctga ca                                              22

<210> SEQ ID NO 77
<211> LENGTH: 22
```

```
<212> TYPE: DNA
<213> ORGANISM: Artificial Sequence
<220> FEATURE:
<223> OTHER INFORMATION: Synthetic Primer sequence for PPY

<400> SEQUENCE: 77
ccacctgcgt ggctctgtta ct                                           22

<210> SEQ ID NO 78
<211> LENGTH: 22
<212> TYPE: DNA
<213> ORGANISM: Artificial Sequence
<220> FEATURE:
<223> OTHER INFORMATION: Synthetic Primer sequence for PPY

<400> SEQUENCE: 78
ccagcgtgtc ctctttgtgt ct                                           22

<210> SEQ ID NO 79
<211> LENGTH: 22
<212> TYPE: DNA
<213> ORGANISM: Artificial Sequence
<220> FEATURE:
<223> OTHER INFORMATION: Synthetic Primer sequence for GLUCAGON

<400> SEQUENCE: 79
aggcagaccc actcagtgat cc                                           22

<210> SEQ ID NO 80
<211> LENGTH: 22
<212> TYPE: DNA
<213> ORGANISM: Artificial Sequence
<220> FEATURE:
<223> OTHER INFORMATION: Synthetic Primer sequence for GLUCAGON

<400> SEQUENCE: 80
catcgtgacg tttggcaatg tt                                           22

<210> SEQ ID NO 81
<211> LENGTH: 22
<212> TYPE: DNA
<213> ORGANISM: Artificial Sequence
<220> FEATURE:
<223> OTHER INFORMATION: Synthetic Primer sequence for 5HT

<400> SEQUENCE: 81 caccaccctra gtggctgagc tt                                          22

<210> SEQ ID NO 82
<211> LENGTH: 22
<212> TYPE: DNA
<213> ORGANISM: Artificial Sequence
<220> FEATURE:
<223> OTHER INFORMATION: Synthetic Primer sequence for 5HT

<400> SEQUENCE: 82
ccatgatggt gtagggggagg ag                                          22

<210> SEQ ID NO 83
<211> LENGTH: 22
<212> TYPE: DNA
<213> ORGANISM: Artificial Sequence
<220> FEATURE:
<223> OTHER INFORMATION: Synthetic Primer sequence for SECRETIN

<400> SEQUENCE: 83
```
agcaggacgc agagaacagc at                                          22

<210> SEQ ID NO 84
<211> LENGTH: 22
<212> TYPE: DNA
<213> ORGANISM: Artificial Sequence
<220> FEATURE:
<223> OTHER INFORMATION: Synthetic Primer sequence for SECRETIN

<400> SEQUENCE: 84
gccagctggt tctgaaacca ta                                          22

<210> SEQ ID NO 85
<211> LENGTH: 22
<212> TYPE: DNA
<213> ORGANISM: Artificial Sequence
<220> FEATURE:
<223> OTHER INFORMATION: Synthetic Primer sequence for CCK

<400> SEQUENCE: 85
agggtatcgc agagaacgga tg                                          22

<210> SEQ ID NO 86
<211> LENGTH: 22
<212> TYPE: DNA
<213> ORGANISM: Artificial Sequence
<220> FEATURE:
<223> OTHER INFORMATION: Synthetic Primer sequence for CCK

<400> SEQUENCE: 86
gtcccggtca cttatcctgt gg                                          22

<210> SEQ ID NO 87
<211> LENGTH: 22
<212> TYPE: DNA
<213> ORGANISM: Artificial Sequence
<220> FEATURE:
<223> OTHER INFORMATION: Synthetic Primer sequence for GASTRIN

<400> SEQUENCE: 87
acccttaggt acagggccaa ac                                          22

<210> SEQ ID NO 88
<211> LENGTH: 22
<212> TYPE: DNA
<213> ORGANISM: Artificial Sequence
<220> FEATURE:
<223> OTHER INFORMATION: Synthetic Primer sequence for GASTRIN

<400> SEQUENCE: 88
gccgaagtcc atccatccat ag                                          22

<210> SEQ ID NO 89
<211> LENGTH: 22
<212> TYPE: DNA
<213> ORGANISM: Artificial Sequence
<220> FEATURE:
<223> OTHER INFORMATION: Synthetic Primer sequence for GIP

<400> SEQUENCE: 89
gcccaaaagg ggaagaagaa tg                                          22

<210> SEQ ID NO 90
<211> LENGTH: 22
<212> TYPE: DNA
<213> ORGANISM: Artificial Sequence

```
<220> FEATURE:
<223> OTHER INFORMATION: Synthetic Primer sequence for GIP

<400> SEQUENCE: 90
gccaacagct cttgaatcag ca                                              22

<210> SEQ ID NO 91
<211> LENGTH: 22
<212> TYPE: DNA
<213> ORGANISM: Artificial Sequence
<220> FEATURE:
<223> OTHER INFORMATION: Synthetic Primer sequence for SOMATOSTATIN

<400> SEQUENCE: 91
gaccccagac tccgtcagtt tc                                              22

<210> SEQ ID NO 92
<211> LENGTH: 22
<212> TYPE: DNA
<213> ORGANISM: Artificial Sequence
<220> FEATURE:
<223> OTHER INFORMATION: Synthetic Primer sequence for SOMATOSTATIN

<400> SEQUENCE: 92
ctgcagctca agcctcattt ca                                              22

<210> SEQ ID NO 93
<211> LENGTH: 22
<212> TYPE: DNA
<213> ORGANISM: Artificial Sequence
<220> FEATURE:
<223> OTHER INFORMATION: Synthetic Primer sequence for HES1

<400> SEQUENCE: 93
caacacgaca ccggataaac ca                                              22

<210> SEQ ID NO 94
<211> LENGTH: 22
<212> TYPE: DNA
<213> ORGANISM: Artificial Sequence
<220> FEATURE:
<223> OTHER INFORMATION: Synthetic Primer sequence for HES1

<400> SEQUENCE: 94
catttccaga atgtccgcct tc                                              22

<210> SEQ ID NO 95
<211> LENGTH: 22
<212> TYPE: DNA
<213> ORGANISM: Artificial Sequence
<220> FEATURE:
<223> OTHER INFORMATION: Synthetic Primer sequence for HESR1

<400> SEQUENCE: 95
ccgacgagac cggatcaata ac                                              22

<210> SEQ ID NO 96
<211> LENGTH: 22
<212> TYPE: DNA
<213> ORGANISM: Artificial Sequence
<220> FEATURE:
<223> OTHER INFORMATION: Synthetic Primer sequence for HESR1

<400> SEQUENCE: 96
ctgccgtatg cagcattttc ag                                              22
```

```
<210> SEQ ID NO 97
<211> LENGTH: 22
<212> TYPE: DNA
<213> ORGANISM: Artificial Sequence
<220> FEATURE:
<223> OTHER INFORMATION: Synthetic Primer sequence for HEYL

<400> SEQUENCE: 97
aagctggaga aagccgaggt ct                                                  22

<210> SEQ ID NO 98
<211> LENGTH: 22
<212> TYPE: DNA
<213> ORGANISM: Artificial Sequence
<220> FEATURE:
<223> OTHER INFORMATION: Synthetic Primer sequence for HEYL

<400> SEQUENCE: 98
aaaccaatgc tccggaagtc aa                                                  22

<210> SEQ ID NO 99
<211> LENGTH: 22
<212> TYPE: DNA
<213> ORGANISM: Artificial Sequence
<220> FEATURE:
<223> OTHER INFORMATION: Synthetic Primer sequence for AES

<400> SEQUENCE: 99
gcctcaagct cgaatgtgac aa                                                  22

<210> SEQ ID NO 100
<211> LENGTH: 22
<212> TYPE: DNA
<213> ORGANISM: Artificial Sequence
<220> FEATURE:
<223> OTHER INFORMATION: Synthetic Primer sequence for AES

<400> SEQUENCE: 100
tggtgctctt gggagaggta gg                                                  22

<210> SEQ ID NO 101
<211> LENGTH: 22
<212> TYPE: DNA
<213> ORGANISM: Artificial Sequence
<220> FEATURE:
<223> OTHER INFORMATION: Synthetic Primer sequence for HPRT

<400> SEQUENCE: 101
aatgaccagt caacagggga ca                                                  22

<210> SEQ ID NO 102
<211> LENGTH: 22
<212> TYPE: DNA
<213> ORGANISM: Artificial Sequence
<220> FEATURE:
<223> OTHER INFORMATION: Synthetic Primer sequence for HPRT

<400> SEQUENCE: 102
cacttcgtgg ggtccttttc ac                                                  22

<210> SEQ ID NO 103
<211> LENGTH: 444
<212> TYPE: PRT
<213> ORGANISM: Homo sapiens
<220> FEATURE:
<221> NAME/KEY: misc_feature
```

<223> OTHER INFORMATION: TPH1 protein sequence

<400> SEQUENCE: 103

```
Met Ile Glu Asp Asn Lys Glu Asn Lys Asp His Ser Leu Glu Arg Gly
1               5                   10                  15

Arg Ala Ser Leu Ile Phe Ser Leu Lys Asn Glu Val Gly Gly Leu Ile
            20                  25                  30

Lys Ala Leu Lys Ile Phe Gln Glu Lys His Val Asn Leu Leu His Ile
        35                  40                  45

Glu Ser Arg Lys Ser Lys Arg Arg Asn Ser Glu Phe Glu Ile Phe Val
    50                  55                  60

Asp Cys Asp Ile Asn Arg Glu Gln Leu Asn Asp Ile Phe His Leu Leu
65                  70                  75                  80

Lys Ser His Thr Asn Val Leu Ser Val Asn Leu Pro Asp Asn Phe Thr
                85                  90                  95

Leu Lys Glu Asp Gly Met Glu Thr Val Pro Trp Phe Pro Lys Lys Ile
            100                 105                 110

Ser Asp Leu Asp His Cys Ala Asn Arg Val Leu Met Tyr Gly Ser Glu
        115                 120                 125

Leu Asp Ala Asp His Pro Gly Phe Lys Asp Asn Val Tyr Arg Lys Arg
    130                 135                 140

Arg Lys Tyr Phe Ala Asp Leu Ala Met Asn Tyr Lys His Gly Asp Pro
145                 150                 155                 160

Ile Pro Lys Val Glu Phe Thr Glu Glu Ile Lys Thr Trp Gly Thr
                165                 170                 175

Val Phe Gln Glu Leu Asn Lys Leu Tyr Pro Thr His Ala Cys Arg Glu
            180                 185                 190

Tyr Leu Lys Asn Leu Pro Leu Leu Ser Lys Tyr Cys Gly Tyr Arg Glu
        195                 200                 205

Asp Asn Ile Pro Gln Leu Glu Asp Val Ser Asn Phe Leu Lys Glu Arg
    210                 215                 220

Thr Gly Phe Ser Ile Arg Pro Val Ala Gly Tyr Leu Ser Pro Arg Asp
225                 230                 235                 240

Phe Leu Ser Gly Leu Ala Phe Arg Val Phe His Cys Thr Gln Tyr Val
                245                 250                 255

Arg His Ser Ser Asp Pro Phe Tyr Thr Pro Glu Pro Asp Thr Cys His
            260                 265                 270

Glu Leu Leu Gly His Val Pro Leu Leu Ala Glu Pro Ser Phe Ala Gln
        275                 280                 285

Phe Ser Gln Glu Ile Gly Leu Ala Ser Leu Gly Ala Ser Glu Glu Ala
    290                 295                 300

Val Gln Lys Leu Ala Thr Cys Tyr Phe Phe Thr Val Glu Phe Gly Leu
305                 310                 315                 320

Cys Lys Gln Asp Gly Gln Leu Arg Val Phe Gly Ala Gly Leu Leu Ser
                325                 330                 335

Ser Ile Ser Glu Leu Lys His Ala Leu Ser Gly His Ala Lys Val Lys
            340                 345                 350

Pro Phe Asp Pro Lys Ile Thr Cys Lys Gln Glu Cys Leu Ile Thr Thr
        355                 360                 365

Phe Gln Asp Val Tyr Phe Val Ser Glu Ser Phe Glu Asp Ala Lys Glu
    370                 375                 380

Lys Met Arg Glu Phe Thr Lys Thr Ile Lys Arg Pro Phe Gly Val Lys
385                 390                 395                 400
```

```
Tyr Asn Pro Tyr Thr Arg Ser Ile Gln Ile Leu Lys Asp Thr Lys Ser
                405                 410                 415

Ile Thr Ser Ala Met Asn Glu Leu Gln His Asp Leu Asp Val Val Ser
            420                 425                 430

Asp Ala Leu Ala Lys Val Ser Arg Lys Pro Ser Ile
        435                 440

<210> SEQ ID NO 104
<211> LENGTH: 480
<212> TYPE: PRT
<213> ORGANISM: Homo sapiens
<220> FEATURE:
<221> NAME/KEY: misc_feature
<223> OTHER INFORMATION: L-aromatic amino acid decarboxylase protein
      sequence

<400> SEQUENCE: 104

Met Asn Ala Ser Glu Phe Arg Arg Arg Gly Lys Glu Met Val Asp Tyr
1               5                   10                  15

Val Ala Asn Tyr Met Glu Gly Ile Glu Gly Arg Gln Val Tyr Pro Asp
            20                  25                  30

Val Glu Pro Gly Tyr Leu Arg Pro Leu Ile Pro Ala Ala Ala Pro Gln
        35                  40                  45

Glu Pro Asp Thr Phe Glu Asp Ile Ile Asn Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Glu Leu
        115                 120                 125

Pro Lys Ala Phe Leu Asn Glu Lys Ala Gly Glu Gly Gly Gly Val Ile
    130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
            180                 185                 190

Ser Ser Val Glu Arg Ala Gly Leu Ile Gly Gly Val Lys Leu Lys Ala
        195                 200                 205

Ile Pro Ser Asp Gly Asn Phe Ala Met Arg Ala Ser Ala Leu Gln Glu
    210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Lys Arg Thr
```

```
                    305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
                340                 345                 350

Leu Gly Arg Arg Phe Arg Ser Leu Lys Met Trp Phe Val Phe Arg Met
                355                 360                 365

Tyr Gly Val Lys Gly Leu Gln Ala Tyr Ile Arg Lys His Val Gln Leu
                370                 375                 380

Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
                420                 425                 430

Ile His Leu Val Pro Cys His Leu Arg Asp Lys Phe Val Leu Arg Phe
                435                 440                 445

Ala Ile Cys Ser Arg Thr Val Glu Ser Ala His Val Gln Arg Ala Trp
450                 455                 460

Glu His Ile Lys Glu Leu Ala Ala Asp Val Leu Arg Ala Glu Arg Glu
465                 470                 475                 480

<210> SEQ ID NO 105
<211> LENGTH: 490
<212> TYPE: PRT
<213> ORGANISM: Homo sapiens
<220> FEATURE:
<221> NAME/KEY: misc_feature
<223> OTHER INFORMATION: TPH2 protein sequence

<400> SEQUENCE: 105

Met Gln Pro Ala Met Met Phe Ser Ser Lys Tyr Trp Ala Arg Arg
1               5                   10                  15

Gly Phe Ser Leu Asp Ser Ala Val Pro Glu Glu His Gln Leu Leu Gly
                20                  25                  30

Ser Ser Thr Leu Asn Lys Pro Asn Ser Gly Lys Asn Asp Asp Lys Gly
                35                  40                  45

Asn Lys Gly Ser Ser Lys Arg Glu Ala Ala Thr Glu Ser Gly Lys Thr
            50                  55                  60

Ala Val Val Phe Ser Leu Lys Asn Glu Val Gly Gly Leu Val Lys Ala
65              70                  75                  80

Leu Arg Leu Phe Gln Glu Lys Arg Val Asn Met Val His Ile Glu Ser
                85                  90                  95

Arg Lys Ser Arg Arg Arg Ser Ser Glu Val Glu Ile Phe Val Asp Cys
                100                 105                 110

Glu Cys Gly Lys Thr Glu Phe Asn Glu Leu Ile Gln Leu Leu Lys Phe
                115                 120                 125

Gln Thr Thr Ile Val Thr Leu Asn Pro Pro Glu Asn Ile Trp Thr Glu
            130                 135                 140

Glu Glu Glu Leu Glu Asp Val Pro Trp Phe Pro Arg Lys Ile Ser Glu
145             150                 155                 160

Leu Asp Lys Cys Ser His Arg Val Leu Met Tyr Gly Ser Glu Leu Asp
                165                 170                 175

Ala Asp His Pro Gly Phe Lys Asp Asn Val Tyr Arg Gln Arg Arg Lys
                180                 185                 190
```

```
Tyr Phe Val Asp Val Ala Met Gly Tyr Lys Tyr Gly Gln Pro Ile Pro
        195             200             205

Arg Val Glu Tyr Thr Glu Glu Thr Lys Thr Trp Gly Val Val Phe
    210             215             220

Arg Glu Leu Ser Lys Leu Tyr Pro Thr His Ala Cys Arg Glu Tyr Leu
225             230             235             240

Lys Asn Phe Pro Leu Leu Thr Lys Tyr Cys Gly Tyr Arg Glu Asp Asn
                245             250             255

Val Pro Gln Leu Glu Asp Val Ser Met Phe Leu Lys Glu Arg Ser Gly
            260             265             270

Phe Thr Val Arg Pro Val Ala Gly Tyr Leu Ser Pro Arg Asp Phe Leu
        275             280             285

Ala Gly Leu Ala Tyr Arg Val Phe His Cys Thr Gln Tyr Ile Arg His
    290             295             300

Gly Ser Asp Pro Leu Tyr Thr Pro Glu Pro Asp Thr Cys His Glu Leu
305             310             315             320

Leu Gly His Val Pro Leu Leu Ala Asp Pro Lys Phe Ala Gln Phe Ser
                325             330             335

Gln Glu Ile Gly Leu Ala Ser Leu Gly Ala Ser Asp Glu Asp Val Gln
            340             345             350

Lys Leu Ala Thr Cys Tyr Phe Phe Thr Ile Glu Phe Gly Leu Cys Lys
        355             360             365

Gln Glu Gly Gln Leu Arg Ala Tyr Gly Ala Gly Leu Leu Ser Ser Ile
    370             375             380

Gly Glu Leu Lys His Ala Leu Ser Asp Lys Ala Cys Val Lys Ala Phe
385             390             395             400

Asp Pro Lys Thr Thr Cys Leu Gln Glu Cys Leu Ile Thr Thr Phe Gln
                405             410             415

Glu Ala Tyr Phe Val Ser Glu Ser Phe Glu Glu Ala Lys Glu Lys Met
            420             425             430

Arg Asp Phe Ala Lys Ser Ile Thr Arg Pro Phe Ser Val Tyr Phe Asn
        435             440             445

Pro Tyr Thr Gln Ser Ile Glu Ile Leu Lys Asp Thr Arg Ser Ile Glu
    450             455             460

Asn Val Val Gln Asp Leu Arg Ser Asp Leu Asn Thr Val Cys Asp Ala
465             470             475             480

Leu Asn Lys Met Asn Gln Tyr Leu Gly Ile
                485             490
```

INHIBITION OF SEROTONIN EXPRESSION IN GUT ENTEROENDOCRINE CELLS RESULTS IN CONVERSION TO INSULIN-POSITIVE CELLS

CROSS-REFERENCE TO RELATED APPLICATIONS

The present application is a national phase application of PCT Application No. PCT/US2015/038186, filed on Jun. 26, 2015, and claims priority to Provisional Appln. 62/017,405, filed Jun. 26, 2014, the entire contents of which are hereby incorporated by reference as if fully set forth herein, under 35 U.S.C. § 119(e).

STATEMENT OF GOVERNMENTAL INTEREST

This invention was made with government support under grants DK058282 and DK057539 awarded by the National Institutes of Health. The Government has certain rights in the invention.

REFERENCE TO SEQUENCE LISTING SUBMITTED VIA EFS-WEB

This application includes an electronically submitted sequence listing in .txt format. The .txt file contains a sequence listing entitled "CU14238_15003267PC0_20161222_ST25.txt" created on Aug. 6, 2015 and is 34 KB in size. The sequence listing contained in this .txt file is part of the specification and is hereby incorporated by reference herein in its entirety.

BACKGROUND OF THE INVENTION

1. Field of the Invention

Methods for treating and preventing types 1 and 2 diabetes.

2. Description of the Related Art

Generation of surrogate sources of insulin-producing β-cells remains a goal of diabetes therapy. While most efforts have been directed at differentiating embryonic or induced pluripotent stem (iPS) cells into β-like-cells through endodermal progenitors, we have shown that gut endocrine progenitor cells of mice can be differentiated into glucose responsive, insulin-producing cells by ablation of transcription factor Foxo1.

Since 1922, lifelong insulin replacement has been the mainstay of type 1 diabetes treatment. Efforts to generate surrogate insulin-producing cells that could serve as a "permanent cure" of the disease have been underway for nearly two decades, and progress has been made toward the generation of pancreatic hormone-producing cells from either embryonic stem or induced pluripotent stem cells (iPS)[1-3]. However, cells thus generated are often polyhormonal, and are characterized by an indifferent response to glucose, unless transplanted into mice, where they acquire undetermined factors required for their functional "maturation"[2,4]. Although terminally differentiated β-cells are only present in the pancreas, endocrine progenitors with similar features to pancreatic endocrine progenitors are also found in the intestine, the site of the body's largest endocrine system[5].

We have shown in previous work that genetic inactivation of Foxo1a in mice in vivo results in the expansion of the enteroendocrine Neurogenin3 (Neurog3)-positive progenitor cell pool, and the appearance of functional insulin-producing cells that express all markers of mature pancreatic β-cells, secrete insulin in response to physiologic and pharmacologic cues, and can readily regenerate to alleviate diabetes caused by the β-cell toxin, streptozotocin[6].

Although there is evidence in mice that enteric and pancreatic endocrine cells can convert into different subtypes[7], possibly through a dedifferentiation process[8-10]. There is still a great need for new long-term regimens for the treatment, prevention, and/or reduction in the risk of developing diabetes or other disorders associated with impaired pancreatic endocrine function.

Before the embodiments of the present invention are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined, otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein, are incorporated by reference in their entirety. Nothing herein is to be construed as an admission that the invention is not entitled to antedate such disclosure by virtue of prior invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present invention is illustrated by way of example, and not by way of limitation, in the figures of the accompanying drawings and in which:

FIG. 1: Survey of FOXO1 expression in human duodenum.

FIG. 2A: Quantitative analysis of the position of FOXO1-positive cells in human duodenum. FIG. 2B-D, FOXO1 immunostaining in (B) jejunum, (C) ileum, (D) colon.

FIG. 3: Marker analysis of 150-day-old human iPS-derived gut organoids.

FIG. 4: Insulin-positive cells in 184-day-old human gut organoids. FIG. 4 I-L, Co-immunohistochemistry with insulin (green) and FOXO1 (red), or (K, L) insulin (green), α-SMA (red) and CDX2 (magenta). Insets in h, j, and l show magnifications of individual cells. DAPI (blue) was used throughout to visualize DNA. Scale bars: 50 μm in a-e; 10 μm in f (n=3-6 for qPCR and 3 for histology) (*p<0.05). Quantitative data is presented as means±SEM.

FIG. 5: Pancreatic lineage marker analysis.

FIG. 6: Changes to enteroendocrine cells following FOXO1 inhibition.

FIG. 8: Human C-peptide assay using 200-day-old human gut organoids and pancreatic islets.

DETAILED DESCRIPTION

1. Definitions

Figure 1A:
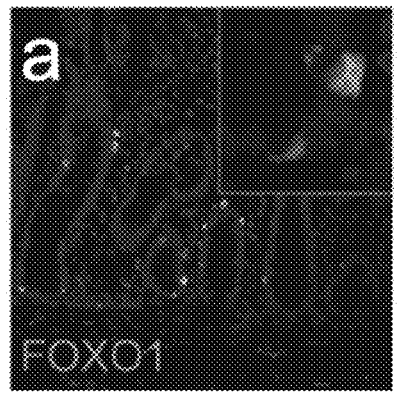
FIG. 1A-E, FOXO1 (red) co-localization with secretory markers, MUCIN2 (MUC2), LYSOXYME (LYS), CHROMOGRANINA (CGA), OLFACTOMEDIN-4 (OLFM4) (all green) and EPHB3 (gray).
Figure 1B:
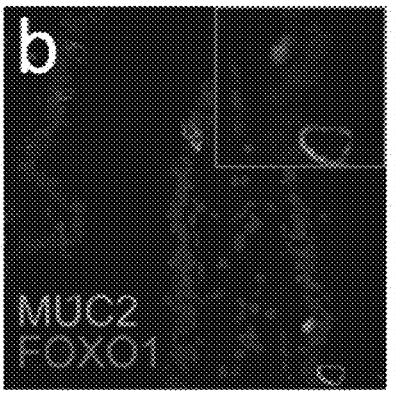
Figure 1C:
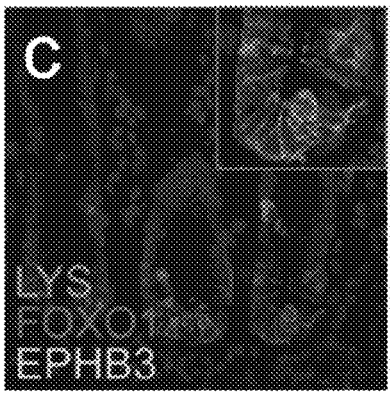
Figure 1D:
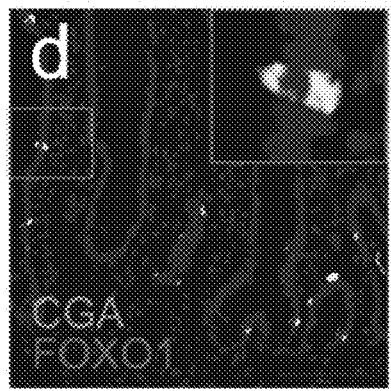
Figure 1E:
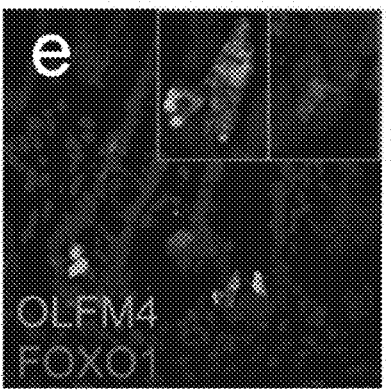
Figure 1F:
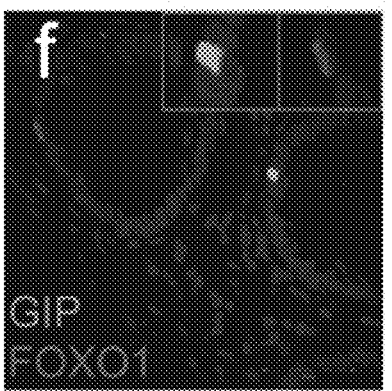
FIG. 1F-L, Co-localization of FOXO1 with endocrine cell markers GIP, somatostatin (SSN), serotonin (5HT), secretin, gastrin, cholecystokinin (CCK), and GLP1. Scale bars: 100 µm in a-e, and 50 µm in f-l (n=3).
Figure 1G:
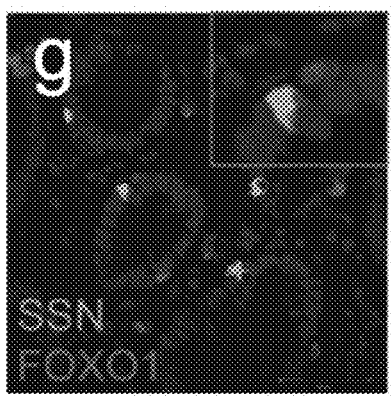

As used herein, the terms "animal," "patient," or "subject" include mammals, e.g., humans, dogs, cows, horses, kangaroos, pigs, sheep, goats, cats, mice, rabbits, rats, and transgenic non-human animals. The preferred animal, patient, or subject is a human.

"An enumerated disease or disorder" and "a disease or disorder characterized by impaired pancreatic endocrine function" are used interchangeably and include inappropriately low insulin levels, diabetes types 1 and 2, metabolic syndrome, obesity, glucose intolerance, hyperglycemia; decreased insulin sensitivity, increased fasting glucose, increased post-prandial glucose, elevated glycohemoglobin A1c. By inappropriately low insulin levels means insulin levels that are low enough to contribute to at least one symptom of the disease or disorder. Impaired pancreatic endocrine function is one in which the pathology is associated with a diminished capacity in a subject for the pancreas to produce and/or secrete insulin and/or an altered capacity (increased or decreased) to secrete pancreatic peptides such as glucagon, pancreatic polypeptide, somatostatin. Disorders associated with impaired pancreatic endocrine function include pathologies sometimes referred to as latent autoimmune diabetes of adulthood, pre-diabetes, impaired fasting glucose, impaired glucose tolerance, fasting hyperglycemia, insulin resistant syndrome, and hyperglycemic conditions.

"Foxo Protein" includes Foxo1, Foxo2, Foxo3 and Foxo4 from mouse; FOXO1, FOXO2, FOXO3 and FOXO4 from human, and Foxo1-4 proteins from any other animal, including variants, and orthologs, and biologically active fragments thereof). FOXO2 was discovered independently but turned out to be the same gene as FOXO3. There are two NM numbers but they point to the same genomic location.

"An active agent" means any agent, polypeptide, nucleic acid, or small molecule that causes any Ins− cell, enteroendocrine cell such as serotonin, Tph1 or somatostatin-expressing cells, or N3 progenitor in the gut to differentiate into an Ins+ cell. Certain active agents are those that reduce the expression, biosynthesis, signaling or biological activity of serotonin or FOXO1, or increase serotonin or FOXO1 degradation biosynthesis or biological activity of serotonin or increase serotonin degradation, or that reduce the expression or biological activity of FOXO1 protein (including by reducing transcription or translation of the gene or mRNA, respectively). Specific active agents that reduce serotonin expression are described below.

The term "pluripotent cell" as used herein refers to a stem cell that has the potential to differentiate into any of the three germ layers: endoderm (interior stomach lining, gastrointestinal tract, the lungs), mesoderm (muscle, bone, blood, urogenital), or ectoderm (epidermal tissues and nervous system). Pluripotent stem cells can give rise to any fetal or adult cell type. Induced pluripotent stem cells are a type of pluripotent stem cells.

The term "multipotent cell" as used herein refers to a cell that has potential to give rise to cells from multiple, but a limited number of lineages.

"Stem cells" means undifferentiated cells that can self-renew for unlimited divisions and differentiate into multiple cell types. Stem cells can be obtained from embryonic, fetal, post-natal, juvenile or adult tissue.

"Progenitor cells" in the gut means cells descended from stem cells that are multipotent, but self-renewal property is limited.

"iPS cells" or "induced pluripotent stem cells" or "inducible pluripotent stem cells" refer to stem cell(s) that are generated from a non-pluripotent cell, e.g., a multipotent cell (for example, mesenchymal stem cell, adult stem cell, hematopoietic cell), a somatic cell (for example, a differentiated somatic cell, e.g., fibroblast), and that have a higher potency than the non-pluripotent cell. iPS may also be capable of differentiation into progenitor cells that can produce progeny that are capable of differentiating into more than one cell type. In one example, iPS cells possess potency for differentiation into endoderm. iPS cells as used herein may pertain to cells that are either pluripotent or multipotent. In one specific example, iPSC cells may be generated from fibroblasts such as according to the teachings of US Patent Publication 20110041857, or as further taught herein.

"Gut organoid" or "gutoid" refers to a group of cells that possess microstructures and cell formation of cells found in the mammalian gut, including human gut. Gut organoids typically possess one or more cell types of mature mammalian gut, including epithelial cells, enteroendocrine progenitors or mature endocrine cells. Gut organoids may express markers of such cell types, including villin (epithelial cell marker), mucin (paneth cell marker), Neurogenin-3 (endocrine progenitor marker), serotonin, Glp-1, Gip and/or CCK.

"Stem cells" means undifferentiated cells that can self-renew for unlimited divisions and differentiate into multiple cell types. Stem cells can be obtained from embryonic, fetal, post-natal, juvenile or adult tissue.

"Progenitor cells" in the gut means cells descended from stem cells that are multipotent, but self-renewal property is limited.

"N3 Enteroendocrine Progenitors" and "N3 Prog" mean a subset of insulin-negative gut progenitor cells expressing neurogenin 3 that give rise to Ins⁻ enteroendocrine cells. It has been discovered that N3 Prog in the gut, hereafter "Gut N3 Prog," have the potential to differentiate into cells that make and secrete biologically active insulin ("Gut Ins⁺ Cells"), but this fate is restricted by Foxo1 during development. Pancreatic N3 Prog differentiate into pancreatic insulin-producing cells during fetal development, but it remains unclear whether there is pancreatic N3 Prog after birth or whether pancreatic N3 Prog can differentiate postnatally into pancreatic hormone-producing cells under normal or disordered conditions. It should be noted here that enteroendocrine (gut) and pancreas N3 Prog have different features, even though they are commonly referred to as N3 cells.

"Noninsulin-producing gut progenitor cells" or "Ins⁻ Gut Prog" broadly means any gut progenitor cell including stem cells and N3 Prog that is capable of differentiating into an insulin producing gut cell (Gut Ins⁺ cell).

"Gut Ins− Cells" broadly means any non-insulin producing cell in the gut. Enteroendocrine cells that do not express insulin are a subset of Gut Ins− cells. Terminally differentiated cells in the gut that do not produce insulin are also gut ins− cells.

"Gut Ins⁺ Cells" broadly means any cell in the gut that has differentiated into an Insulin+ cell in response to contact with an active agent as described herein. Ins+ enteroendocrine cells are a subset of gut ins+ cells as are any Ins+ cell in the gut that have differentiated in response to contact with an active agent as described herein.

"Enteroendocrine cells" means specialized Insulin-negative cells endocrine cells in the gastrointestinal tract, most of which are daughters of N3 Prog cells that no longer produce Neurogenin 3. Enteroendocrine cells (a subset of Gut Ins⁻ cells) produce various other hormones such as gastrin, ghrelin, neuropeptide Y, peptide $YY_{3-36}$ ($PYY_{3-36}$), serotonin, secretin, somatostatin, motilin, cholecystokinin, gastric inhibitory peptide, neurotensin, vasoactive intestinal peptide, glucose-dependent insulinotropic polypeptide (GIP) or glucagon-like peptide-1. Enteroendocrine cells and any other gut insulin-negative cell capable of differentiating into an insulin-positive cell are the targets of the active agents of the invention.

"Insulin-producing enteroendocrine cells" mean any enteroendocrine cells that make and secrete insulin; they are a subset of Gut Ins+ cells. Insulin-producing enteroendocrine cells have the insulin positive phenotype (Ins⁺) so that they express markers of mature beta-cells, and secrete insulin and C-peptide in response to glucose and sulfonylureas. Insulin-producing enteroendocrine cells arise primarily from N3 Prog and also from gut stem cells.

"NKO mice" or "Foxo1 knockout mice" means transgenic mice that do not express Foxo1 in N3 Prog. Not all enteroendocrine cells in the gut of Foxo1 knockout mice (hereafter "NKO mice") make and secrete insulin; some are non-insulin producing (hereafter "Inc").

"Significantly lower" in the context of the present invention means reducing expression, biosynthesis, signaling or biological activity of serotonin or FOXO1 protein or serotonin to a level low enough so that non-insulin-producing enteroendocrine cell or other cell in the gut differentiates to an Ins+ phenotype, including expressing and secreting biologically active insulin. In the context of this invention, a significant reduction in the amount of serotonin or serotonin signaling in enteroendocrine cells is a reduction by about 50%, 70%, 90% or more. In the context of the present invention a significant reduction in FOXO1 expression is a reduction of at least about 50%.

A significantly higher level of insulin in a test sample means detectable by commonly employed assays (such as ELISA or RIA), whereas in the control population insulin cannot be detected by such assays. In the context of determining the level of insulin expression in the control and the test population after contacting with an agent that causes the test population to become insulin-producing cells, significantly higher means any reliably detectable level of insulin since untreated cells are noninsulin-producing. A person of skill in the art of screening assays can define significantly higher or significantly lower depending on the assay.

"Preventing a disease" includes, but is not limited to, preventing or slowing the development of a disease from occurring in a subject that may be predisposed to the disease (or disorder), but has not yet been diagnosed as having the disease, for example by preventing reoccurrence of the disease in a subject where the disease has been relieved or regressed, or ameliorating a pre-disease state that is known to progress into the target disease. An example is reducing blood glucose levels in a hyperglycemic subject (e.g. 100-125 mg/dl), and/or maintaining acceptable control of blood glucose levels in the subject prior to a full diabetic state. Such treatment, prevention, symptoms and/or conditions can be determined by one skilled in the art and are described in standard textbooks.

"Treating" a disease, disorder or condition in a patient refers to taking steps to obtain beneficial or desired results, including clinical results. For purposes of this invention, beneficial or desired clinical results include, but are not limited to reduction, alleviation or amelioration of one or more symptoms of the disease; diminishing the extent of disease; delaying or slowing disease progression; amelioration and palliation or stabilization of the disease state and its complications.

Where the disease is diabetes type 1, symptoms include frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, and excessive or unusual infections. These symptoms are associated with characteristic clinical laboratory findings that include hyperglycemia (excessively elevated sugar concentrations in the blood, i.e. >125 mg/dl), loss of glycemic control (i.e., frequent and excessive swings of blood sugar levels above and below the physiological range, generally maintained between 40-125 mg/dl), fluctuations in postprandial blood glucose, fluctuations in blood glucagon, fluctuations in blood triglycerides and include reduction in rate of or diminution of or improved outcomes of conditions that are accelerated by and/or occur because of or more frequently with diabetes including microvascular and microvascular disease inclusive but not limited to cerebrovascular impairment with or without, stroke, angina, coronary heart disease, myocardial infarction, peripheral vascular disease, nephropathy, kidney impairment, increased proteinuria, retinopathy, neovascularization of vessels in the retina, neuropathy including central, autonomic and peripheral neuropathy that may lead to loss of sensation of extremities and amputation and/or from neuropathy or diminished vascular flow, skin conditions including but not limited to diabetic dermopathy, Necrobiosis Lipoidica Diabeticorum, bullosis diabeticorum, scleroderma diabeticorum, granuloma annulare, bacterial skin infections, but limited to *Staphylococcus*, which can result in deeper infections, and gastoparesis (abnormal emptying of the stomach). Type 1 diabetes may be diagnosed by methods well known to one of ordinary skill in the art. For example, commonly, diabetics have a plasma fasting blood glucose result of greater than 126 mg/dL of glucose. Prediabetes is commonly diagnosed in patients with a blood glucose level between 100 and 125 mg/dL of glucose. Other symptoms may also be used to diagnose diabetes, related diseases and conditions, and diseases and conditions affected by diminished pancreatic endocrine function.

"Pathology associated with impaired pancreatic endocrine function" or pancreatic endocrine malfunction is one in which the pathology is associated with a diminished capacity in a subject for the pancreas to produce and/or secrete one or more pancreatic hormones including insulin and/or pancreatic peptides such as glucagon, pancreatic polypeptide, or somatostatin. Pathologies that are associated with impaired pancreatic endocrine function include type 1 diabetes, and type 2 diabetes. Other pathologies include those sometimes referred to as latent autoimmune diabetes of adulthood, pre-diabetes, impaired fasting glucose, impaired glucose tolerance, fasting hyperglycemia, insulin resistant syndrome, and hyperglycemic conditions.

"Administering" or "administration of" an enumerated active agent or therapeutic pharmaceutical composition to a subject in the methods of the present invention any method known in the art that would facilitate delivery to the gut cells described herein. It includes both direct administration, including self-administration (including oral administration or intravenous, subcutaneous, intramuscular or intraperitoneal injections, rectal administration by way of suppositories), local administration directly into or onto a target tissue (such as a region of the gut that has $Ins^-$ enteroendocrine cells) or administration by any route or method that delivers a therapeutically effective amount of the drug or composition to the gut. Administration includes implanting pumps and matrices comprising the Ins+ cells of the invention.

A "subject" or "patient" is a mammal, typically a human, but optionally a mammalian animal of veterinary importance, including but not limited to horses, cattle, sheep, dogs, and cats.

A "therapeutically effective amount" of an active agent or pharmaceutical composition is an amount that achieves the intended therapeutic effect, e.g., reduction, alleviation, amelioration, palliation or elimination of one or more symptoms or manifestations of the disease or condition in the subject. For diabetes, a therapeutically effective amount can also be an amount that increases insulin secretion, increases insulin sensitivity, increases glucose tolerance, or decreases weight gain, weight loss, or fat mass. The full therapeutic effect does not necessarily occur by administration of one dose and may occur only after administration of a series of doses. Thus, a therapeutically effective amount may be administered in one or more administrations.

A "prophylactically effective amount" of a drug is an amount of a drug that, when administered to a subject, will have the intended prophylactic effect, e.g., preventing or delaying the onset (or reoccurrence) of the disease or symptoms, or reducing the likelihood of the onset (or reoccurrence) of the disease or symptoms. The full prophylactic effect does not necessarily occur by administration of one dose and may occur only after administration of a series of doses. Thus, a prophylactically effective amount may be administered in one or more administrations.

An "effective amount" of an agent is an amount that produces the desired effect.

By "pharmaceutically acceptable," it is meant the carrier, diluent or excipient must be compatible with the other ingredients of the formulation and not deleterious to the recipient thereof.

"Foxo Gene" or "serotonin pathway gene" means any gene encoding a Foxo protein or genes required for serotonin synthesis, signaling, and degradation, respectively, including orthologs, and biologically active fragments thereof.

"Foxo mRNA" and "serotonin pathway mRNA" means any mRNA encoding a Foxo protein or proteins required for serotonin synthesis, signaling, and degradation, respectively, including orthologs, and biologically active fragments thereof.

An "antagonist of a serotonin receptor," as used herein, refers to a substance which reduces the biological action or effect of signaling through the serotonin receptor. Serotonin receptor antagonists for use in the invention are those reduce serotonin signaling and its biological actions on enteroendocrine cells thereby mimicking the effect of inhibiting serotonin production.

5HTr2b Antagonists Include:

RS-127445 specific 5HTr2b antagonists, Terguride is a potent 5-HTR2A/2B antagonist [R. Dumitrascu et al., Eur Respir J 2011; 37: 1104-1118], Sarpogrelate: a mixed 5-HT2A/B antagonist, Lisuride: a dopamine agonist of the of the ergoline class, that is also a 5-HT2B antagonist, Tegaserod: primarily a 5-HT4 agonist, but also a 5-HT2B antagonist, RS-127,445:high affinity; subtype selective (1000×), selective over at least eight other 5-HTR types; orally bioavailable, SDZ SER-082: a mixed 5-HT2B/C antagonist, SB-215,505, SB-228,357, LY-266,097, EGIS-7625: high selectivity over 5-HT2A, PRX-08066, SB-200, 646, SB-204,741, SB-206,553: mixed 5-HT2B/C antagonist and PAM at a7 nAChR and LY-272,015.

5HTr1a Antagonists Include:

Alprenolol, AV-965, BMY-7,378, Cyanopindolol, Dotarizine, Flopropione, GR-46,611, Iodocyanopindolol, Isamoltane, Lecozotan, Methiothepin, Methysergide, MPPF, NAN-190, Oxprenolol, Pindobind, Pindolol, Propranolol, Risperidone, Robalzotan, SB-649,915, SDZ-216,525, Spiperone, Spiramide, Spiroxatrine, UH-301, WAY-100,135, WAY-100,635, Xylamidine and Mefway.

"Gut organoid" or "gutoid" refers to a group of cells that possess microstructures and cell formation of cells found in the mammalian gut, including human gut. Gut organoids typically possess one or more cell types of mature mammalian gut, including epithelial cells, enteroendocrine progenitors or mature endocrine cells. Gut organoids may express markers of such cell types, including villin (epithelial cell marker), mucin (paneth cell marker), Neurogenin-3 (endocrine progenitor marker), serotonin, Glp-1, Gip and/or CCK.

Generation of surrogate sources of insulin-producing β-cells remains a goal of diabetes therapy. While most efforts have been directed at differentiating embryonic or induced pluripotent stem (iPS) cells into β-like-cells through endodermal progenitors, it is known that gut endocrine progenitor cells in mice can differentiate into glucose-responsive, insulin-producing cells by reducing or ablating transcription factor Foxo1. It is now discovered that FOXO1 colocalizes with serotonin in certain human gut non-insulin-producing endocrine cells. Using gut organoids derived from human iPS cells, it was shown that FOXO1 inhibition using a dominant-negative mutant or lentivirus-encoded shRNA promoted generation of insulin-positive cells that express all markers of mature pancreatic β-cells, release C-peptide in response to secretagogues, and survive in vivo following transplantation into mice. It has further been discovered that inhibition or ablation of FOXO1 in human enteroendocrine cells in the gut coincides with a significant reduction of about ~60% in number of serotonin-expressing enteroendocrine progenitor cells. While FOXO+ cells that underwent conversion to insulin+ cells did not express 5HT, it was also observed that FOXO+ cells that continue to express 5HT did not convert to insulin+ cells.

Based on these observations, certain embodiments of the present invention are directed to methods for treating a disorder associated with impaired endocrine pancreatic function in a subject by administering a therapeutically effective amount of an active agent that reduces the expression, biosynthesis, signaling or biological activity of serotonin or increases its degradation, either alone or as a combination therapy with an active agent that reduces FOXO1 expression or biological activity, wherein administering comprises delivering the agent or agents to Gut Ins– cells including enteroendocrine cells or other non-insulin-producing gut cell in the mammal, preferably a human. The active agent causes the Gut Ins– cells to differentiate into glucose-responsive (Gut Ins+ cells) enteroendocrine cells that make and secrete biologically active insulin. The therapeutically effective amount is an amount that reduces one or more symptoms of the disorder.

Other embodiments are described below and in the claims.

2. Overview

Transcription factor Foxo1 expression (a structural and functional ortholog of human FOXO1, 3 and/or 4) regulates multiple aspects of pancreatic beta-cell function (4) and is widely expressed in Neurog3+ pancreatic endocrine progenitors (5). Foxo1 is also expressed in most Neurog3+ enteroendocrine progenitors (EEP), whereas in the adult mouse it is localized to a subset of cells that, based on morphology and localization, include secretory cells, endocrine and stem cells throughout the gut. Enteroendocrine cells are sub-set of secretory cells. There are 3 secretory cell types: goblet, Paneth, and enteroendocrine cells. Goblet and Paneth cells do not normally produce hormones. FOXO1-producing Neurogenin 3+ enteroendocrine progenitors (N3 Prog) under normal conditions differentiate into enteric hormone-positive daughter cells that produce neither N3 nor insulin (they are Ins–). The enteroendocrine system is comprised of many different cell types, some of which are shared in common with the endocrine pancreas (e.g., somatostatin- and ghrelin-producing cells), and some of which are organ-specific[5].

Much is known in mice about the consequences of genetic inactivation of Foxo1a[6], however, in contrast to the mouse, little is known about the effect of FOXO1 on endocrine differentiation in human gut, especially whether FOXO1 loss-of-function can alter the fate of enteroendocrine cells toward the insulin-producing lineage[11]. It is now shown that FOXO1 inhibition in vitro in human gut enteroendocrine cells in organoid cultures caused their conversion into insulin-positive cells that express markers of mature pancreatic β-cells and secrete C-peptide in response to glucose, arginine, and KCl.

It has further been discovered that inhibition of FOXO1 in human gut enteroendocrine cells that express serotonin coincides with a dramatic reduction of about 60% in the number of serotonin-expressing cells. This reduction of serotonin-positive cells is therefore associated with the appearance of the insulin-positive phenotype. In a study described below FOXO1 inhibition correlated positively with an increase in expression of the 5HTr2b receptor, which increase is compensatory resulting from the reduction in serotonin expression. Therefore contacting an enteroendocrine cells with a 5HTr2b antagonist would reduce serotonin signaling and its biological actions, mimicking the effect of inhibiting serotonin production. Based on these observations and others described herein and in the attached appendices, certain embodiments of the invention are directed to:

(1) Human gut organoid cultures comprising Gut Ins+ cells including enteroendocrine cells or other gut cells that make and secrete biologically active insulin, which Gut Ins+ cells are produced by contacting gut organoid cultures with an active agent(s) as described herein in an amount that reduces the expression, biosynthesis, biological activity or amount of serotonin in the insulin-negative cells or that increases serotonin degradation thereby causing the cells to differentiate into Gut Ins+ cells. In other embodiments Gut Ins+ cells are produced by contacting insulin-negative cells in the cultures with both an agent that that reduces the expression 5HTsynthesis/degradation related genes, biosynthesis, biological activity or amount of serotonin in the cells or that increases serotonin degradation and an agent such as an inhibitory oligonucleotides that block expression of FOXO1 protein in amounts that cause the cells to differentiate into Gut Ins+ cells. In certain embodiments the amount of active agent reduces 5-HT biosynthesis by at least about 50%, 70%, 90% or more. Use of inhibitory oligonucleotides is preferable to using viral vectors to inhibit expression of targeted genes. In certain embodiments FOXO1 expression is reduced by at least about 50%.

(2) Isolated human Gut Ins+ cells comprising enteroendocrine cells or gut cells that make and secrete biologically active insulin, isolated from the human gut organoid cultures of (1).

(3) Methods of treating type 1 and type 2 diabetes and other of the enumerated disorders associated with impaired pancreatic function in a subject, by administering, delivering or implanting in a subject, a therapeutically effective amount of the isolated human Gut Ins+ cells that make and secrete biologically active insulin of (2). The therapeutically effective amount is an amount that reduces one or more symptoms of the disorder. In certain other embodiments the administered cells are autologous to the subject. The Gut Ins+ cells can be implanted in the gut of the subject or in a device (similar to an Ommaya reservoir) that can deliver insulin to the body on specific cues. Such device could be implanted under the skin in any location throughout the body, or could be connected to the body by way of a small catheter or infusion needle. In other embodiments the cells are implanted in a scaffold or other matrix to facilitate delivery. Other variations are described below.

(4) A method for treating a disease or disorder in a mammal, preferably a human, associated with impaired pancreatic endocrine function, by administering a therapeutically effective amount of an enumerated active agent that reduces the expression, biosynthesis, signaling or biological activity of serotonin or increases its degradation, wherein administering comprises delivering the agent to Gut Ins– cells in the mammal. The active agent causes the cells to differentiate into Gut-Ins+ glucose-responsive cells that make and secrete insulin. The therapeutically effective amount is an amount that reduces one or more symptoms of the disorder. Other embodiments of the method are directed to combination therapy wherein an agent that significantly reduces FOXO1 expression, biosynthesis, signaling or biological activity or increases its degradation is administered in addition to the agent that reduces serotonin.

(5) A method for treating a disease or disorder in a mammal, preferably a human, associated with impaired pancreatic endocrine function, by administering a therapeutically effective amount of an enumerated active agent that reduces the expression, biosynthesis, signaling or biological activity of Foxo protein (typically Foxo1), wherein administering comprises delivering the agent to Gut Ins– cells in the mammal that are serotonin positive. The active agent causes the cells to differentiate into Gut-Ins+(typically glucose-responsive) cells that make and secrete insulin. The therapeutically effective amount is an amount that reduces one or more symptoms of the disorder.

Agents that reduce FOXO1 expression include isolated small hairpin RNA (shRNA), small interfering RNA (siRNA), antisense RNA, antisense DNA, chimeric antisense DNA/RNA, microRNA, and ribozymes that are sufficiently complementary to specifically bind to a gene or mRNA encoding either FOXO1, to reduce expression. A significant reduction in FOXO1 is a reduction of about 50% or more. Agents that reduce sertotonin production in gut cells include isolated small hairpin RNA (shRNA), small interfering RNA (siRNA), antisense RNA, antisense DNA, chimeric antisense DNA/RNA, microRNA, and ribozymes that are sufficiently complementary to specifically bind to a gene or mRNA encoding involved in 5HT synthesis, to reduce expression. A significant reduction in expression is a reduction of about 50% or more. Enzymes involved in 5HT synthesis include tryptophan hydrolase (1 and/or 2) and L-aromatic amino acid decarboxylase and monoamine oxidase (A and/or B) is involved in 5HT degradation.

(6) A method for making insulin-positive gut cells that make and secrete biologically active insulin (Gut Ins+ cells), by a) obtaining a human gut cell culture (typically a gut organoid culture) comprising insulin-negative cells (Gut Ins– cells) comprising enteroendocrine cells (optionally serotonin-positive) or other gut insulin-negative cell, and b) contacting the insulin-negative cells in the gut (Gut Ins– cells) in the cell culture with: (i) an agent that reduces expression, biosynthesis, signaling or biological activity of serotonin or increases serotonin degradation in an amount and under conditions that permit a significant portion of the insulin-negative cells to differentiate into insulin-positive cells that make and secrete biologically active insulin (Gut Ins+ cells), and/or (ii) an agent that reduces the expression or biological activity of forkhead box O1 (Foxo1) protein or biologically active fragments thereof, in an amount and under conditions that permit a significant portion of the insulin-negative cells to differentiate into insulin-positive cells that make and secrete biologically active insulin (Gut Ins+ cells).

4. Detailed Description of Embodiments

A. Antisense Nucleotides and siRNA

Other embodiments of the present invention are directed to the use of antisense nucleic acids or small interfering RNA (siRNA) or shRNA to reduce or inhibit expression and hence the biological activity of FOXO1 or enzyme in the serotonin biosynthetic pathway. Based on these known sequences of these proteins and genes encoding them, antisense DNA or RNA that are sufficiently complementary to the respective gene or mRNA to turn off or reduce expression can be readily designed and engineered, using methods known in the art. In a specific embodiment of the invention, antisense or siRNA molecules for use in the present invention are those that bind under stringent conditions to the targeted mRNA or targeted gene identified by the Genbank numbers, or to variants or fragments that are substantially homologous to the mRNA or gene encoding FOXO1 or serotonin biosynthetic enzyme. The antisense compounds of the invention are synthesized in vitro and do not include antisense compositions of biological origin.

Methods of making antisense nucleic acids are well known in the art. As used herein, the terms "target nucleic acid" encompass DNA encoding the target proteins and RNA (including pre-mRNA and mRNA) transcribed from such DNA. The specific hybridization of a nucleic acid oligomeric compound with its target nucleic acid interferes with the normal function of the target nucleic acid. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulating or reducing the expression of the protein encoded by the DNA or RNA. In the context of the present invention, "modulation" means reducing or inhibiting in the expression of the gene or mRNA for one or more of the targeted proteins.

The targeting process includes determination of a site or sites within the target DNA or RNA encoding the targeted protein for the antisense interaction to occur such that the desired inhibitory effect is achieved. Within the context of the present invention, a preferred intragenic site is the region encompassing the translation initiation or termination codon of the open reading frame (ORF) of the mRNA for the targeted proteins. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. Routine experimentation will determine the optimal sequence of the antisense or siRNA It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, nucleic acids are chosen which are sufficiently complementary to the target; meaning that the nucleic acids will hybridize sufficiently well and with sufficient specificity, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of function, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e., from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression. Nucleic acids in the context of this invention include "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Antisense nucleic acids have been employed as therapeutic moieties in the treatment of disease states in animals and man. Antisense nucleic acid drugs, including ribozymes, have been safely and effectively administered to humans and numerous clinical trials are presently underway. It is thus established that nucleic acids can be useful therapeutic modalities that can be configured to be useful in treatment regimes for treatment of cells, tissues and animals, especially humans, for example to down-regulate expression of one or more Foxo proteins or enzymes involved in the serotonin synthesis or degradation pathway.

The antisense and siRNA compounds of the present invention can be utilized for diagnostics, therapeutics, and prophylaxis and as research reagents and kits. For therapeutics, an animal, preferably a human, suspected of having a disease or disorder such as diabetes, metabolic syndrome, glucose intolerance, and/or obesity where there is an inappropriately low level of insulin, which can be treated by reducing the expression of one or more Foxo proteins or enzymes involved in the serotonin synthesis or degradation pathway, is treated by administering antisense compounds in accordance with this invention. The compounds of the invention can be utilized in pharmaceutical compositions by adding an effective amount of an antisense compound to a suitable pharmaceutically acceptable diluent or carrier. The antisense compounds and methods of the invention are useful prophylactically, e.g., to prevent or delay the appearance of diabetes, glucose intolerance, metabolic syndrome or obesity. The antisense compounds and methods of the invention are also useful to retard the progression of metabolic syndrome, glucose intolerance, diabetes, atherosclerosis or obesity.

The present invention also includes pharmaceutical compositions and formulations which include the antisense compounds described herein.

US Patent Application 2004/0023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001). Interference of gene expression by these small interfering RNA (siRNA) is now recognized as a naturally occurring strategy for silencing genes in *C. elegans, Drosophila*, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

In mammalian cell culture, a siRNA-mediated reduction in gene expression has been accomplished by transfecting cells with synthetic RNA nucleic acids (Caplan et al., 2001; Elbashir et al., 2001). The 2004/0023390 application, the entire contents of which are hereby incorporated by reference as if fully set forth herein, provides exemplary methods using a viral vector containing an expression cassette containing a pol II promoter operably-linked to a nucleic acid sequence encoding a small interfering RNA molecule (siRNA) targeted against a gene of interest.

As used herein RNAi is the process of RNA interference. A typical mRNA produces approximately 5,000 copies of a protein. RNAi is a process that interferes with or significantly reduces the number of protein copies made by an mRNA. For example, a double-stranded short interfering RNA (siRNA) molecule is engineered to complement and match the protein-encoding nucleotide sequence of the target mRNA to be interfered with. Following intracellular delivery, the siRNA molecule associates with an RNA-induced silencing complex (RISC). The siRNA-associated RISC binds the target through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 19 to about 29 nucleotide siRNAs to mediate gene-specific suppression in mammalian cells has apparently overcome this obstacle. These siRNAs are long enough to cause gene suppression.

Certain embodiments of the invention are directed to the use of shRNA, antisense or siRNA to block expression of the targeted protein or orthologs, analogs and variants thereof in an animal. The antisense compounds of the invention are synthesized in vitro and do not include antisense compositions of biological origin, or genetic vector constructs designed to direct the in vivo synthesis of antisense molecules.

There are tested delivery methods to achieve in vivo transfection such as coating siRNA with liposomes or nanoparticles. There is also a novel technology that specifically targets siRNA delivery to gut epithelium, called "Transkingdom RNA interference." The inventors of this technique have genetically engineered non-pathogenic *E. Coli* bacteria that are able to produce short hairpin RNA (shRNA) targeting a mammalian gene (Xiang, S., et al., 2009. In vitro and in vivo gene silencing by TransKingdom RNAi (tkRNAi). *Methods Mol Biol* 487:147-160). Two factors were used to facilitate shRNA transfer: the invasin (Inv) and listeriolysin O (HlyA) genes. They have shown that the recombinant *E. coli* can be administered orally to deliver an shRNA against Catenin b1 (Ctnnb 1) that inhibits expression of this gene in intestinal epithelial cells without demonstrable systemic complications from leaking of bacteria into the bloodstream. Certain embodiments of the invention are directed to using the Transkingdom RNA interference method adapted to siRNA that silences one or more targeted proteins.

Others have used this technique to knock down Abcb1 (Kruhn, A., et al., 2009. Delivery of short hairpin RNAs by transkingdom RNA interference modulates the classical ABCB1-mediated multidrug-resistant phenotype of cancer cells. *Cell Cycle* 8).

Bacteria encoding the shRNA can be purchased from Cequent Technologies, and can be administered inter alia it by oral gavage at the recommended concentrations. Doses can be determined using analysis of Foxo1 knock-down in intestinal cells in biopsies, for example or in test animals.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

The antisense nucleic acid molecules of the invention are typically administered to a subject or generated in situ such that they hybridize sufficiently with or bind to cellular mRNA and/or genomic DNA encoding the protein of interest to thereby reduce expression of the protein, e.g., by reducing transcription and/or translation. The hybridization can be by conventional nucleotide complementary to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an alpha-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330). All of the methods described in the above articles regarding antisense technology are incorporated herein by reference.

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave targeted mRNA transcripts thereby inhibiting translation. A ribozyme having specificity for a targeted-encoding nucleic acid can be designed based upon the nucleotide sequence of its cDNA. For example, a derivative of a Tetrahymena L-19 IVS RNA can be constructed in which the nucleotide sequence of the active site is complementary to the nucleotide sequence to be cleaved in the targeted mRNA. See, e.g., Cech et al. U.S. Pat. No. 4,987,071; and Cech et al. U.S. Pat. No. 5,116,742. Alternatively, a targeted FOXO mRNA can be used to select a catalytic RNA having a specific ribonuclease activity from a pool of RNA molecules. See, e.g., Bartel and Szostak (1993) Science 261:1411-1418, incorporated herein by reference.

As used herein, the term "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that flank an ARPKD gene). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

As used herein, a "therapeutically effective amount" of the siRNA is an amount sufficient to cause RNAi-mediated degradation of the target mRNA, or an amount sufficient to inhibit the progression of an enumerated disease in a subject or to change the phenotype of an Insulin⁻ N3 Prog or Ins− enteroendocrine cell to an Ins+ cell.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Antisense molecules that bind to a reduce expression of FOXO1 include, but are not limited to, those taught in U.S. Pat. No. 7,807,649, Ropelle et al., Journal of Physiology, 2009 587:2341-2351, Samuel et al, Diabetes. 2006 July; 55(7):2042-50 and US Patent Publication 20130216554. The teachings of these applications as they relate to FOXO1 antisense are incorporated herein.

siRNA molecules that reduce expression of FOXO1 include, but are not limited to, those taught in Daly et al. Genes & Dev. 2004. 18:1060-1071; Behl et al., Diabetes. 2009 April; 58(4):917-25; Potente et al. *J Clin Invest.* 2005; 115(9):2382-2392; Goto et al., British Journal of Cancer (2008) 98, 1068-1075; Alikani et al., 2005 The Journal of Biological Chemistry, 280,12096-12102; Siqueira et al. Bone. 2011 May 1; 48(5): 1043-1051; Samarin et al. Feb. 12, 2010 The Journal of Biological Chemistry, 285, 4328-4336; Tanaka et al. Journal of Investigative Dermatology Symposium Proceedings (2009) 14, 60-62; Hribal, J Cell Biol. 2003 Aug 18; 162(4): 535-541; and US Patent Publication 20130216554. Other siRNA molecules includes those commercially available by Santa Cruz Biotechnology, Cell Signaling Technology (e.g. Product no. 6242 and Life Technologies (e.g. Product nos. 106652, 106653, 106654).

shRNA molecules targeting FOXO1 include, but are not limited to, those taught in US Patent Pub 20130216554, and commercially available from Sigma Aldrich (for example, product nos SH 1911, SH1921, and SH1931; and TRC Nos TRCN0000039580; TRCN0000039582; TRCN0000010333).

Further, it is known that certain transcription factors such as Nkx2.2, Fev1 and Lmx1 control genes associated with 5HT synthesis and degradation. Blocking expression of these transcription factors is an alternate method of reducing 5HT synthesis in enteroendocrine cells. Oligonucleotide inhibitors such as antisense, siRNA and shRNA or antibodies targeting these transcription factors in enteroendocrine may utilized to reduce expression of TPH and AAAD. Human Nkx2.2 gene is provided as NCBI Reference Sequence: NG_042186.1. Human Nkx2.2 antisense strand is provided as Genbank Accession No. AI675189. siRNA molecules targeting Nkx2.2 for use in accord with the teachings herein are commercially available (e.g. Life Technologies, product nos. 143628, 41684, 41765,41833, and Santa Cruz Biotechnology cat. No. sc-38723).

Human Fey sequence is provided as NCBI Reference Sequence: NG_023323.1. Antisense molecules that target and bind to this gene are clearly envisionable based on the known genetic sequence and are straightforward to make based on known techniques. siRNA and shRNA molecules targeting Fey for use in accord with the teachings herein are commercially available (e.g. Santa Cruz Biotechnology, sc-37859, sc-37859-SH). Lmx is another transcription factor associated with 5HT biosynthesis. The mRNA sequence of human Lmx1A is found at NCBI Reference Sequence: NM_177398.3. Antisense molecules that target and bind to this gene are clearly envisionable based on the known genetic sequence and are straightforward to make based on known techniques. siRNA and shRNA molecules targeting Lmx1 for use in accord with the teachings herein are commercially available (e.g. Santa Cruz Biotechnology, product nos sc-38721, sc-38721-SH (Lmx1B), sc-72343, sc-72343-SH (Lmx1A).

TH tyrosine hydroxylase (also known as TYH; DYT14; DYT5b) [*Homo sapiens*]: Gene ID: 7054; Species Human.Entrez 7054; RefSeq (mRNA)NM_000360; RefSeq (protein) NP_000351; Location (UCSC) Chr 11:

NCBI GenBank AF057280=*Homo sapiens* tryptophan hydroxylase (TPH) gene, alternative splice products, partial cds.DNA linear; Accession No. NG_011947 (Genbank TPH1) Accession No. NG_008279 (Genbank TPH2). TPH1 protein sequence (SEQ ID No. 103)

```
MIEDNKENKDHSLERGRASLIFSLKNEVGGLIKALKIFQEKHVNLLHIES

RKSKRRNSEFEIFVDCDINREQLNDIFHLLKSHTNVLSVNLPDNFTLKED

GMETVPWFPKKISDLDHCANRVLMYGSELDADHPGFKDNVYRKRRKYFAD

LAMNYKHGDPIPKVEFTEEEIKTWGTVFQELNKLYPTHACREYLKNLPLL

SKYCGYREDNIPQLEDVSNFLKERTGFSIRPVAGYLSPRDFLSGLAFRVF

HCTQYVRHSSDPFYTPEPDTCHELLGHVPLLAEPSFAQFSQEIGLASLGA

SEEAVQKLATCYFFTVEFGLCKQDGQLRVFGAGLLSSISELKHALSGHAK

VKPFDPKITCKQECLITTFQDVYFVSESFEDAKEKMREFTKTIKRPFGVK

YNPYTRSIQILKDTKSITSAMNELQHDLDVVSDALAKVSRKPSI
```

TPH2 protein sequence is as follows:

```
  1 mqpammmfss kywarrgfsl dsavpeehql lgsstlnkpn sgknddkgnk gsskreaate 61 sgktavvfsl knevgglvka lrlfqekrvn mvhiesrksr rrsseveify dcecgktefn 121 eliqllkfqt tivtlnppen iwteeeeled vpwfprkise ldkcshrvlm ygseldadhp 181 gfkdnvyrqr rkyfvdvamg ykygqpipry eyteeetktw gvvfrelskl ypthacreyl 241 knfplltkyc gyrednvpql edvsmflker sgftvrpvag ylsprdflag layrvfhctq 301 yirhgsdply tpepdtchel lghvplladp kfaqfsqeig laslgasded vqklatcyff
```

```
361  tiefglckqe gqlraygagl lssigelkha lsdkacvkaf dpkttclqec littfqeayf 421  vsesfeeake kmrdfaksit rpfsvyfnpy tqsieilkdt rsienvvqdl rsdlntvcda 481  lnkmnqylgi
```

NCBI GenBank M88070=Human aromatic L-amino acid decarboxylase gene, exon 1; synonyms=dopa decarboxylase, tryptophan decarboxylase, aromatic 1-amino acid decarboxylase, and hydroxytryptophan decarboxylase, Also, Accession no. NG_008742 (Genbank DDC). L-aromatic amino acid decarboxylase protein sequence (SEQ ID No. 104).

```
MNASEFRRRGKEMVDYVANYMEGIEGRQVYPDVEPGYLRPLIPAAAPQEP

DTFEDIINDVEKIIMPGVTHWHSPYFFAYFPTASSYPAMLADMLCGAIGC

IGFSWAASPACTELETVMMDWLGKMLELPKAFLNEKAGEGGGVIQGSASE

ATLVALLAARTKVIHRLQAASPELTQAAIMEKLVAYSSDQAHSSVERAGL

IGGVKLKAIPSDGNFAMRASALQEALERDKAAGLIPFFMVATLGTTTCCS

FDNLLEVGPICNKEDIWLHVDAAYAGSAFICPEFRHLLNGVEFADSFNFN

PHKWLLVNFDCSAMWVKKRTDLTGAFRLDPTYLKHSHQDSGLITDYRHWQ

IPLGRRFRSLKMWFVFRMYGVKGLQAYIRKHVQLSHEFESLVRQDPRFEI

CVEVILGLVCFRLKGSNKVNEALLQRINSAKKIHLVPCHLRDKFVLRFAI

CSRTVESAHVQRAWEHIKELAADVLRAERE
```

These TPH and AAD protein sequences and nucleotide sequences encoding same are relevant and useful for designing oligonucleotide inhibitors that will reduce expression of these enzymes.

siRNA targeting TPH is commercially available (e.g. Santa Cruz Biotechnology, sc-41526 (TPH1), sc-61700 (TPH2)). shRNA is provided as sc-61700-SH. siRNA targeting AAAD is commercially available (e.g. Santa Cruz Biotechnology, sc-60516). shRNA is provided as sc-60516-SH.

Gene information related to Foxo are provided herein below.

B. Antibodies

As an alternative to oligonucleotide or small molecule based inhibitors, antibodies (including portions or fragments or variants of antibody fragments or variants of antibodies) targeting a FOXO protein or proteins involved in 5HT synthesis or degradation, or transcription factors involved in 5HT synthesis may be used to reduce expression or activity of the relevant target. In the case of binding to transcription factors, antibodies can result in reducing expression of the target protein.

An "antibody" refers to an intact immunoglobulin or to an antigen-binding portion (fragment) thereof that competes with the intact antibody for specific binding, and is meant to include bioactive antibody fragments. Therapeutically useful antibodies in treating or preventing an enumerated disease or changing a phenotype as described include any antibody to any FOXO protein or analog, ortholog or variant thereof, preferably FOXO1, proteins involved in 5HT biosynthesis, and transcription factors involved in 5HT biosynthesis.

Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992).

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for the polypeptide of interest can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

An "isolated antibody" is an antibody that (1) is not associated with naturally-associated components, including other naturally-associated antibodies, that accompany it in its native state, (2) is free of other proteins from the same species, (21) is expressed by a cell from a different species, or (4) does not occur in nature.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293, incorporated herein by reference.

The term "chimeric antibody" refers to an antibody that contains one or more regions from one antibody and one or more regions from one or more other antibodies.

Fragments, portions or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

Human anti-Foxo1 antibodies are commercially available (e.g. Thermo Scientific Pierce Antibodies, cat no. MA1-23230 and Novus Biologicals cat no. NBP2-31376). Human anti-Tph antibodies are commercially available (e.g. Abcam, product no. ab46757). Human anti-L-aromatic amino acid decarboxylase antibodies are commercially available (e.g. Abcam product no. ab3905).

Human anti-NKX2.2 antibody is commercially available (e.g. Abcam product no. ab86024). anti-FEV antibody commercially available (e.g. Santa Cruz Biotechnology, cat. No. sc-6530). Anti-Lmx1 antibodies are commercially available (e.g. Santa Cruz Biotechnology, product nos sc-54273 (Lmx1A), sc-54274 (Lmx1A), sc-134990 (Lmx1A), sc-21231 (Lmx1B), sc-133745 (Lmx1B).

Human anti-TPH antibody is commercially available (e.g. ABM, cat nos. Y060271 and Y060182). Human anti-AAAD antibody is commercially available (e.g. Abcam, ab3905).

C. Small Molecule Inhibitors of Serotonin Biosynthesis

Agents that reduce serotonin biosynthesis include any agent that inhibits an enzyme including tryptophan hydroxylase (TPH, there is TPH1 and TPH2, EC no. 1.14.16.4), and L-aromatic amino acid decarboxylase (AAAD, EC no. 4.1.1.28). Inhibitors of serotonin biosynthesis include oligonucleotides that inhibit expression of an enzyme in the serotonin biosynthetic pathway, as well as the TPH inhibitors such as p-Chlorophenylalanine, p-Ethynlphenylalanine, α-Propyldpacetamide, 6-Flurotyptophan, pChloroamphetamine, Fenfluramine, LP-533401. 1×1031, 5 hydroxytryptophan inhibitor L-phenylalanine; and peripheral AAAD inhibitors such as MK-486, brocresine, carbidopa, 3-hydroxybenzylhydrazine, α-methyldopa, and benserazide.

Agents that increase serotonin degradation include any agent that increases the activity or expression of an enzyme in the serotonin degradation pathway including monoamine oxidase and ALDH1a3. Inhibitors of monoamine oxidase A include, but are note limited to, clorgyline, harmaline, moclobemide, brofaromine toloxatone, M30 dihydrochloride, rasagiline, and befloxatone. Inhibitors of aldehyde dehydrogenase include disulfiram, cyanamide, daidzein, genistin, propioladehyde, phenethyl isothiocyanate, methylene blue. Analogs of monoamine oxidase and ALDH1a3 also have therapeutic utility. Androgen dihydrotestosterone (DHT) caused a 4-fold increase in ALDH1A3 mRNA levels in human prostate. Trasino S E et al.; Exp Biol Med (Maywood). 2007 June; 232(6):762-71.

Agents that reduce serotonin signaling include antagonists that bind to serotonin receptors 5HTr2b or 5HTr1a, or both, on the surface of gut enteroendocrine serotonin-producing cell. In certain embodiments, binding of the antagonists causes a significant reduction of at least about 50%, 70%, 90% or more in serotonin signaling. Contacting non-insulin-producing gut cells with the antagonist would reduce serotonin signaling and its biological actions, mimicking the effect of inhibiting serotonin production.

Evidence of the insulin-producing gut enteroendocrine cells in the subject can be obtained by determining an increase in circulating insulin the in subject, glucose tolerance testing, c-peptide, proinsulin or by determining improvement in the symptoms of the enumerated disorders, including a reduction in the amount of exogenous insulin delivered by injection or through a subcutaneous continuous insulin infusion ("Insulin pump").

Figure 10:
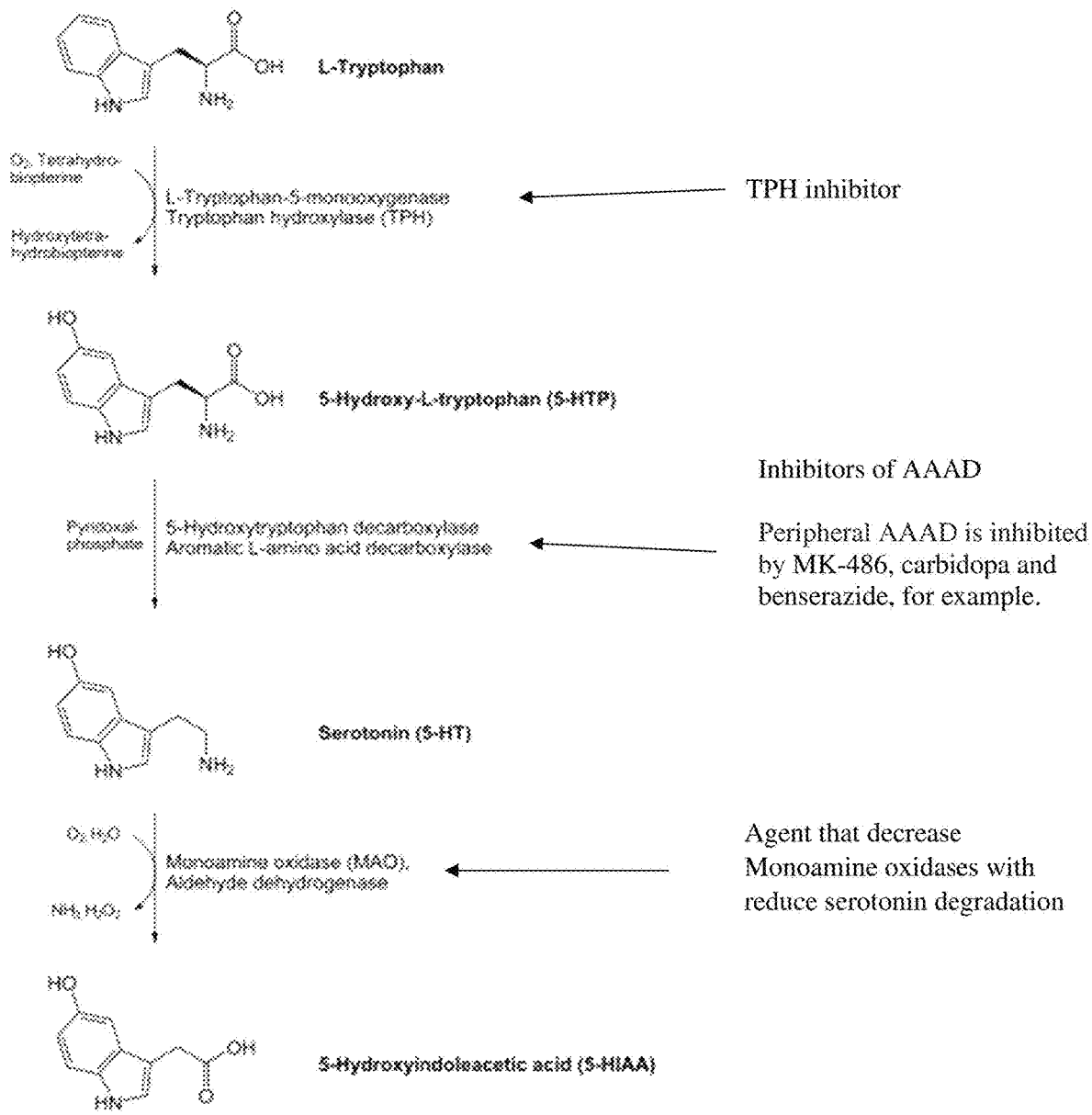
FIG. 10 provides a diagram showing the synthetic pathway of Serotonin.

Provided in FIG. 10 is a diagram showing the synthetic pathway of Serotonin. In most cases, unless stated otherwise, discussion on enzymes that are involved in "biosynthesis of serotonin," "synthesis of serotonin," "serotonin biosynthesis pathway." or "synthetic pathway of serotonin" is intended to also involve enzymes involved in degradation of serotonin.

D. Pharmaceutical Compositions

Certain embodiments of the present invention are directed to pharmaceutical compositions and formulations that include one or more active agents as defined herein, including but not limited to small molecules, polypeptides, inhibitory oligonucleotides (including antisense RNA, siRNA, microRNAs, and ribozymes that reduce the expression and/or biological activity of FOXO1 proteins or of enzymes in the serotonin biosynthesis pathway in human Gut Ins−enteroendocrine cells, thereby causing them to differentiate into Gut Ins$^+$ Cells that make and secrete biologically active insulin. The pharmaceutical compositions will have one or more of the following effects of increasing insulin secretion and serum insulin, increasing insulin sensitivity, increasing glucose tolerance, reducing intracellular serotonin. Alternatively, pharmaceutical compositions are directed to Ins+ enteroendocrine cells. Typically, the Ins+ enteroendocrine cells are in a form suitable for transplantation into the subject.

The therapeutic agents are generally administered in an amount sufficient to treat or prevent an enumerated disease associated with impaired pancreatic endocrine function, including diabetes type 1 and 2, metabolic syndrome, and obesity in a subject; or to reduce fat mass. The pharmaceutical compositions of the invention provide an amount of the active agent effective to treat or prevent an enumerated disease or disorder.

Active agents of the invention may be chemically modified to facilitate uptake by Gut Ins-cells such as enteroendocrine cells. For example, it could be fused to a bile acid or fatty acid to facilitate uptake by gut cells; or it may be packaged in liposomes or another lipid-based emulsion system to facilitate its uptake; it may be encoded by bacteria expressing a modified cell surface antigen that promotes its binding to gut epithelial cells, including N3 Progenitor cell-permeable peptides was used to improve cellular uptake. (Gratton et al., Nature Medicine 9, 357-362 (2003)).

The term "administer" is used in its broadest sense and includes any method of introducing the compositions of the present invention into a subject. Administration of an agent "in combination with" includes parallel administration of two agents to the patient over a period of time such as administration of an agent that reduces expression, biosynthesis, signaling or activity of serotonin and an agent that reduces the expression of FOXO1 expression or biological activity over a period of time, co-administration (in which the agents are administered at approximately the same time, e.g., within about a few minutes to a few hours of one another), and co-formulation (in which the agents are combined or compounded into a single dosage form suitable for oral, subcutaneous or parenteral administration).

The pharmaceutical compositions of the present invention may be administered in a number of ways depending upon whether local or systemic treatment is desired and upon the area to be treated. The gastrointestinal (G.I.) tract is a desired route for the administration of pharmacological agents. Drugs are normally well absorbed from the intestines, and dosage forms such as capsules, tablets, and suspensions are well accepted by the general population. The gut regions that have the highest density of Gut Ins+ cells in mice with FOXO1 ablation are located in the distal ileum and colon and duodenum. Drug delivery systems targeted to the colon are known in the art to include covalent linkage compositions, polymer coated compositions, compositions embedded in matrices, time release compositions, redox-sensitive polymer compositions, bioadhesive compositions, microparticle coating compositions, and osmotic delivery compositions. See U.S. Pat. No. 8,470,885. A number of different formulations are available for delivery of desired compositions to the colon including amylose coated tablets, enterically coated chitosan tablets, matrix within matrix or multimatrix systems or polysaccharide coated tablets. Multimatrix controlled release systems are disclosed in U.S. Pat. No. 7,421,943. Therefore in some embodiments the pharmaceutical compositions are administered orally or locally to the colon or in formulations that target them for absorption in the duodenum or it can be administered by implanting an osmotic pump, preferably at a site or subcutaneous that is proximal to the duodenum, distal ileum or colon.

Administration can also be intravenous, parenterall intraarterial, subcutaneous, intraperitoneal or intramuscular injection or infusion; or intracranial, e.g., intrathecal or intraventricular, administration. The pharmaceutical compositions may be formulated in rectal compositions such as suppositories or retention enemas, e.g., containing conventional suppository bases such as cocoa butter or other glycerides. The compositions so formulated will be designed to give an effective dosage to the colon in addition to other areas a rectal administration might affect.

In recent years there has been a tendency towards the development of controlled release dosage forms that will provide therapy over an extended period of time. Normally this would be once a day and it is believed that such a change in dosage regimen will reduce adverse reactions and side effects and also improve patient compliance. The design and evaluation of controlled release dosage forms must, however, take into account the properties of the G.I. tract, including the rapid transit of material through the small intestine. The use of synthetic polymers that may have muco- or bio-adhesive properties has been investigated and is disclosed in WO 85/02092.

In some embodiments a slow release preparation comprising the active agents is formulated. It is desirable to prolong delivery with these slow release preparations so that the drug may be released at a desired rate over this prolonged period. By extending the period, the drug can if required be released more slowly, which may lead to less severe adverse reactions and side effects. The preparation of sustained, controlled, delayed or anyhow modified release form can be carried out according to different known techniques: 1. The use of inert matrices, in which the main component of the matrix structure opposes some resistance to the penetration of the solvent due to the poor affinity towards aqueous fluids; such property being known as lipophilia; 2. The use of hydrophilic matrices, in which the main component of the matrix structure opposes high resistance to the progress of the solvent, in that the presence of strongly hydrophilic groups in its chain, mainly branched, remarkably increases viscosity inside the hydrated layer; and 3. The use of bioerodible matrices, which are capable of being degraded by the enzymes of some biological compartment. See U.S. Pat. No. 7,431,943.

The term "slow release" refers to the release of a drug from a polymeric drug delivery system over a period of time that is more than one day wherein the active agent is formulated in a polymeric drug delivery system that releases effective concentrations of the drug. Drug delivery systems may include a plurality of polymer particles containing active drug material, each of the particles preferably having a size of 20 microns or less, and incorporating on the outer surface of at least some of the particles a bioadhesive material derived from a bacterium such that in use the bioadhesive material will adhere to the small intestine of the gut. Such drug delivery systems have been described in U.S. Pat. No. 6,355,276. The use of these microorganisms in the design allow for a controlled release dosage form with extended gastrointestinal residence.

In certain embodiments, dosage forms of the compositions of the present invention include, but are not limited to, implantable depot systems. The depot systems may include FOXO or serotonin affecting agents or include Ins+ enteroendocrine cells. In one embodiment, the depot system includes ins+ enteroendocrine cells imbedded in a three-dimensional matrix. The three-dimensional matrices to be used are structural matrices that provide a scaffold to hold and support the cells, and are porous to allow fluid flow. Scaffolds can take forms ranging from fibers, gels, fabrics, sponge-like sheets, and complex 3-D structures with pores and channels fabricated using complex Solid Free Form Fabrication (SFFF) approaches. As used herein, the term "scaffold" means a three-dimensional (3D) structure (substrate and/or matrix). It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel. In certain embodiments, the scaffold is biodegradable.

Examples of biodegradable depot systems include but are not limited to PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy} methane), CPM; poly(p-{carboxyphenoxy} propane), CPP; poly(p-

{carboxyphenoxy}hexane)s CPH; polyamines, polyurethanes, polyesteramides, polyorthoesters {CHDM: cis/trans-cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxy valerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

Self emulsifying microemulsion drug delivery systems (SMEDDS) are known in the art as effective delivery systems into the G.I. tract. See U.S. Patent Application 2001/00273803. The term SMEDDS is defined as isotropic mixtures of oil, surfactant, cosurfactant and drug that rapidly form oil in water microemulsion when exposed to aqueous media or gastrointestinal fluid under conditions of gentle agitation or digestive motility that would be encountered in the G.I. tract.

Thermostable nanoparticles may be contained in a drug delivery system targeted for the G.I. tract. See U.S. Patent Application 2000/60193787. These drug delivery systems may include at least one type of biodegradable and/or bioresorbable nanoparticle and at least one drug that possesses at least one of the following properties: emulsifier or mucoadhesion. The drug may substantially cover the surface of the nanoparticle and may be used for delivering at least one drug across a mucosal membrane such as the lining of the gut.

Certain medications, for example resins that prevent bile acid absorption, or inhibitors of sugar breakdown, are used in the treatment of type 2 diabetes and are not absorbed at all in the plasma. Such formulations are useful for the pharmaceutical formulations of the present invention.

In certain embodiments, the pharmaceutical compositions of the present invention comprise about 0.1 mg to 5 g, about 0.5 mg to about 1 g, about 1 mg to about 750 mg, about 5 mg to about 500 mg, or about 10 mg to about 100 mg of therapeutic agent.

In addition to continuous administration using osmotic pumps, active agents can be administered as a single treatment or, preferably, can include a series of treatments, that continue at a frequency and for a duration of time that causes one or more symptoms of the enumerated disease to be reduced or ameliorated, or that achieves the desired effect including effects of increasing insulin secretion and serum insulin, increasing insulin sensitivity, increasing glucose tolerance, decreasing weight gain, decreasing fat mass, and causing weight loss.

It is understood that the appropriate dose of an active agent depends upon a number of factors within the ken of the ordinarily skilled physician, veterinarian, or researcher. The dose(s) vary, for example, depending upon the identity, size, and condition of the subject or sample being treated, further depending upon the route by which the composition is to be administered, and the effect which the practitioner desires the an active agent to have. It is furthermore understood that appropriate doses of an active agent depend upon the potency with respect to the expression or activity to be modulated. Such appropriate doses may be determined using the assays described herein. When one or more of these active agents are to be administered to an animal (e.g., a human) in order to modulate expression or activity a Foxo protein, a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Type 1 diabetes is usually diagnosed in children and young adults—but can occur at any age, and was previously known as juvenile diabetes. In type 1 diabetes, the body does not produce insulin. Insulin is a hormone that is needed to convert sugar (glucose), starches and other food into energy needed for daily life. Conditions associated with type 1 diabetes include hyperglycemia, hypoglycemia, ketoacidosis and celiac disease.

Type 2 diabetes is the most common form of diabetes. In type 2 diabetes, either the body does not produce enough insulin or the cells ignore the insulin. Conditions associated with type 2 diabetes include hyperglycemia and hypoglycemia.

Disorders associated with energy metabolism include diabetes, glucose intolerance, decreased insulin sensitivity, decreased pancreatic beta-cell proliferation, decreased insulin secretion, weight gain, increased fat mass and decreased serum adiponectin.

The therapeutic agent can be formulated with an acceptable carrier using methods well known in the art. The actual amount of therapeutic agent will necessarily vary according to the particular formulation, route of administration, and dosage of the pharmaceutical composition, the specific nature of the condition to be treated, and possibly the individual subject. The dosage for the pharmaceutical compositions of the present invention can range broadly depending upon the desired effects, the therapeutic indication, and the route of administration, regime, and purity and activity of the composition.

A suitable subject, preferably a human, can be an individual or animal that is suspected of having, has been diagnosed as having, or is at risk of developing an enumerated disease, and like conditions as can be determined by one knowledgeable in the art.

Techniques for formulation and administration can be found in "Remington: The Science and Practice of Pharmacy" (20th edition, Gennaro (ed.) and Gennaro, Lippincott, Williams & Wilkins, 2000), incorporated herein by reference. The pharmaceutical compositions of the present invention can be administered to the subject by a medical device, such as, but not limited to, catheters, balloons, implantable devices, biodegradable implants, prostheses, grafts, sutures, patches, shunts, or stents. A detailed description of pharmaceutical formulations of oligonucleotides is set forth in U.S. Pat. No. 7,563,884.

The pharmaceutical compositions of the present invention may be administered in a number of ways depending upon whether local or systemic treatment is desired and upon the area to be treated. Administration may be-oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Active agents may be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active agent in the required amount in an appropriate solvent with one or a combination of the ingredients enumerated above, as required, followed by filter sterilization. Generally, dispersions are prepared by incorporating the active agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present invention for treatment of atherosclerosis or the other elements of metabolic syndrome can be formulated and administered systemically or locally. Techniques for formulation and administration can be found in "Remington: The Science and Practice of Pharmacy" (20th edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL® or corn starch; a lubricant such as magnesium stearate or STEROTES® a glidant such as colloidal silicon dioxide; a sweetening agent such as sucrose or saccharin; or a flavoring agent such as peppermint, methyl salicylate, or orange flavoring.

The composition may be formulated, for example, as a tablet or capsule or as a unit dose that may be suspended in a liquid immediately prior to use. The tablet or capsule may have an enteric coating. The enteric coating (and the capsule, if appropriate) may dissolve or disintegrate, preferably rapidly (e.g. up to 5, 10, 15, 20, 30, 60, 120, 240, 300, or 360 minutes or longer), when it reaches alkaline conditions, for example on entering the small intestine.

Alternatively, the tablet or capsule may not have an enteric coating but may disintegrate in the stomach to release an enteric coated composition comprising agents.

Examples of enteric release materials are pH-sensitive polymers which provide an aqueous barrier and do not dissolve or disintegrate in acidic aqueous environs typical of the stomach, but which do dissolve or disintegrate in the higher pH aqueous environs typical of the intestines. The time duration of the disintegration upon reaching a higher pH condition dictates where in the intestine the agent is released.

Dosage unit forms of certain embodiments include enteric coated capsules or tablets, or enteric coated active agent. Other related dosage unit forms active agent encased in hard- or soft-shelled capsules with the shell made of an enteric release material. Another dosage unit form provides active agent embedded in a matrix which is soluble or erodible in the intestines but not in the stomach.

For the pharmaceutical compositions in dosage unit form, each dosage unit form may contain from about 0.1 mg to about 1000 mg of active agent, more typically from about 1 mg to about 500 mg of active agent, more typically still from about 5 mg to about 200 mg of active agent.

In a specific embodiment, a dosage unit form is directed to an enteric coated tablet comprising a tablet core containing active agent surrounded by an enteric coating. Tablet cores area typically made by mixing granular or powdered active agent with a pharmaceutical carrier and compressing the resulting mixture into a tablet core by conventional means. The tablet core is then coated with an enteric release material by conventional means, such as in a pan coater or a fluidized bed coater. Examples of commercially available enteric release materials which may be used to produce dosage unit forms of the present invention include cellulose acetate trimellitate, hydroxypropyl methylcellulose phthalate, carboxymethylethylcellulose, co-polymerized methacrylic acid/methacrylic acid methyl esters such as, for instance, materials known under the trade name EUDRAGIT® L12.5, L100, or EUDRAGIT® S12.5, S100 or similar compounds used to obtain enteric coatings, methacrylic acid copolymers (Eudragit® L, S and L30D from Rohm Pharma GmbH, Darmstadt, West Germany); cellulose acetate phthalate (Aquateric® from FMC Corp., Philadelphia, Pa.); polyvinyl acetate phthalate (Coteric® from Colorcon Inc., West Point, Pa.); and hydroxypropyl methylcellulose phthalate (HP50 and HP55 from Shin-Etsu Chemical Co., Ltd., Tokyo, Japan). The preferred thickness of enteric coating used is sufficient to protect the active agent from exposure in the stomach but disintegrates rapidly in the intestines, preferably in the small intestine, more preferably in the duodenum or jejunum, to expose the active agent, such that it contacts gut cells, preferably serotonin+ enteroendocrine cells in the intestine.

Another dosage unit form embodiment is an enteric coated hard gelatin capsule containing active agent. Active agent is typically mixed with a pharmaceutical carrier and filled into hard gelatin capsule shells. The capsules are then enteric coated using a coating as described for enteric coated tablets above.

Another dosage unit form embodiment is enteric coated granules of active agent. Granules comprising active agent and, preferably, a pharmaceutical carrier are prepared and enterically coated using an enteric coating material as described hereinabove. A dosage unit form of the enteric coated granules is prepared by, preferably blending them with an appropriate pharmaceutical carrier, and compressing them into tablets or filling them into hard gelatin capsule shells by conventional means.

Another dosage unit form embodiment pertains to a soft gelatin capsule containing a solution, suspension or emulsion of active agent. The soft gelatin capsule shell is made of an enteric release material which remains intact in the stomach and prevents exposure of the active agent in the stomach, but which dissolves or disintegrates in the intestines and releases the active agent in the intestine as described above.

Systemic administration can also be by transmucosal means to the intestinal or colon. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams as generally known in the art.

The compounds can also be prepared in the form of suppositories_(e.g., with conventional suppository bases such as cocoa butter and other glycerides) or retention enemas for rectal delivery.

In one embodiment, the active agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art, for example, as described in U.S. Pat. No. 4,522,811

In an embodiment of the invention, the agent can be delivered by long-term, automated drug delivery to the gut using an osmotic pump to infuse a desired dose of the agent for a desired time. Insulin pumps can be adapted to deliver the agent to the gut. The delivery rate of the agent to control glucose intolerance, diabetes types 1 or 2 can be readily adjusted through a large range to accommodate changing insulin requirements of an individual (e.g., basal rates and bolus doses). New pumps permit a periodic dosing manner, i.e., liquid is delivered in periodic discrete doses of a small fixed volume rather than in a continuous flow manner. The overall liquid delivery rate for the device is controlled and adjusted by controlling and adjusting the dosing period. The pump can be coupled with a continuous blood glucose monitoring device and remote unit, such as a system described in U.S. Pat. No. 6,560,471, entitled "Analyte Monitoring Device and Methods of Use." In such an arrangement, the hand-held remote unit that controls the continuous blood glucose monitoring device could wirelessly communicate with and control both the blood glucose monitoring unit and the fluid delivery device delivering therapeutic agents of the present invention. In certain embodiments, the agent may be administered at a rate of from about 0.3-100 ng/hour, preferably about 1-75 ng/hour, more preferably about 5-50 ng/hour, and even more preferably about 10-30 ng/hour. The agent may be administered at a rate of from about 0.1-100 pg/hr, preferably about 1-75 micrograms/hr, more preferably about 5-50 micrograms/hr, and even more preferably about 10-30 micrograms/hr. It will also be appreciated that the effective dosage of an active agent used for treatment may increase or decrease over the course of a particular treatment. Changes in dosage may result and become apparent from monitoring the level of insulin and/or monitoring glycemia control in a biological sample, preferably blood or serum.

5. Detailed Description of Experimental Results

FOXO1 and Serotonin (5HT) Colocalize in Human Gut

Experiments were first done to reproduce in humans the observation that Foxo1ablation in mouse gut endocrine progenitor cells gives rise to insulin-secreting cells. Immunohistochemistry was used to survey FOXO1 localization in the human gut. FOXO1 immunoreactivity was detected in 5HT+ cells in duodenum (FIG. 1H), jejunum, and colon (not shown). 90% of intestinal 5HT cells were FOXO1+. Interestingly, pancreatic b-cells also make 5HT.

Fluorescence immunohistochemistry was used to survey FOXO1 localization in the human gut (FIG. 1). FOXO1-expressing cells were most abundant near the bottom of crypts; 60% of FOXO1-positive cells were located between positions 0 to +9 relative to the crypt bottom in duodenum and colon, with lower frequencies at positions more distal than +10, and in jejunum and ileum (FIG. 2A-D). FOXO1 mRNA levels correlated with the abundance of FOXO1-immunoreactive cells (FIG. 2E). Intestinal lineage marker analysis indicated that FOXO1 expression was virtually restricted to CHROMOGRANIN A (CGA)-positive endocrine cells (FIG. 1A-D). 95.3±1.8% of FOXO1-positive cells were CGA-positive, whereas 61.8±3.8% of CGA-positive cells had immunoreactivity with FOXO1 in three human duodenal specimens. FOXO1-positive crypt cells were OLFACTOMEDIN4 (OLFM4)-negative (FIG. 1E), indicating that they are unlikely to be intestinal stem cells[13]. They were, however, immunoreactive with EPHB3, a pro-endocrine marker in pancreas[14] that localizes to columnar cells at the crypt base and Paneth cells (FIG. 1C)[15]. These findings are consistent with FOXO1-positive crypt cells being endocrine progenitors.

Figure 1H:
Figure 1I:
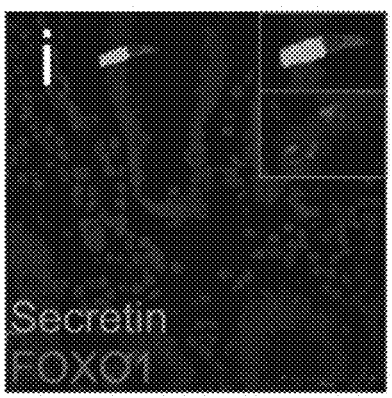
Figure 1J:
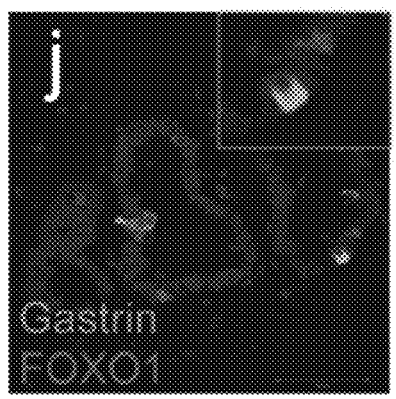
Figure 1K:
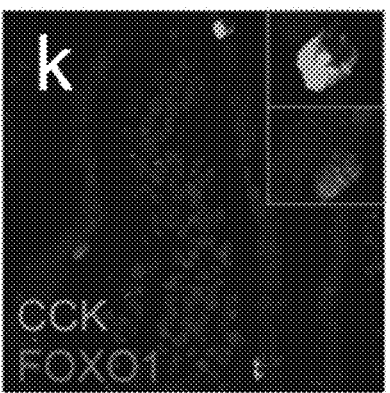
Figure 1L:
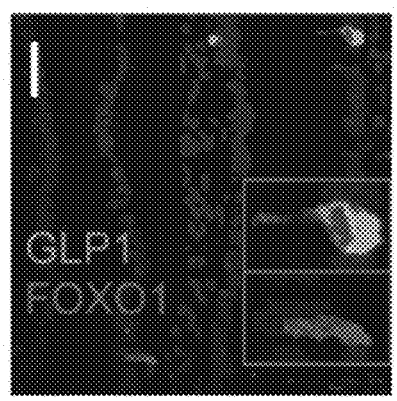
Figure 2E:
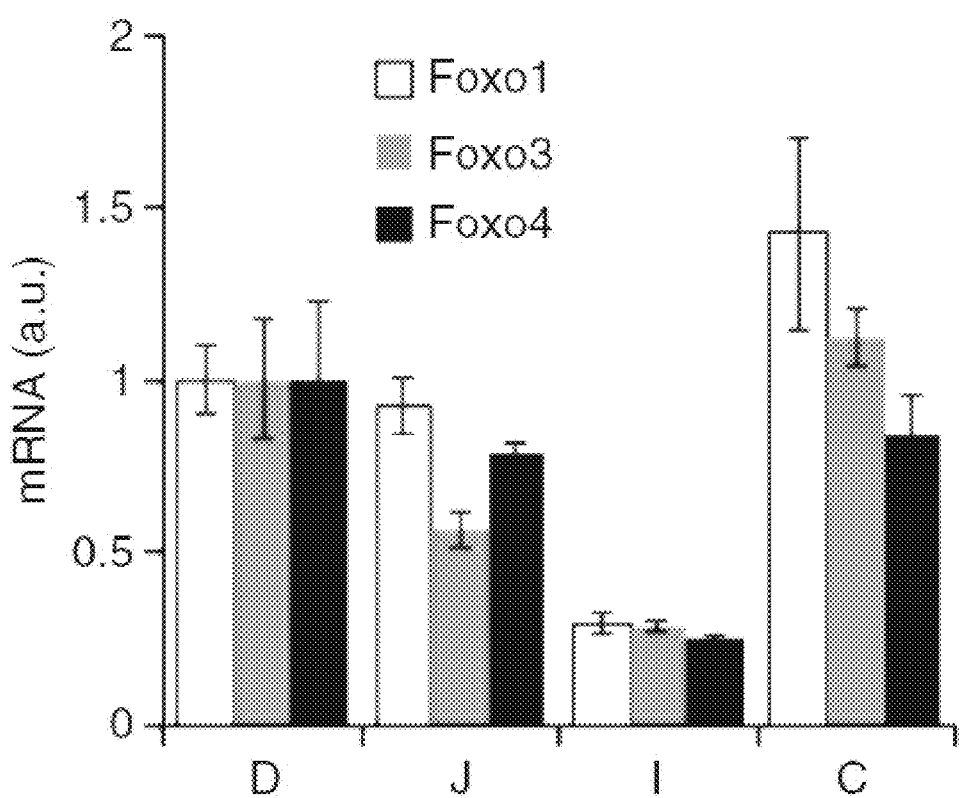
FIG. 2E, qPCR analysis of FOXO1 mRNA in human intestine (D: duodenum; J: jejunum; I: ileum; and C: colon).
Figure 2F:
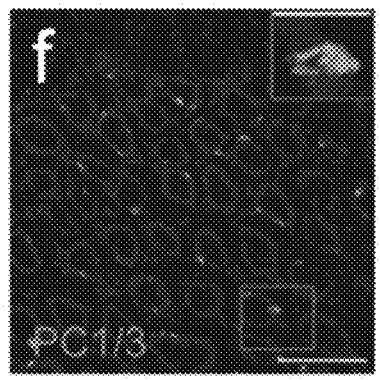
FIG. 2F-N, Immunostaining of FOXO1 with PC1/3, PC2, and SUR1 in human colon. Scale bars: 100 µm (n=3 for histology and qPCR) (*p<0.05). Data is presented as means±SEM.
Figure 2G:
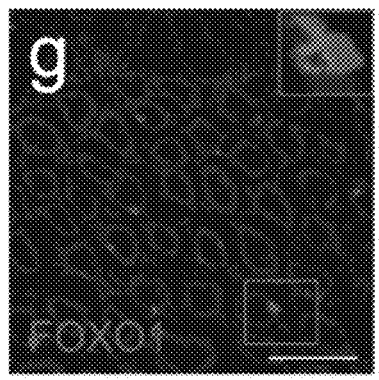
Figure 2H:
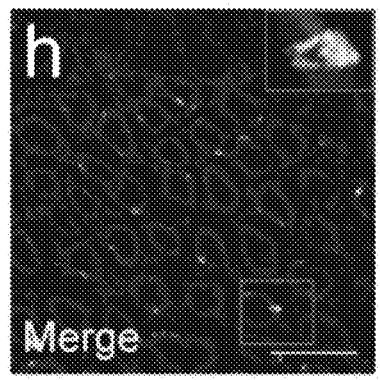
Figure 2I:
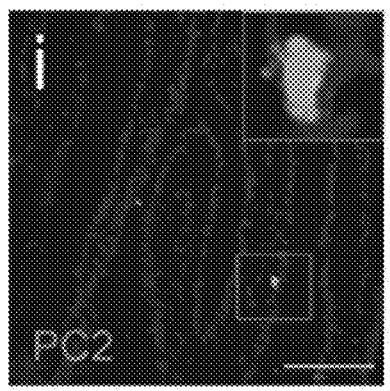
Figure 2J:
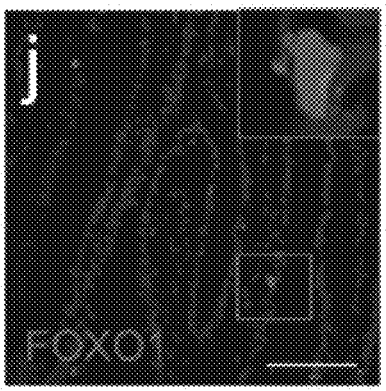
Figure 2K:
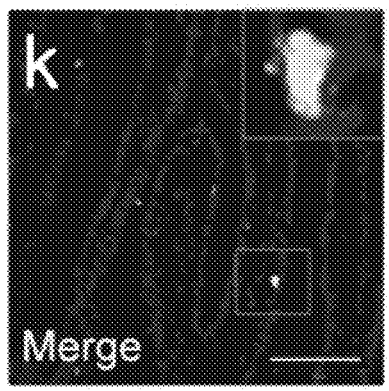
Figure 2L:
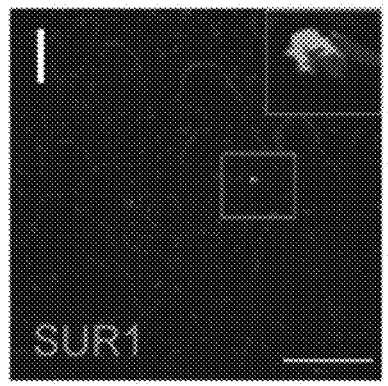
Figure 2M:
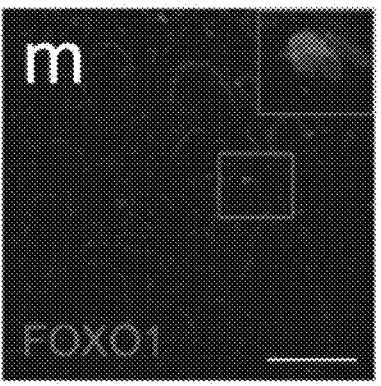
Figure 2N:
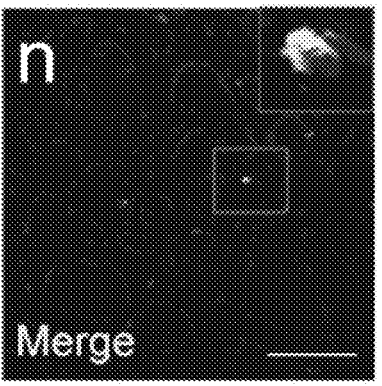

More than 80% of FOXO1-positive cells in villi were immunoreactive with serotonin antibodies and 85±11% of serotonin (5HT)-positive cells were FOXO1-positive (FIG. 1H). Interestingly, pancreatic β-cells also make serotonin19. In addition, FOXO1-immunoreactive cells showed reactivity with prohormone convertases (PC) 1/3 and 2[20,21], as well as the ATP-dependent potassium channel SUR1, an important protein for glucose-dependent insulin secretion in β-cells[22] (FIG. 2F-N). These findings indicate that FOXO1-positive gut cells share features with pancreatic β-cells. A small fraction of somatostatin-producing cells (~5% of total) also express FOXO1.

Generation and Analysis of Human Gut Organoids.

Figure 3A:
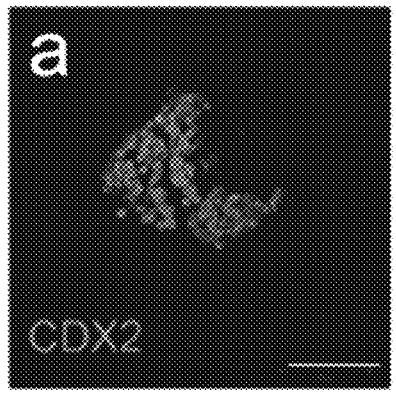
FIG. 3A, CDX2 (green) in 8-day-old organoids.
Figure 3B:
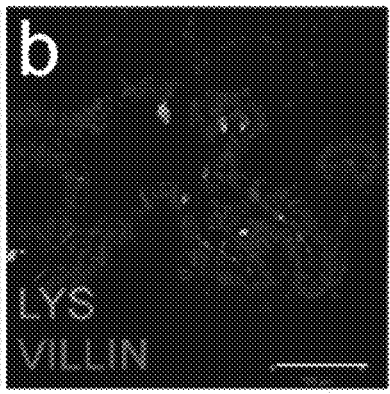
FIG. 3B, LYS (green) and VILLIN (red)
Figure 3C:
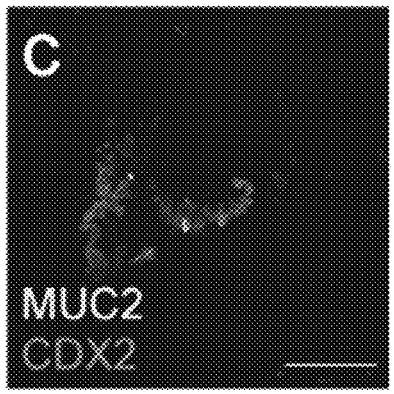
FIG. 3C, MUC2 (yellow) and CDX2 (magenta)
Figure 3D:
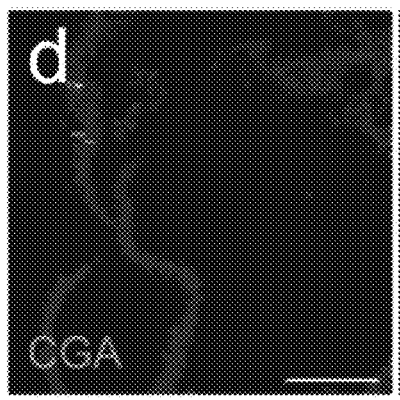
FIG. 3D, CGA (green) in 14-day-old organoids by immunohistochemistry.
Figure 3E:
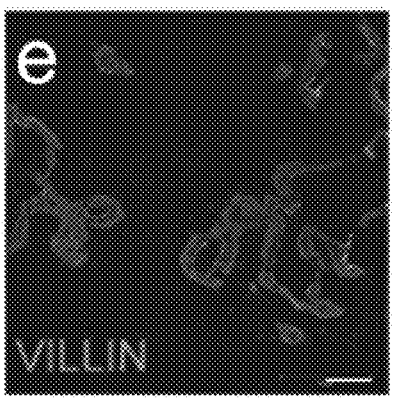
FIG. 3E, Villin.
Figure 3F:
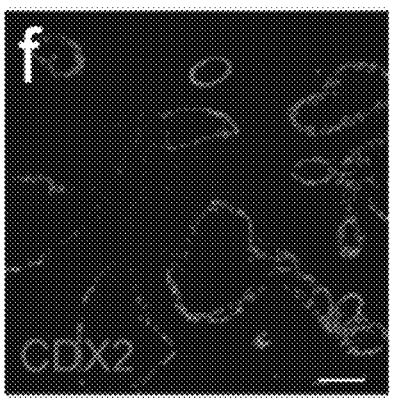
FIG. 3F, CDX2.
Figure 3G:
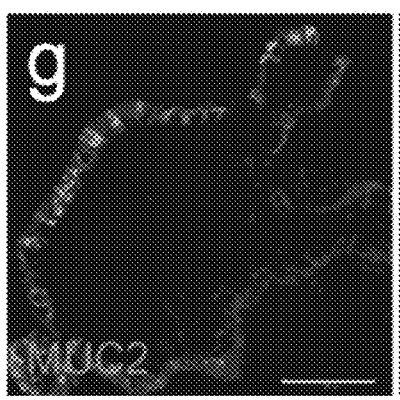
FIG. 3G, MUC2.
Figure 3H:
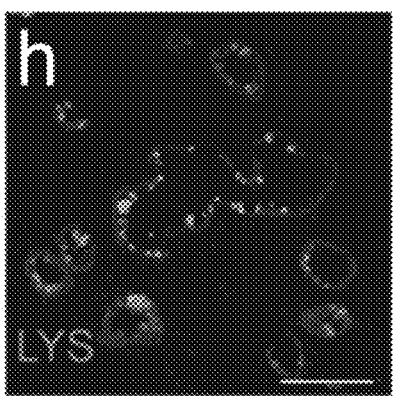
FIG. 3H, LYS.
Figure 3I:
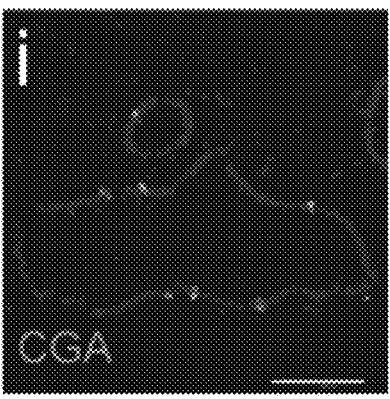
FIG. 3I, CGA.
Figure 3J:
FIG. 3J, vimentin (green) and VILLIN (red) in 150-day-old gut organoids.
Figure 3K:
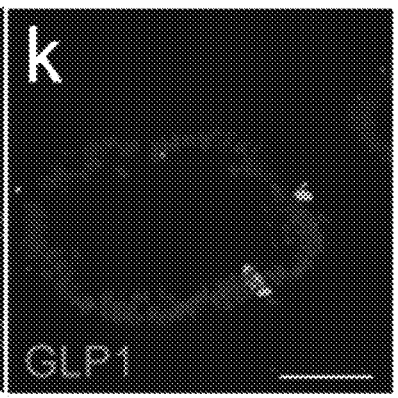
FIG. 3K-R, Analysis of endocrine cells; GLP1, GIP, 5HT, SSN, ghrelin, cholecystokinin (CCK), tuft cells (DCAMKL1), FOXO1 (green) and 5HT (red) in 150-day-old organoids.
Figure 3L:
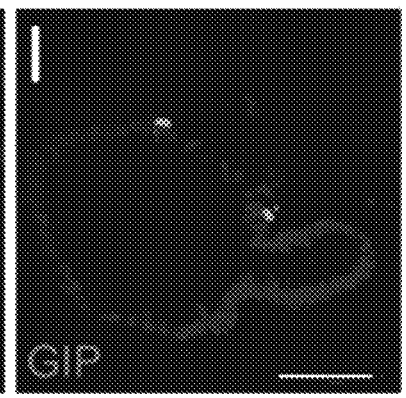
Figure 3M:
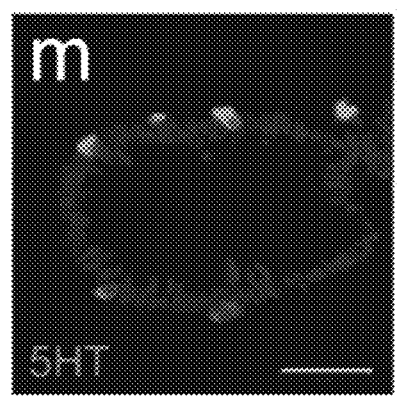
Figure 3N:
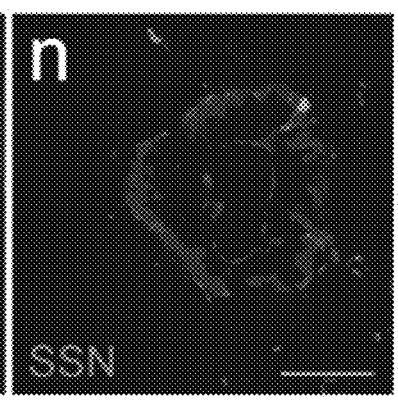
Figure 3O:
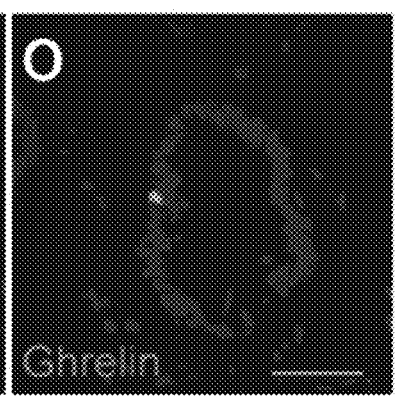
Figure 3P:
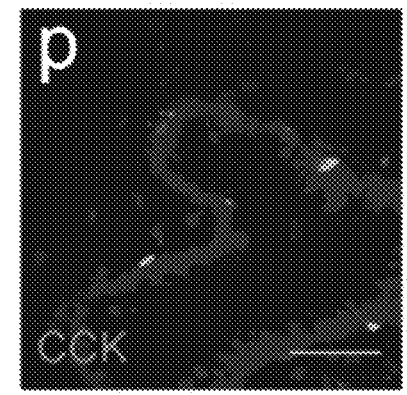
Figure 3Q:
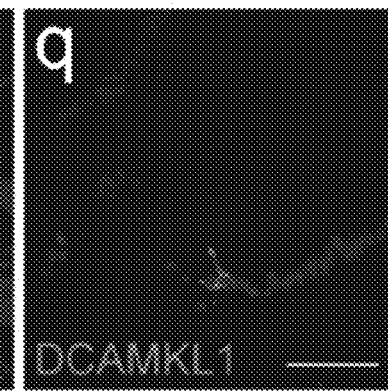
Figure 3R:
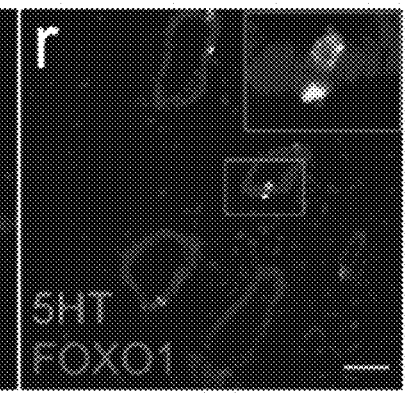
Figure 3S:
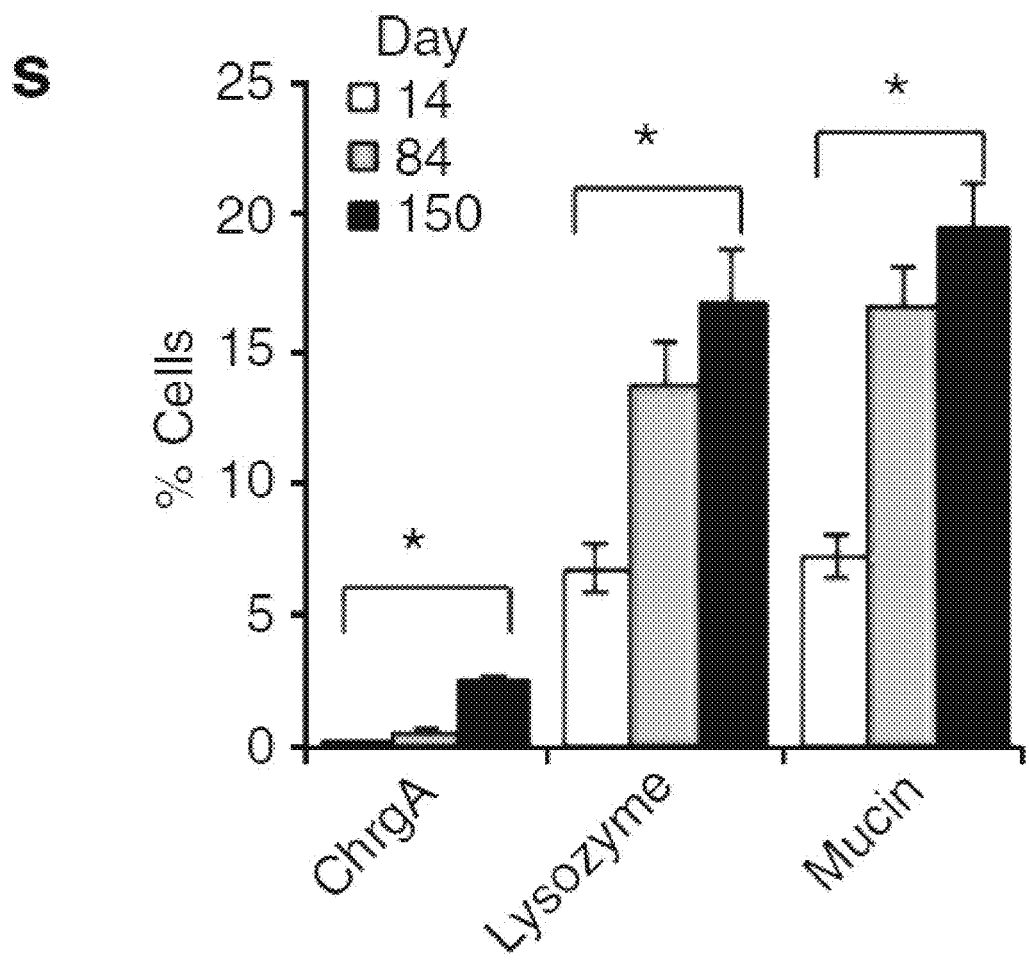
FIG. 3S, Quantification of CGA-, LYS- and MUC2-positive cells by immunohistochemistry.
Figure 3T:
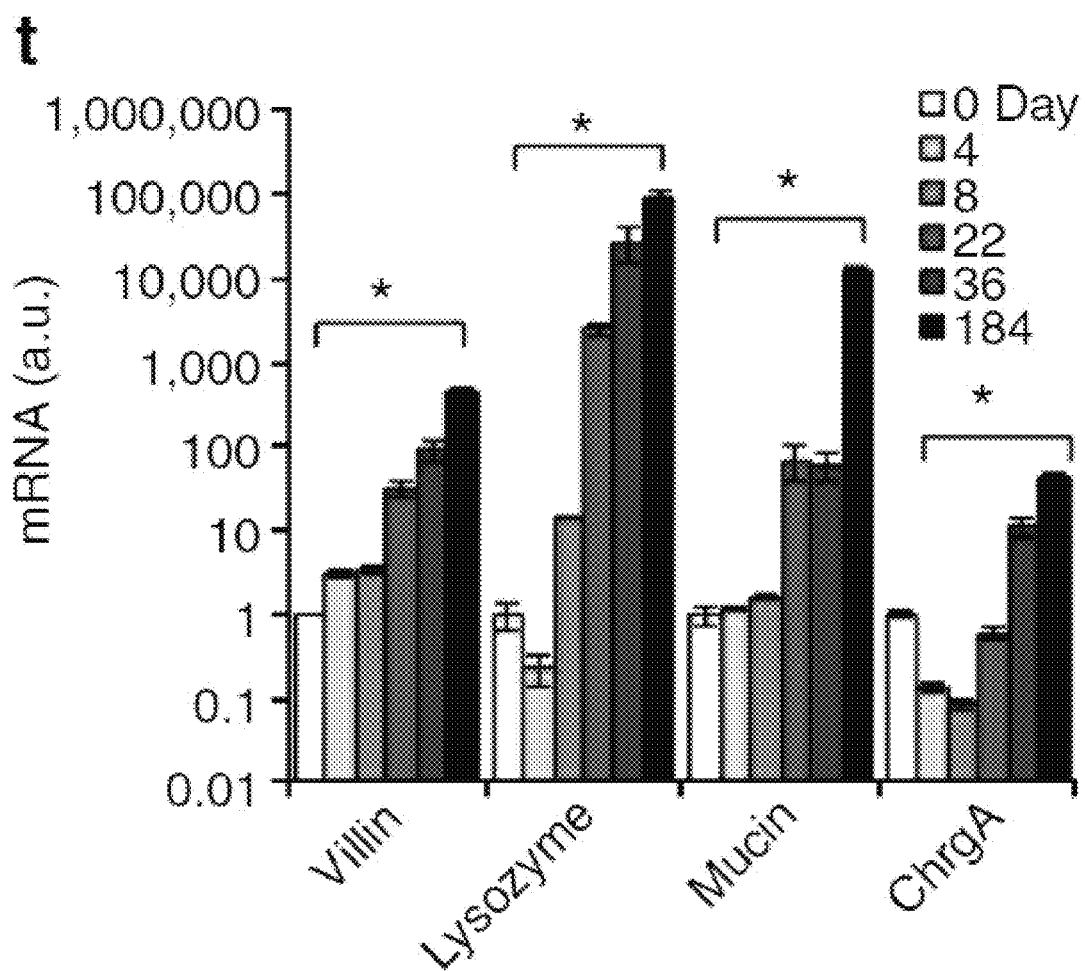
FIG. 3T-U, Time course qPCR analysis of VILLIN, LYSOZYME, MUCIN2 and CGA (T)

To assess the role of FOXO1 in human enteroendocrine cell differentiation, gut organoids were generated using three lines of human iPS cells derived from healthy donors[12,23]. Time course analyses with immunohistochemical markers indicated that CDX2-expressing cells appeared in 8-day-old organoids (FIG. 3A), followed by MUCIN (MUC2), LYSOZYME (LYS), and CGA-positive cells at day 14 of differentiation (FIG. 3B-D); no terminally differentiated enteroendocrine cells were detected at this stage. 150-day-old gut organoids resembled human gut morphology, including mesenchymal and enteroendocrine cells (FIG. 3E-R). The secretory lineages marked by MUC2 and LYS were present at physiologic frequencies, while CGA-positive cells were twice as abundant in iPS derived organoids as in gut (2.6±0.2 vs. 1.0±0.2%, p<0.05) (FIG. 3S).[5]. Time course analyses of mRNA expression indicated that lineage markers increased exponentially during differentiation, with a notable step-up between day 8 and 22, coincidental with the transition from budding microspheres to tridimensional culture in matrigel (FIG. 3T). Using immunohistochemistry, all principal endocrine cell types were shown to be present at physiologic levels (not shown)—including GLP1, GIP, somatostatin, gastrin, CCK, ghrelin, secretin, and serotonin. In certain embodiments, gut Ins+ cells are made by reducing expression of serotonin, in some cases with a reduction of FOXO1 expression.

Figure 3U:
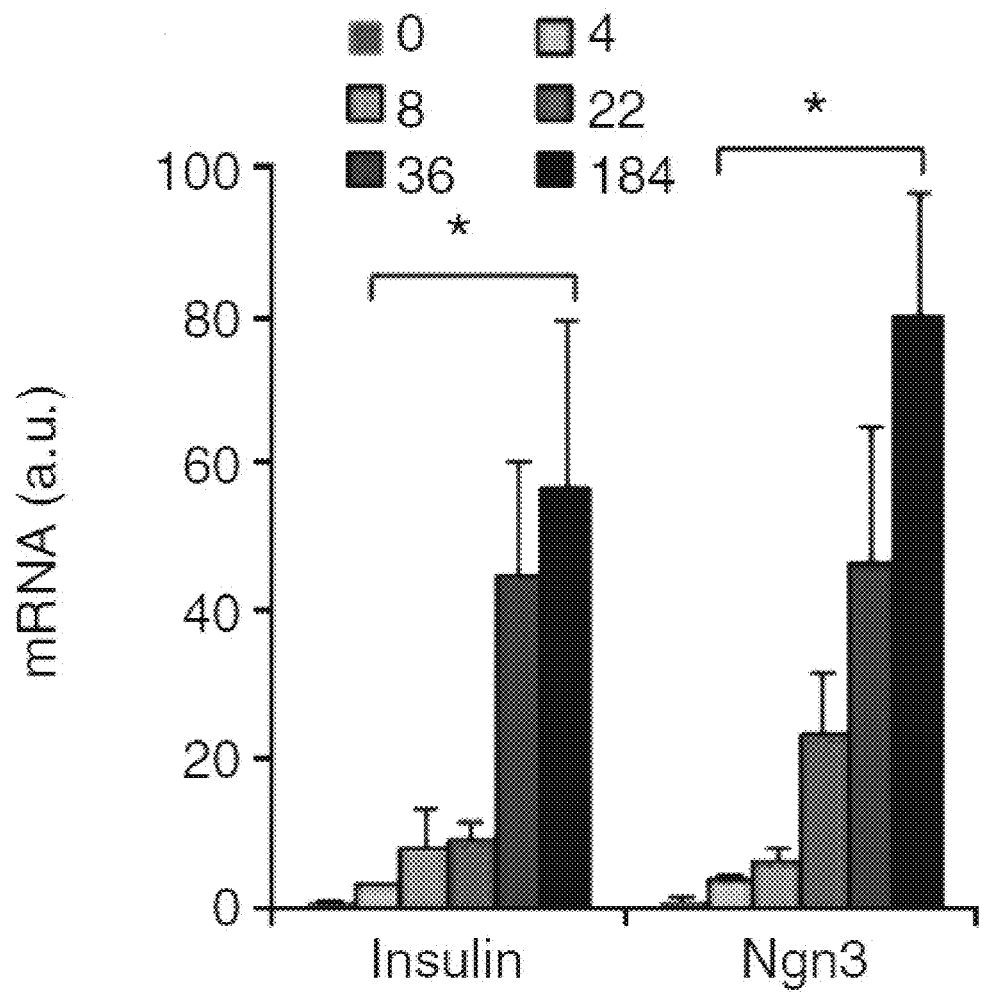
Figure 3V:
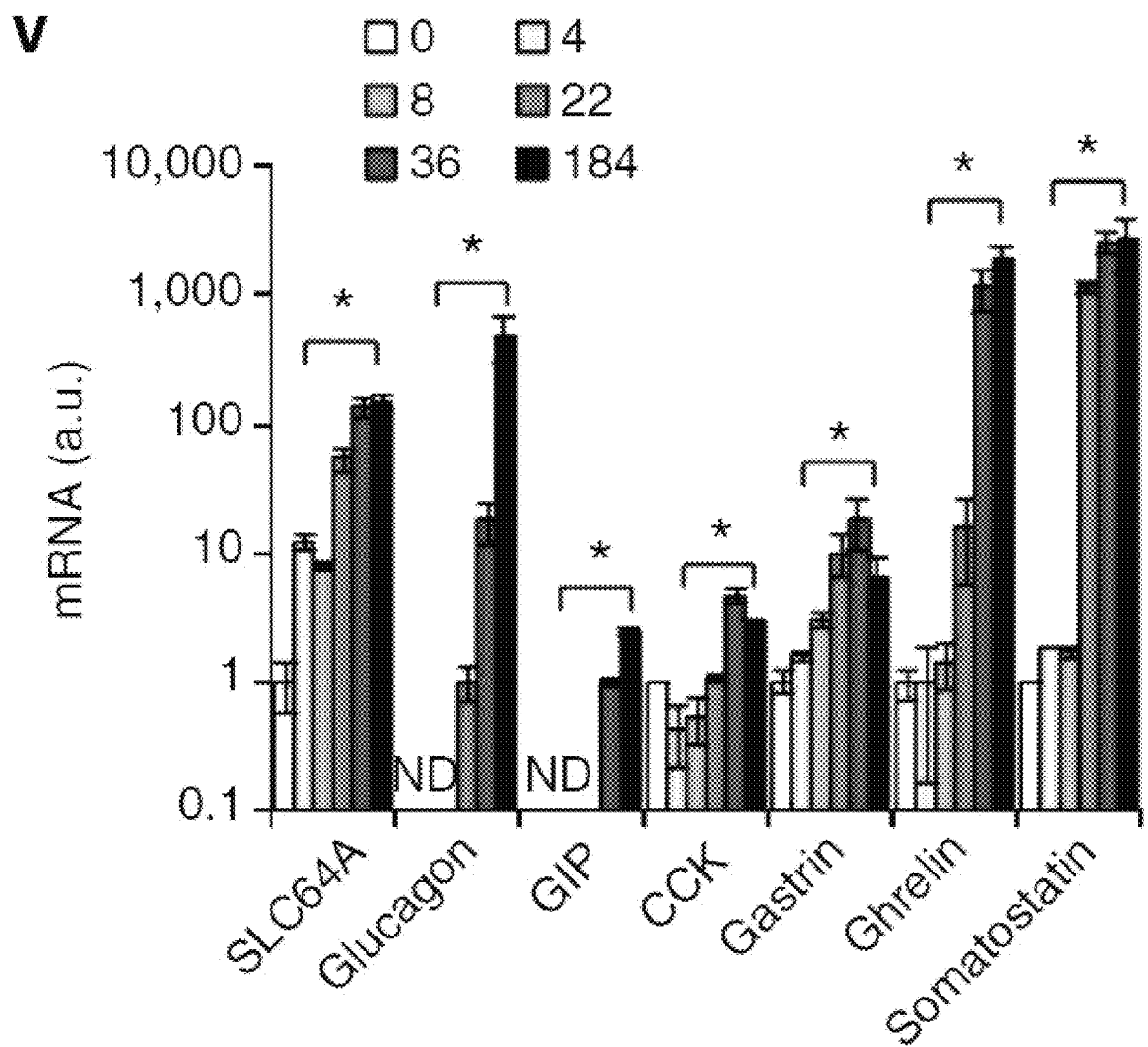
(FIG. 3V) Time qPCR analysis of INSULIN and NEUROG3 (U); SLC6A4 (serotonin transporter), GLUCAGON, GIP, CCK, GASTRIN, GHRELIN, and SSN during gut differentiation. Scale bars: 100 μm in panels a-j; 50 μm in panels k-r (n=3 each for histology and qPCR) (*p<0.05). Data is presented as means±SEM.

The presence and abundance of terminally differentiated enteroendocrine cells in human gut organoids have been characterized only in part. It was found that glucagon-like peptide 1 (GLP1)-, gastric inhibitory peptide (GIP)-, somatostatin (SSN)-, cholecystokinin (CCK)-, and 5HT-positive cells first appeared in ~90-days-old organoids. In contrast, gastrin-, secretin-, substance P—, and tufts cells appeared in 150-day-old organoids. (FIG. 3K-Q). qPCR analyses also revealed the time-dependent increases in mRNA levels of genes associated with endocrine progenitor and terminally differentiated enteroendocrine cells, including INSULIN (FIG. 3V-U and Supplementary Table 3). When the frequency of representative cell types (CGA, 5HT, GLP1 and SSN) in 230-day-old organoids with human duodenum was compared, it was found that CGA- and GLP1-positive cells were approximately twice as abundant in organoids as in duodenum; 5HT cells were present at comparable levels, whereas SSN cells were half as abundant in organoids compared to duodenum (FIG. 5K).

Figure 4A:
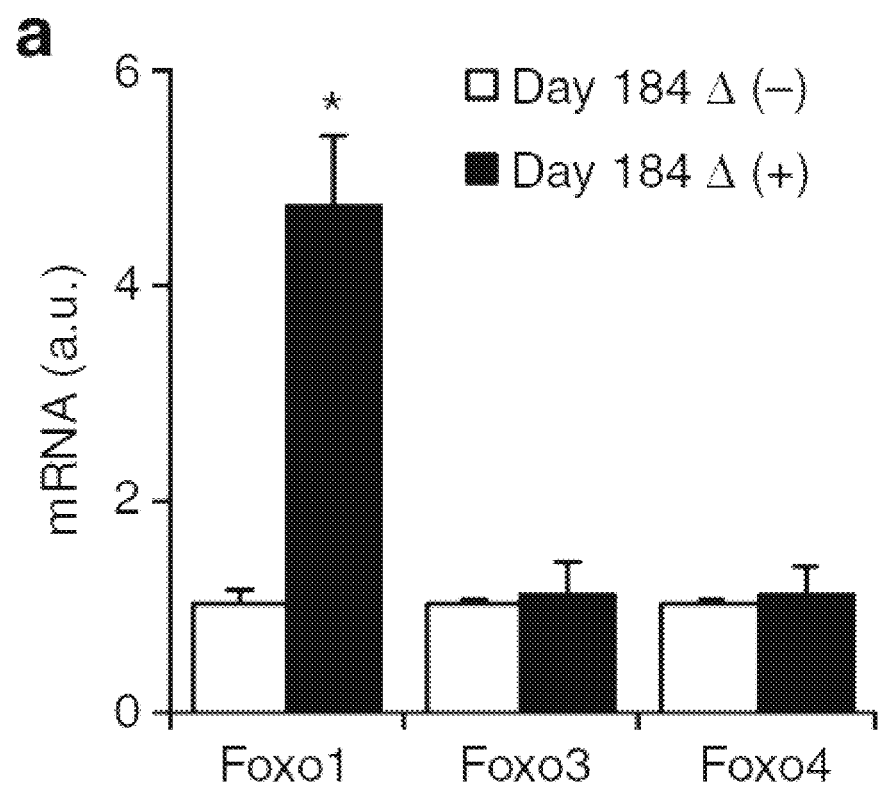
FIG. 4A-B, qPCR analysis of different markers in gut organoids transduced with control (empty bars) or HA-A256 FOXO1 adenovirus (black bars).
Figure 4B:
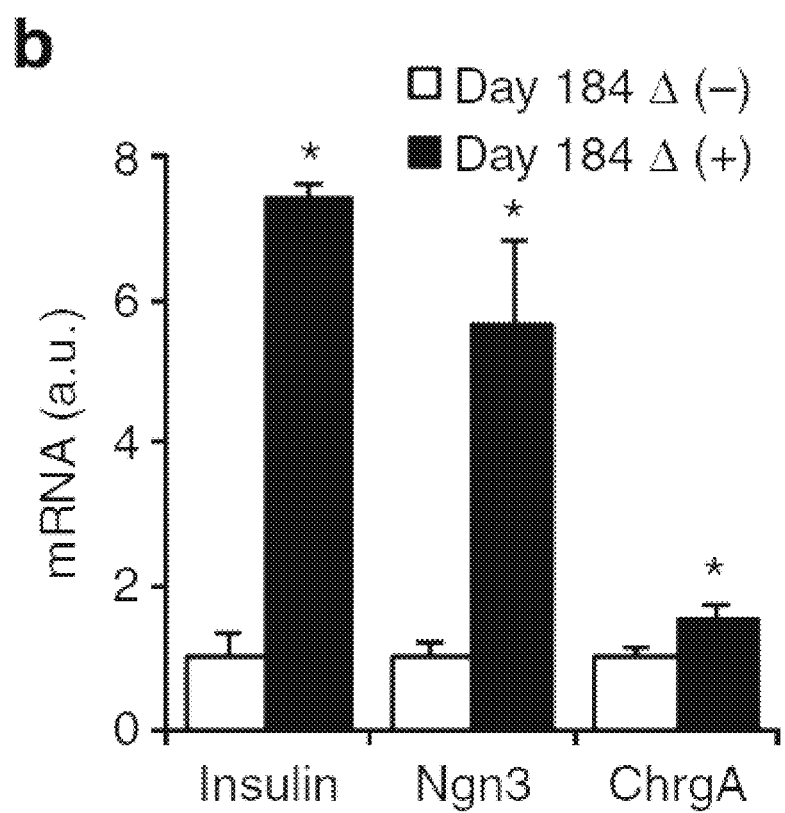
Figure 4C:
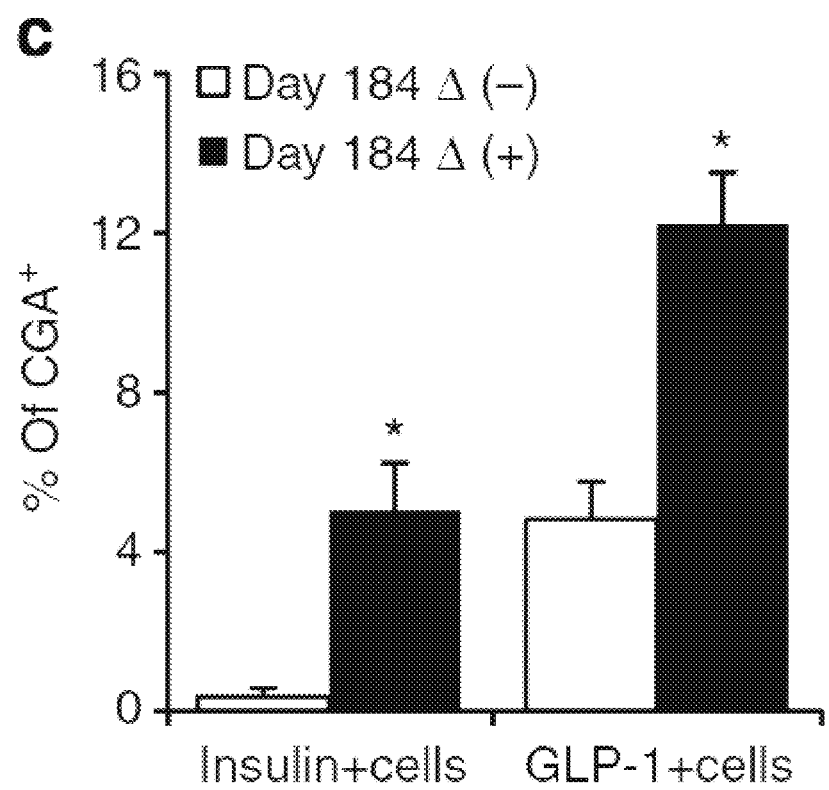
FIG. 4C, Quantification of insulin- and GLP1-positive cells in gut organoids transduced with control (empty bars) or HA-A256 FOXO1 adenovirus (black bars).
Figures 4D, 4E, 4G, 4H, 4I, 4J, 4K:
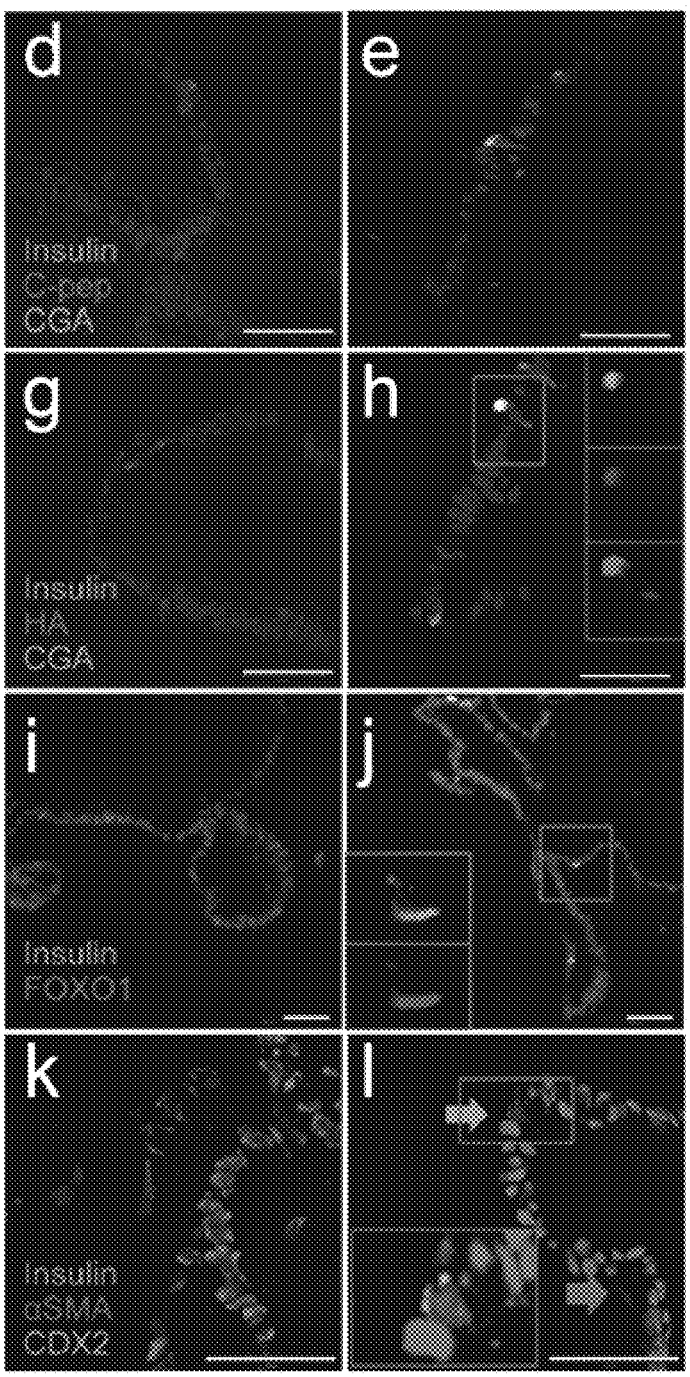
FIG. 4D-E, Immunohistochemistry with insulin (green), C-peptide (red), and CGA (magenta).
FIG. 4G-H, Co-immunohistochemistry with insulin (green), HA (to detect HA-A256 Foxo1 adenovirus) (red), and CGA (magenta).
Figure 4F:
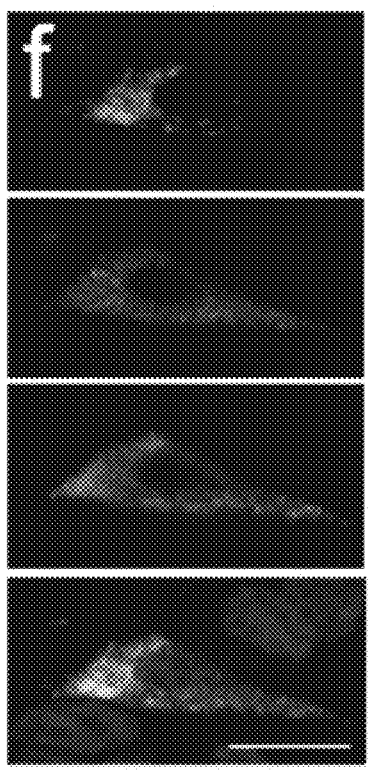
FIG. 4F, Magnification of a typical flask-shaped insulin-positive cell from panel e.

Enteroendocrine Cells in Human Gut Organoids Transduced with Adenovirus Expressing a Dominant-Negative Mutant FOXO1 can Differentiate into Insulin-Producing Cells To determine whether human enteroendocrine cells can be manipulated to yield insulin-producing cells, 170 days-old organoids were transduced with adenovirus expressing a dominant-negative mutant FOXO1 (HA-Δ256) tagged with a hemagglutinin epitope to enhance detection (HA-Δ256) (Ref. 24) and analyzed 2 weeks thereafter. mRNA analyses showed that gut organoids were efficiently transduced with this mutant, without affecting other FOXO isoforms (FIG. 4A). HA-Δ256 expression significantly increased transcripts of INSULIN, NEUROG3, and CGA by 8-, 6-, and 2-fold, respectively (FIG. 4B) (p<0.05). It should be noted however that CGA transcripts were ~8,000-fold more abundant than NEUROG3 transcripts, and ~40,000-fold more abundant than insulin transcripts at this stage (Supplementary Table 3

Immunohistochemical analyses of multiple differentiation experiments conducted with three separate iPS lines demonstrated the presence of insulin/C-peptide/CGA-positive cells (FIG. 4C-F). These cells represented 0.5% of CGA-positive cells in control organoids transduced with GFP adenovirus (~2 of 5,000 cells scored in each experiment), but their frequency increased to ~5% in gut organoids expressing dominant-negative FOXO1 (~31 of 4,000 cells scored in each experiment) (FIG. 2C) (p<0.05). In the latter, immunohistochemistry demonstrated that insulin-positive cells were immunoreactive with HA antibodies, indicating that the induction of insulin immunoreactivity occurred in cells with inactivated FOXO1 (FIG. 4G-H). Not all HA-positive cells were insulin-positive, possibly reflecting expression of the adenovirus in cells whose fate was not affected by FOXO1 ablation. Moreover, co-immunostaining with insulin and FOXO1 indicated that insulin-immunoreactive cells were invariably immunoreactive with cytoplasmic (i.e., inactive) FOXO1 (FIG. 4I-J). Immunostaining with insulin and CDX2 or αSMA (a marker of mesenchymal cells) showed that insulin-positive cells were immunoreactive with the former, but not with the latter, making it unlikely that the insulin-positive cells result from epithelial-mesenchymal transition (FIG. 4K-L). We have not detected insulin-positive cells in human intestinal samples. Therefore, we think that the presence of insulin-positive cells in gut organoid cultures is an artifact of the organoid system.

FOXO1 Inhibition Increased the Generation of Human Insulin+ Cells in Organoids

Figure 5A:
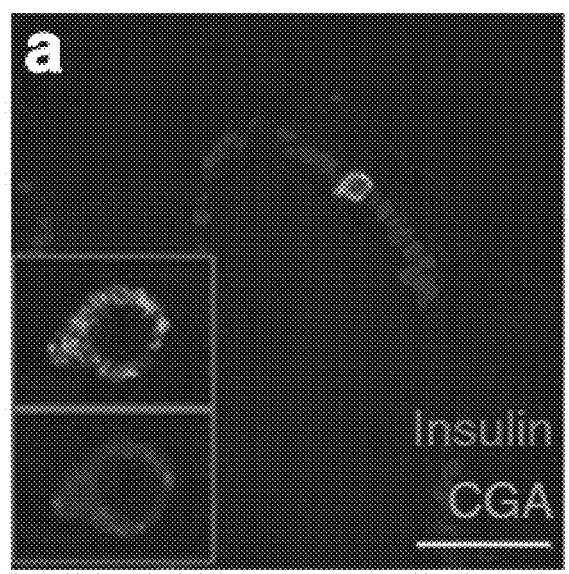
FIG. 5A, Immunohistochemistry with antibodies against insulin (green) and CGA (magenta) in 36-day-old gut organoids transduced with HA-A256 FOXO1 adenovirus.
Figure 5B:
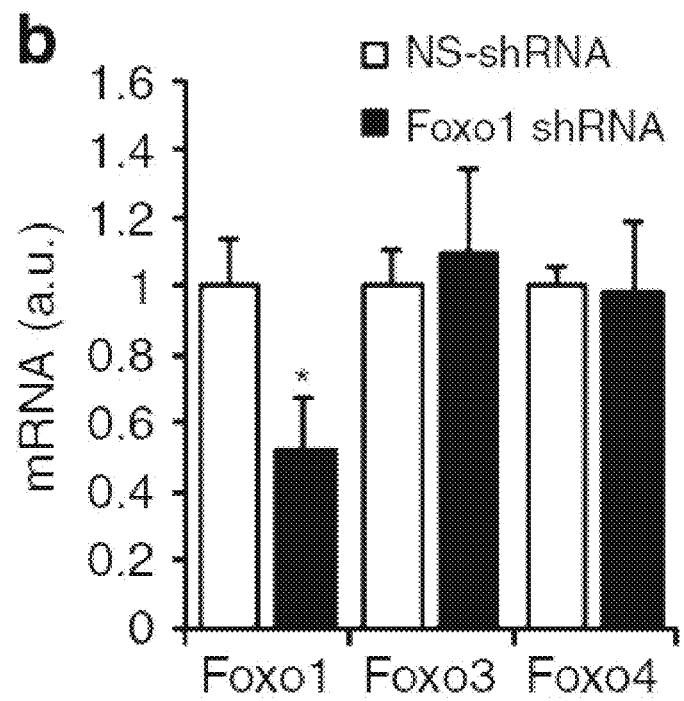
FIG. 5B, qPCR analysis of 230-day-old gut organoids transduced with control (empty bars) or FOXO1 lentiviral shRNA (black bars).
Figure 5C:
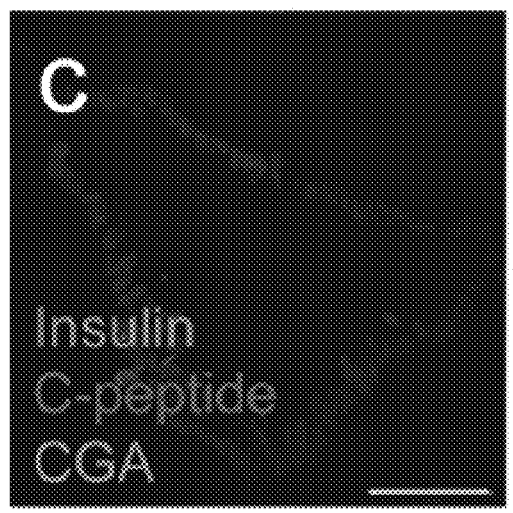
FIG. 5C-D, Immunohistochemistry with anti-insulin (green) and CGA (magenta) antibodies in 230-day-old gut organoids transduced with control or FOXO1 shRNA lentivirus.
Figure 5D:
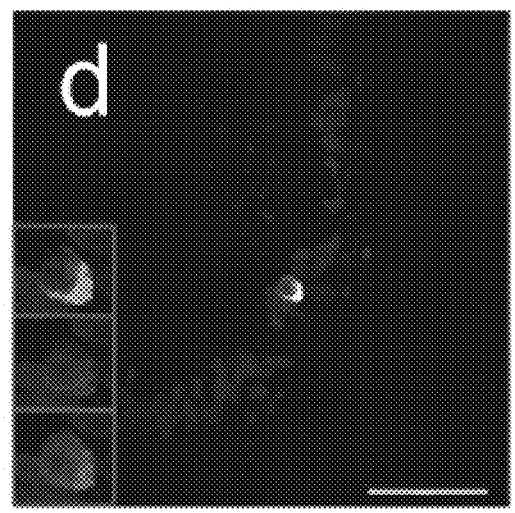

To provide independent evidence that FOXO1 inhibition increased the generation of insulin-positive cells, 36-day-old organoid cultures were studied. At that stage, insulin-immunoreactive cells were absent in untransduced organoids and INSULIN transcripts were exceedingly low (FIG. 3U and Supplementary Table 3). In contrast, following transduction with HA-Δ256, insulin-positive cells were detected, albeit at lower frequency than in 184-day-old organoids (FIG. 5A). In addition, lentivirus encoding FOXO1 shRNA was used as an alternative approach to inhibit FOXO1 function. Transduction of 230-day-old organoids with the virus decreased significantly FOXO1 mRNA (FIG. 5B), accompanied by the appearance of insulin-immunoreactive cells (FIG. 5C-D). Quantitative analyses of the data indicated that insulin-positive cells accounted for 8.5±1.7% of FOXO1-positive cells in organoids transduced with FOXO1 shRNA lentivirus vs. 0.8±0.5% in controls (p<0.05).

Figure 5E:
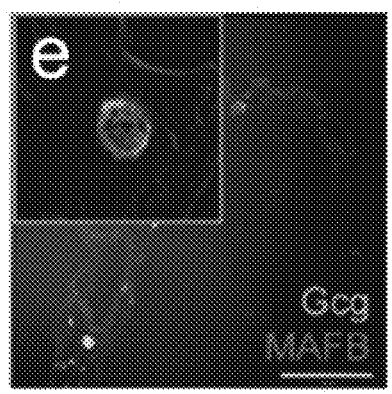
FIG. 5E, Immunohistochemistry with glucagon (green) and MAFB (red)

In earlier mouse experiments, FOXO1 ablation in gut endocrine progenitors resulted in the appearance of pancreatic glucagon-immunoreactive (β-like) cells, in addition to β-like-cells[6]. Likewise, glucagon-/MAFB-positive cells were found in 184-day-old gut organoids following FOXO1 inhibition, consistent with the generation of pancreatic b-cell-like cells (FIG. 5E). The immunoreactivity with MAFB was re markable, as thus far this β-cell-enriched transcription factor has failed to be induced in endoderm-derived pancreatic endocrine cells[1]. The frequency of glucagon-positive cells in gut organoids transfected with Δ256 was 10% of insulin-positive cells. Notably, glucagon-positive cells were not seen in organoids transduced with control adenovirus at this stage, consistent with an independent effect of FOXO1 inactivation on endocrine cell lineage determination.

Figure 5F:
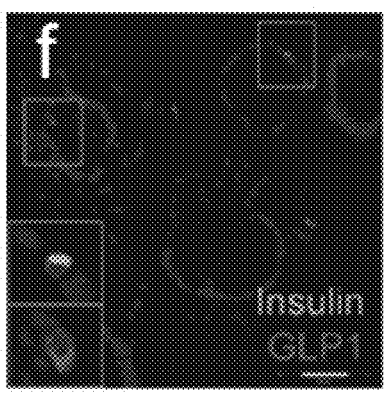
FIG. 5F, insulin (green) and GLP-1 (red)
Figure 5G:
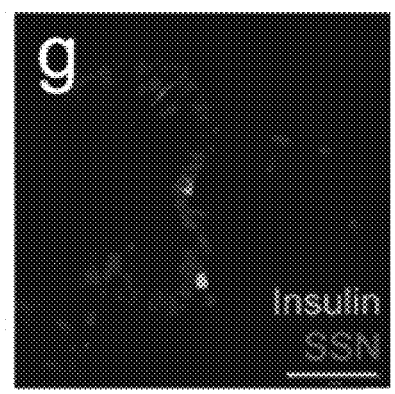
FIG. 5G, insulin (green) and somatostatin (red) in 184-day-old gut organoids transduced with HA-A256 adenovirus.
Figure 5H:
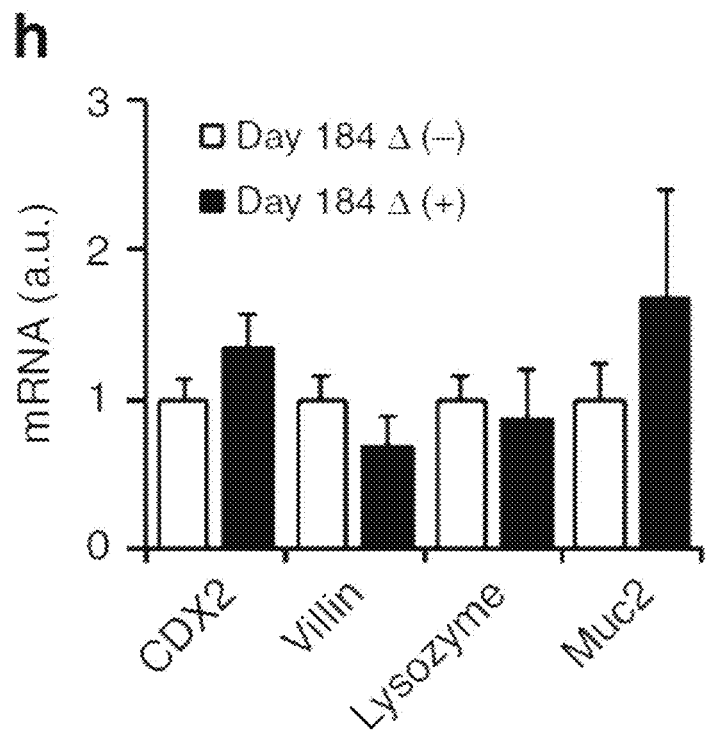
FIG. 5H-J, qPCR analysis in 184-day-old gut organoids transduced with control (empty bars) or HA-A256 adenovirus (black bars) of transcripts encoding (H) intestinal lineage markers, (I) intestinal stem cell and pan-secretory lineage markers, and (J) genes associated with Notch signaling.
Figure 5I:
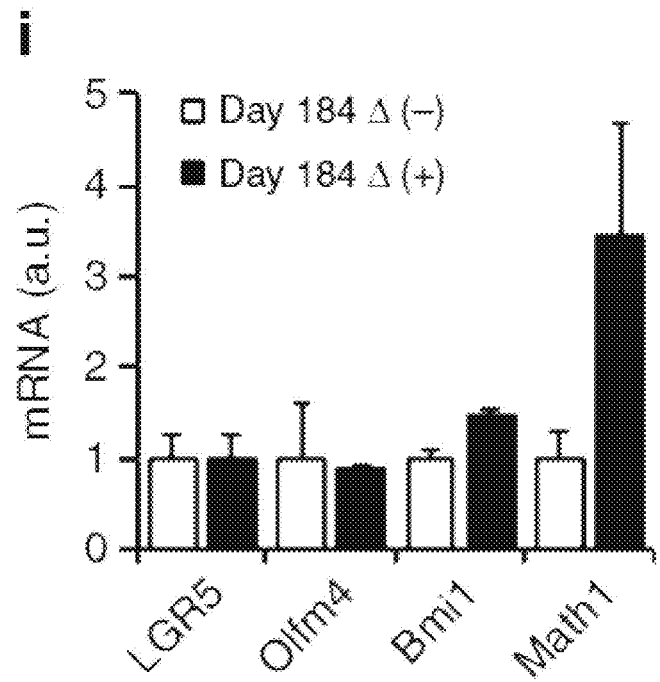
Figure 5J:
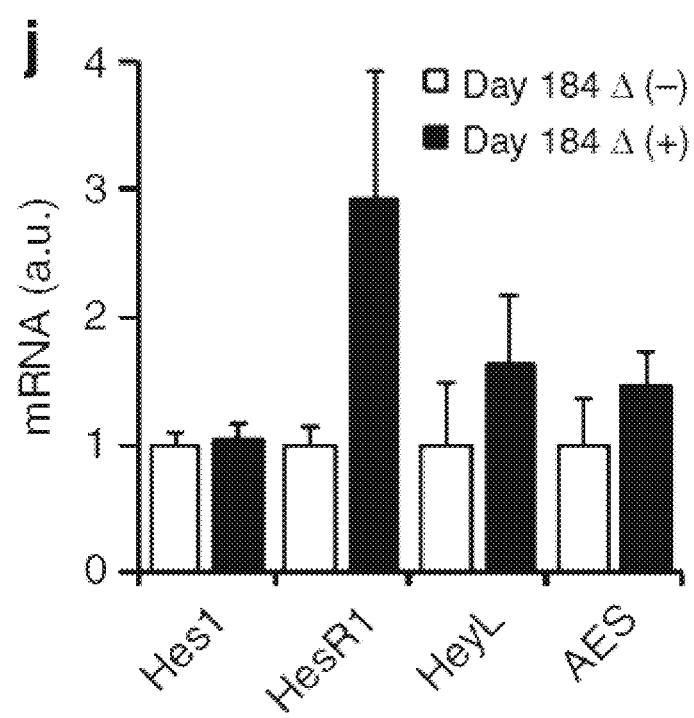

Pancreatic Beta Cell Markers are Seen in Human in Insulin+ Cells in Human Gut Organoids Insulin-producing cells obtained from ES or iPS differentiation are often polyhormonal (1), but investigation into Gut insulin+ cells found no evidence that they express other endocrine markers, including GLP1, somatostatin (FIG. 5F-G), glucagon, and PP. FOXO1 loss-of-function did not affect levels of transcripts encoding intestinal stem and pan-secretory markers, including Notch25 (FIG. 5H-J).

Marker Analysis of Insulin-Immunoreactive Cells in Cells Transduced with HA-Δ256

Figure 6A:
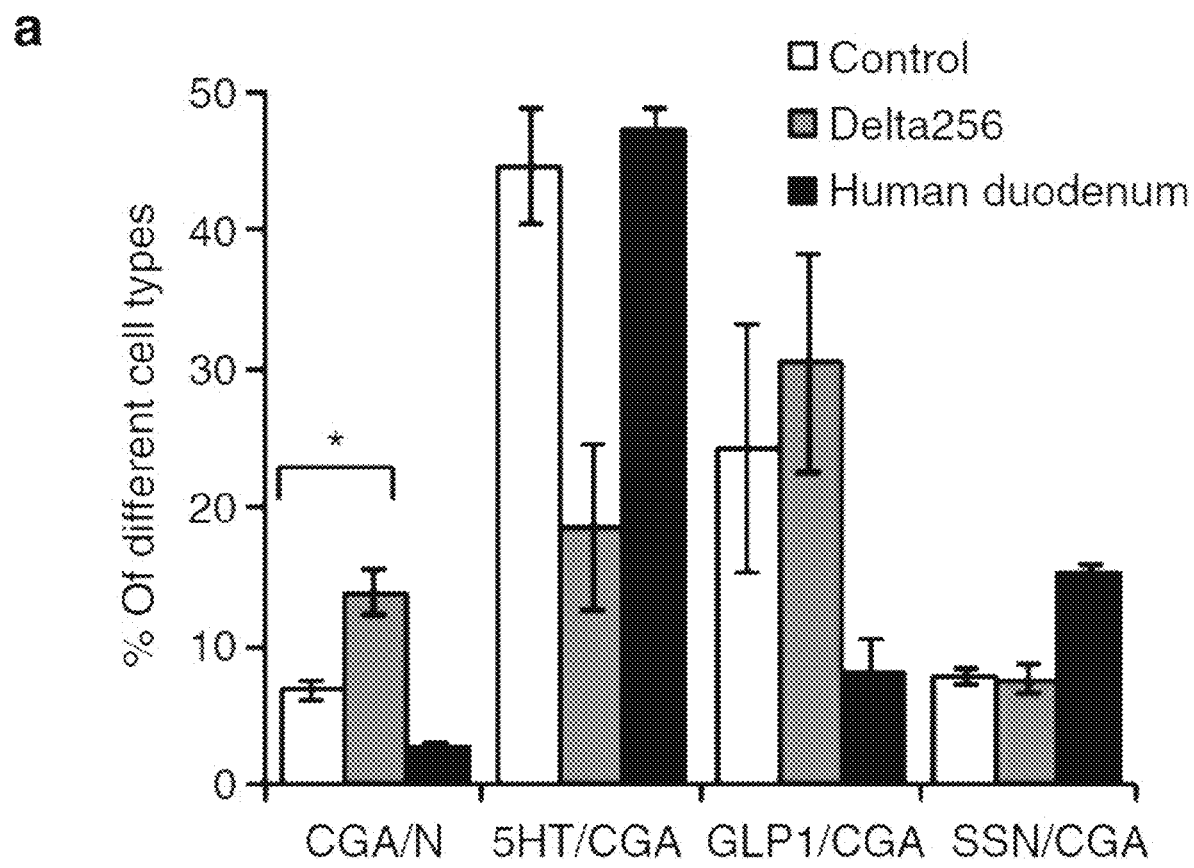
FIG. 6A, Quantification of cells expressing CGA, 5HT, GLP1 and SSN in 230-day-old gut organoids transduced with control (empty bars), HA-Δ256 FOXO1 adenovirus (gray bars), or human duodenum (black bars).
Figures 6B, 6C:
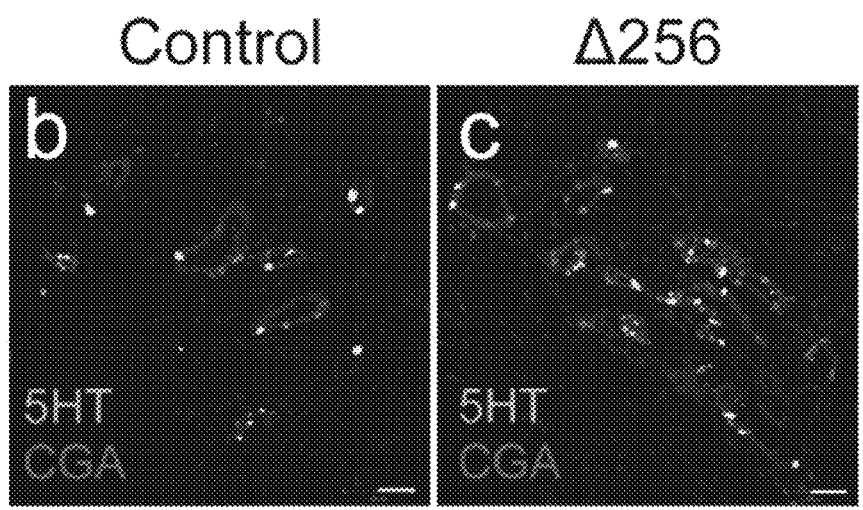
FIG. 6B-D, Immunohistochemistry with 5HT (green) and CGA (red) in 230-day-old gut organoids transduced with HA-Δ256 FOXO1 (1) or control adenovirus (m).
Figures 6D, 6E:
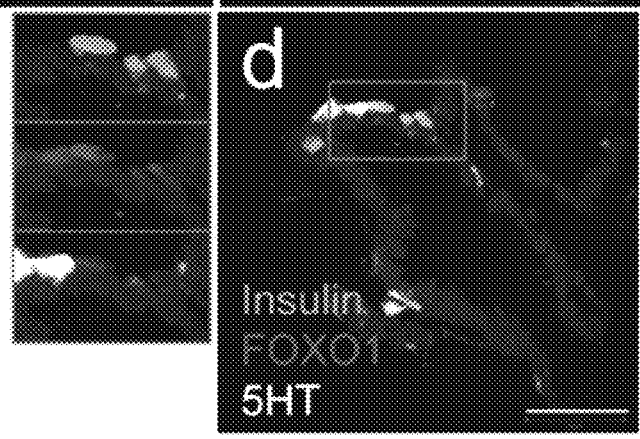
FIG. 6E, Immunohistochemistry of insulin (green), FOXO1 (red) and 5HT (white) in 230-day-old gut organoids transduced with HA-Δ256 FOXO1 adenovirus. Insets on the left show magnifications of a cluster of 5HT-, FOXO1-, and insulin-positive cells. Scale bars: 50 μm (n=3 for histology and qPCR) (*p<0.05 vs. organoids transduced with control shRNA lentivirus or HA-Δ256 adenovirus). Data is presented as means±SEM.
Figure 7A:
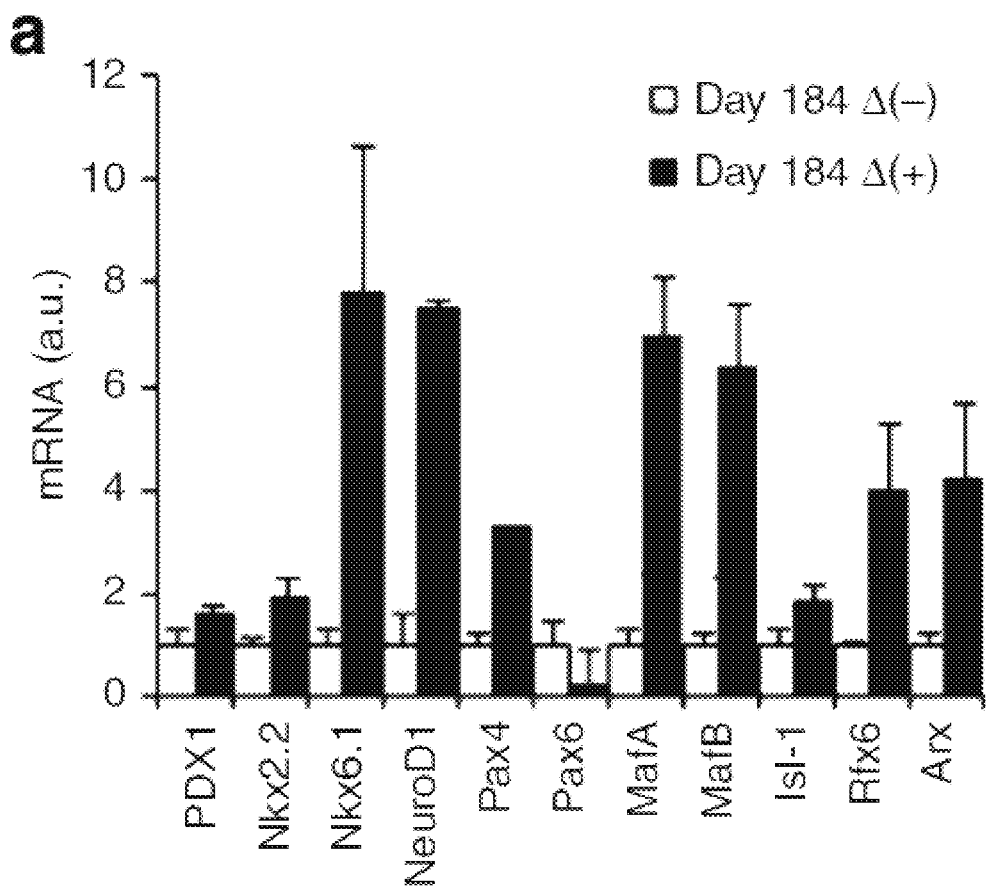
FIG. 7A-C, qPCR analysis of transcripts of markers associated with β-cell specification and maturation in organoids transduced with control (empty bars) or HA-Δ256 FOXO1 adenovirus (black bars).
Figure 7B:
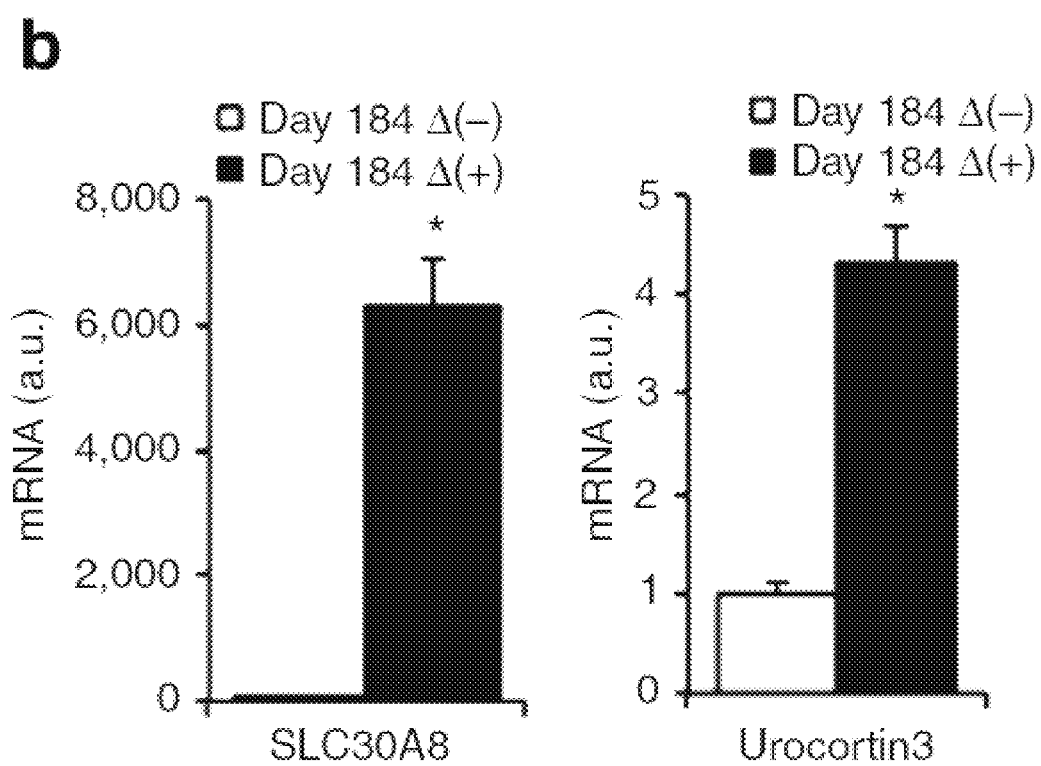
Figure 7C:
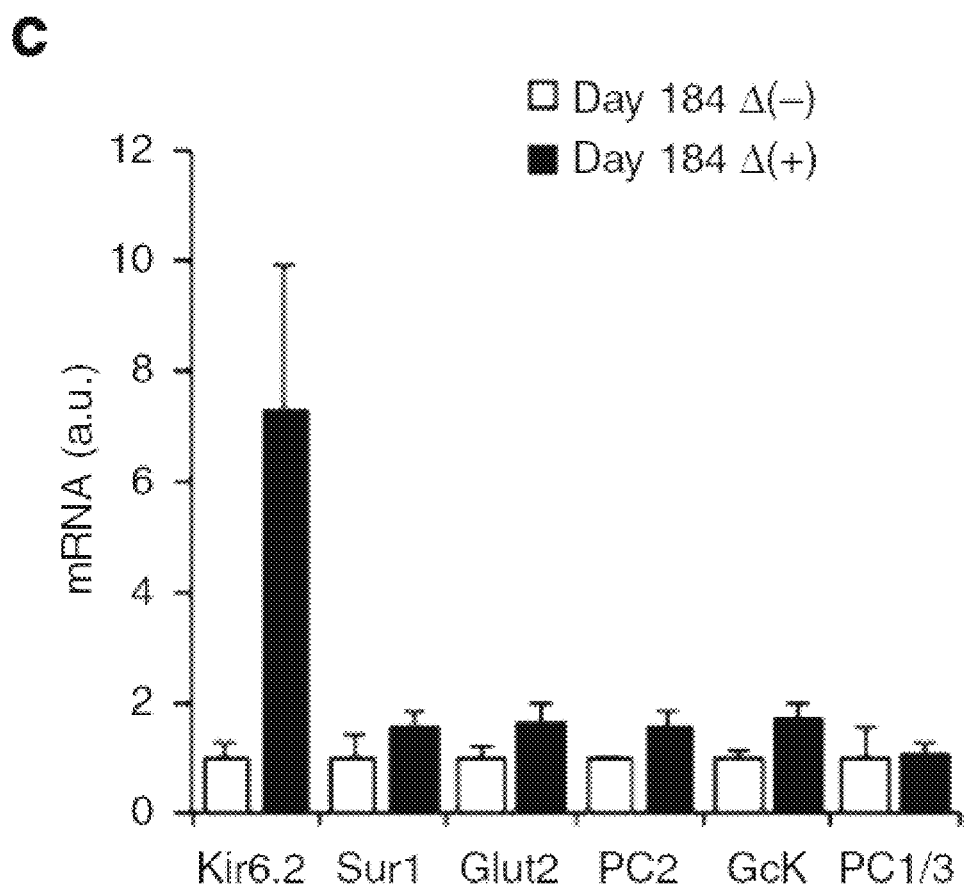
Figure 7F:
FIG. 7: Pancreatic marker analysis in 184-day-old gut organoids.
FIG. 7D-R, Colocalization of insulin (green) with (D-F) MAFA (The inset in panel e shows green MafA immunoreactivity in human pancreatic islets), (G-H) Urocortin-3, (I-J) PC2, (K-L) SUR1, (M-N) PC1/3, (O-P) glucokinase, and (Q-R) glucose transporter 2 (all in red). Scale bars: 50 μm in d-r (n=3-6 for qPCR, 3 for histochemistry) (*p<0.05 vs. organoids transduced with control virus). Data is presented as means±SEM.
Figure 7I:
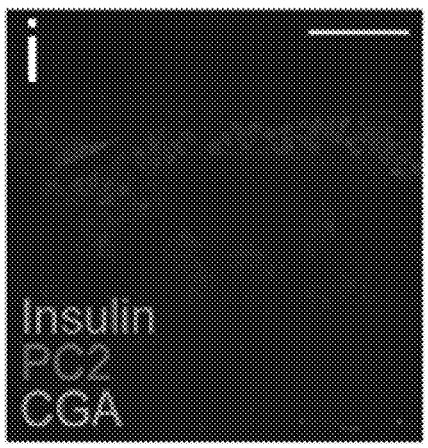
Figure 7J:
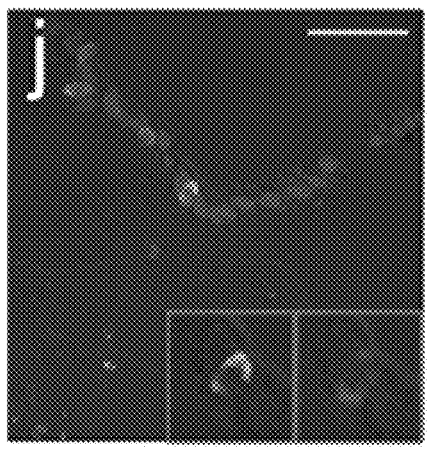
Figure 7K:
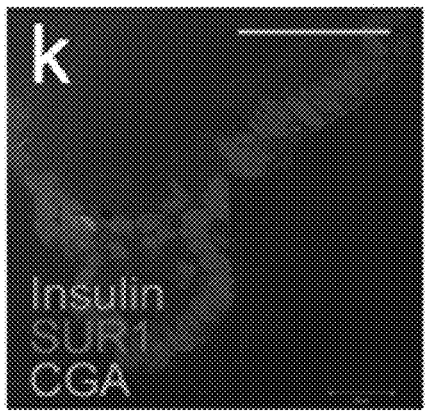
Figure 7L:
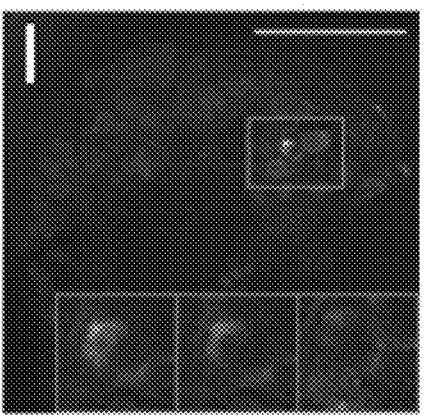
Figure 7M:
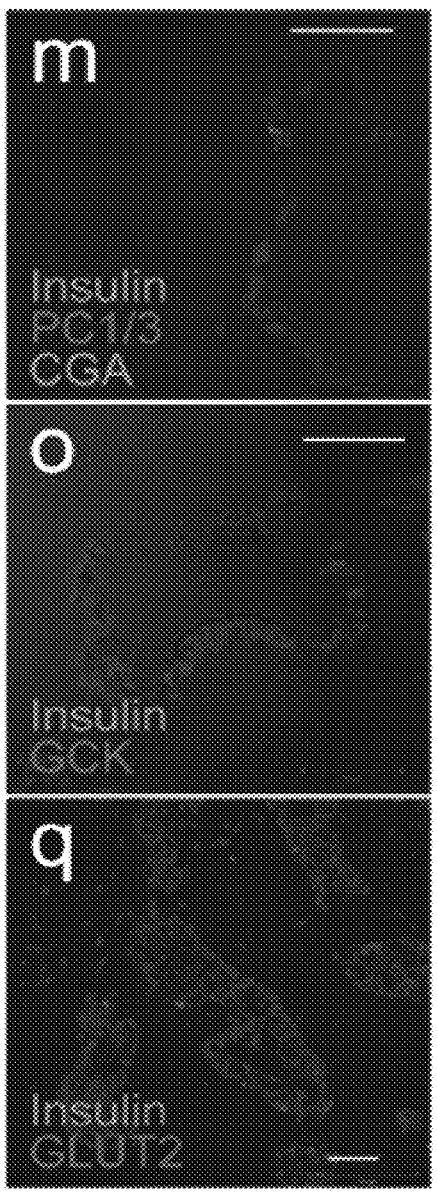
Figure 7N:
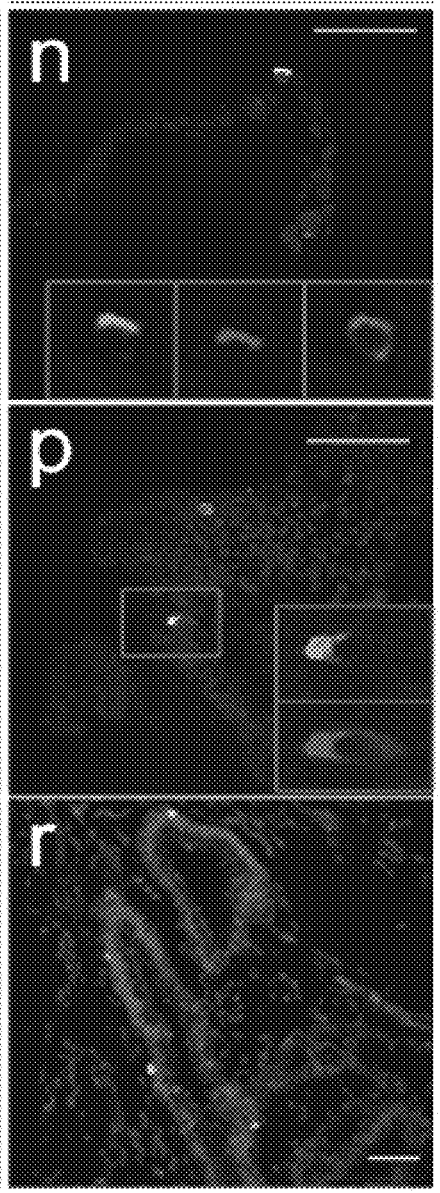
Figure 7O:
Figure 7P:
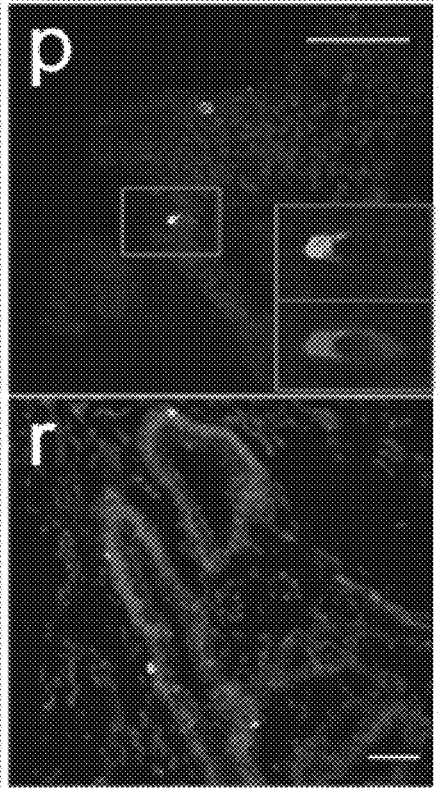
Figure 7Q:
Figure 7R:
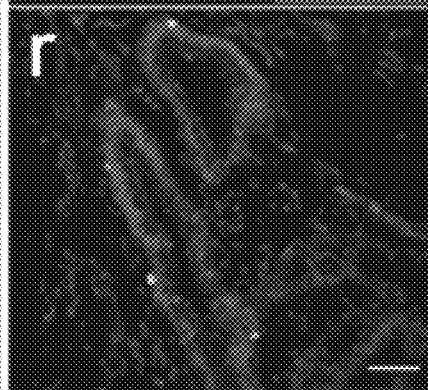

Analysis of markers of β-cell differentiation showed that transduction with HA-Δ256 significantly increased transcripts of genes involved in β-cell specification and maturation in 184-day-old gut organoids (FIG. 6A-C and Supplementary Table 4). It should be noted that NKX2.2, NKX6.1, and NEUROD transcripts were 10- to 100-fold less abundant than those of other transcription factors (Supplementary Table 3). Immunohistochemistry confirmed that insulin-positive cells were positive for MAFA and UROCORTIN3 (FIG. 6D-H). The induction of MAFA—as noted above for that of MAFB—is remarkable, not having been observed in endoderm-derived β-like-cells[1-3]. Insulin-positive cells scored positive for all tested markers of pancreatic β-cells, including PC2, SUR1, PC1/3, glucokinase (GCK), and glucose transporter 2 (GLUT2) (FIG. 6I-R)[22,26].

FOXO1 Inhibition was Associated with a Dramatic Reduction in Serotonin Expression in Insulin+ Cells FOXO1 is predominantly expressed in 5HT cells, and conversion to insulin-immunoreactive cells following FOXO1 loss-of-function was associated with a dramatic reduction in 5HT expression. 230-day-old-organoids transduced with HA-Δ256 adenovirus showed an increase in the frequency of CGA-positive cells by ~twofold, and a dramatic decrease in the number of CGA/5HT-positive cells in insulin+ organoid cells by ~60% (p<0.05) (FIG. 7A-D). This reduction in serotonin occurred even though there was a concerted increase of the activity of the serotonergic pathway, including transcriptional regulators (FEV, LMX1A), 5HT-processing enzyme TPH2 (no changes to TPH1 were detected), 5HT transporters, and receptors. This in theory would be expected to increase 5HT levels. However, it was also found that FOXO1 loss of function resulted in a significant increase of ALHD1a3, the enzyme that catalyzes conversion of 5HT to 5HIAA.[16] Importantly, there is a similar effect of Foxo1 ablation in pancreatic β-cells of mice (not shown).

FIG. 6 *b-d* shows the immunohistochemistry with 5HT (green) and CGA (red) in 230-day-old gut organoids transduced with HA-Δ256 FOXO1 (l) or control adenovirus (m). As can be seen in FIG. 6 *b*, Foxo1 and 5HT are not seen in insulin+ cells.

Figure 11:
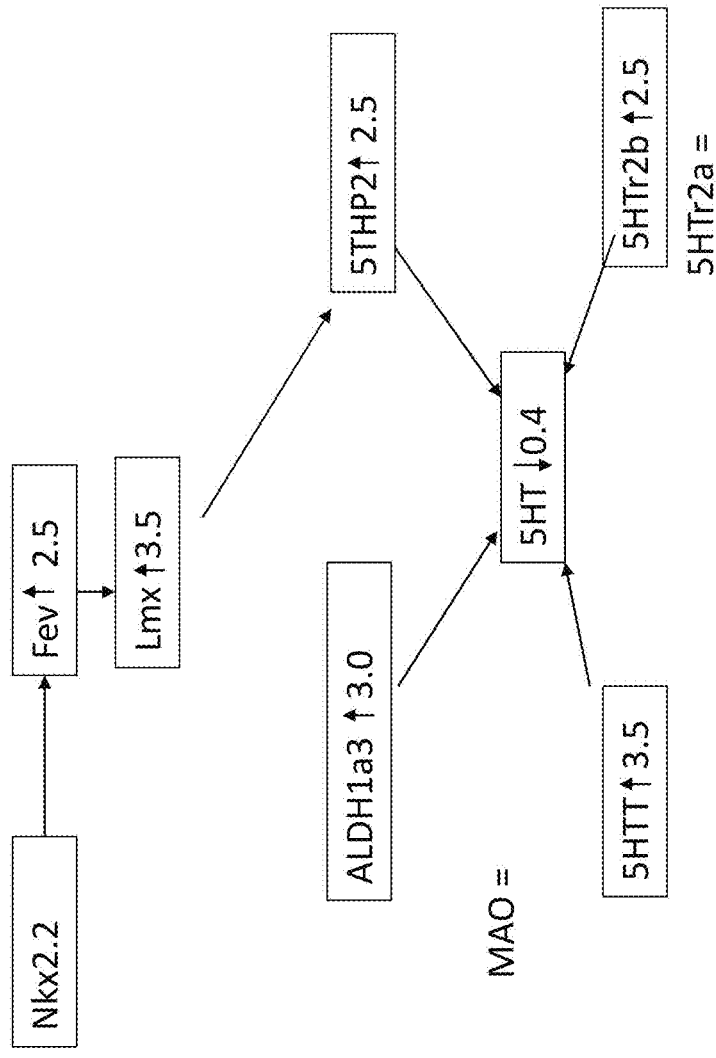
FIG. 11 provides a diagram showing that a 3.5 fold reduction in serotonin is associated with a 2.5 fold increase in the 5HTr2b receptor.

It was further discovered and is shown in FIG. 11, that a 3.5 fold reduction in serotonin is associated with a 2.5 fold increase in the 5HTr2b receptor. This increase in 5HTr2b is likely compensating for the reduction in serotonin, therefore contacting enteroendocrine cells with 5HTr2b antagonists will reduce intracellular serotonin signaling, which in turn will cause the cells to differentiate into insulin+ cells.

Figure 8A:
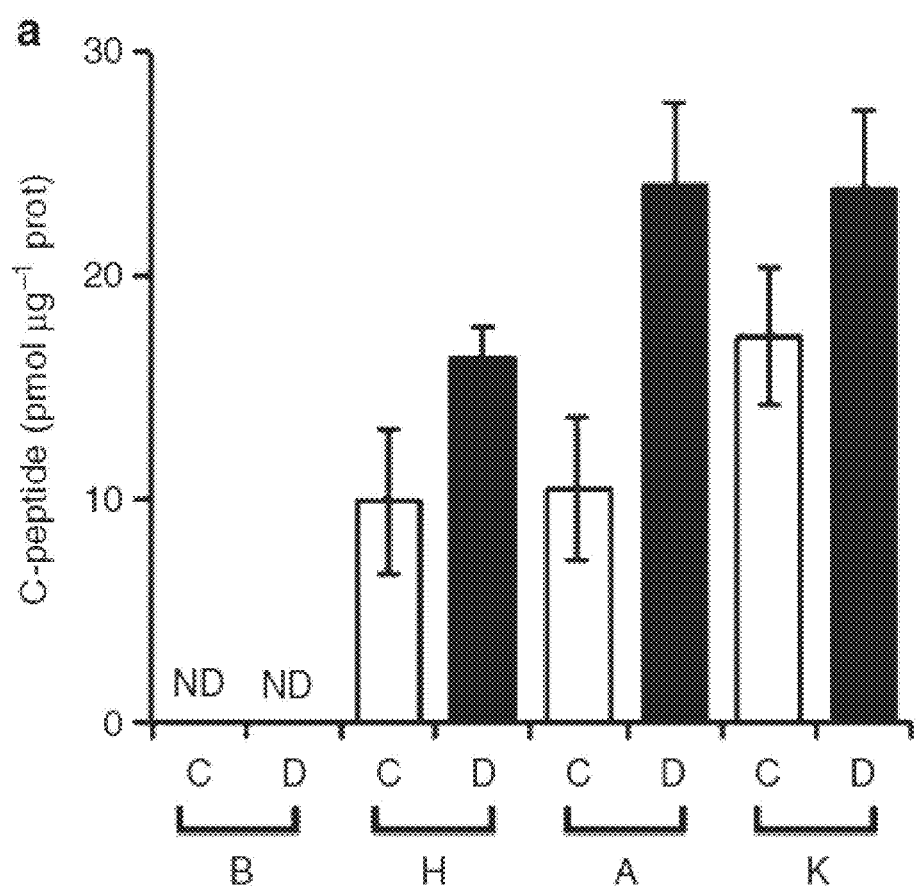
FIG. 8A, Human C-peptide release from gut organoids normalized by protein levels in organoid lysates. C: control adenovirus; D: HA-Δ256 FOXO1 adenovirus, B: basal glucose (2 mM); H: high glucose (22 mM); A: arginine (10 mM); K: KCl (30 mM); ND: not detected.
Figure 8B:
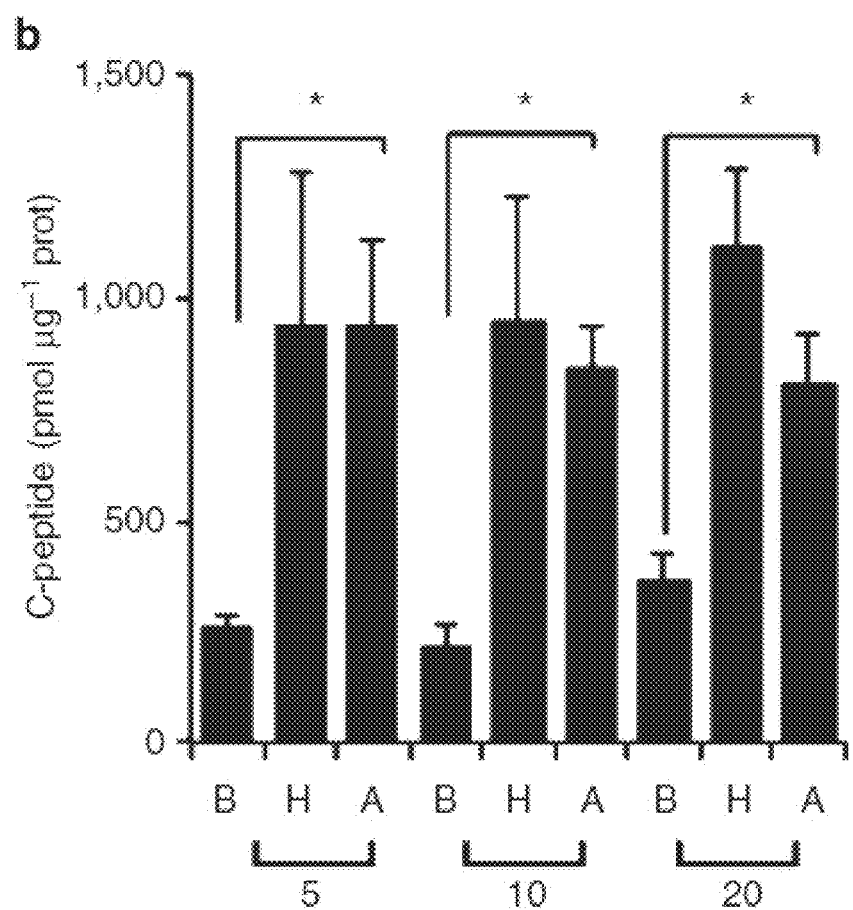
FIG. 8B, C-peptide secretion by human islets. Abbreviations are the same as in panel a. The numbers below the brackets refer to number of islets used.
Figure 8C:
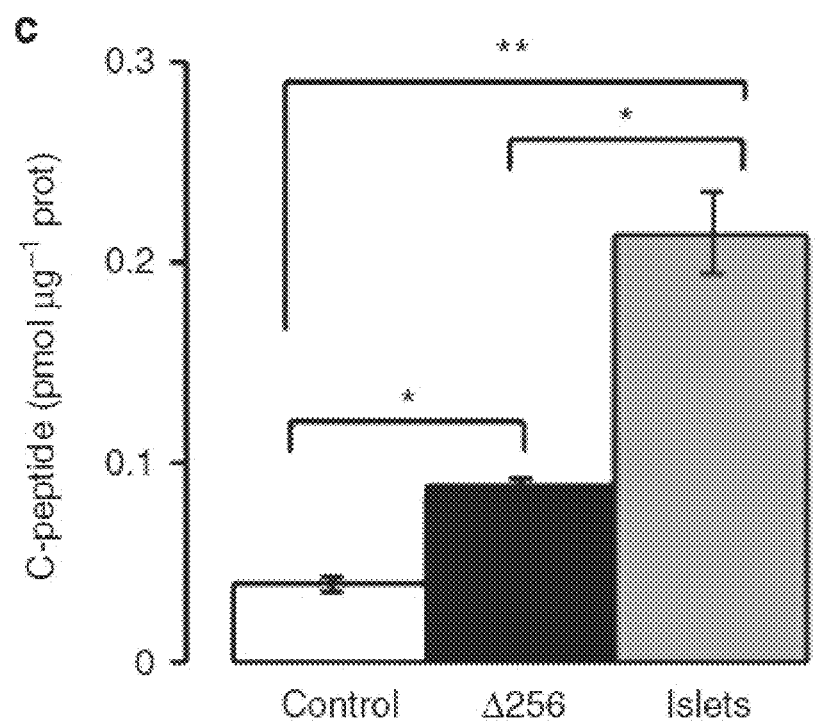
FIG. 8C, C-peptide content in gut organoids and human islets *p<0.05 vs. organoids transduced with control virus (panel c) or basal vs. glucose- and arginine-stimulated conditions (panel b) (**p<0.05 vs. human islets in panel c). Data is presented as means±SEM (n=3).

Insulin-Producing Cells in Human Gut Organoids Transduced with HA-Δ256 Release Insulin in Response to Different Secretagogues Insulin-positive cells in human 200 day-old gut organoids transduced with HA-Δ256 or control adenovirus with glucose, arginine or KCl have the ability to release insulin in a regulated manner. Under basal conditions, C-peptide was undetectable in organoids. However, it rose to levels between 10 and 20 pmol/µg protein in response to 22 mM glucose in both control and HA-Δ256 organoids, respectively (p<0.05). Likewise, there was a robust response to arginine and to the depolarizing agent, KCl. In both instances, HA-Δ 256 organoids showed a significantly greater response than controls (FIG. 8A). In parallel experiments with collagenase-purified human islets, it is estimated that 40 organoids transduced with HA-Δ 256 (or 70 untransfected organoids) secrete as much C-peptide as 1 human islet (FIG. 8B). Given the heterogeneity of cellular composition and viability in donor-derived human islets, and in organoids, it is difficult to compare insulin content per cell between the two systems. However, when normalized by protein content, C-peptide secretion in control and HA-Δ256 organoids was 1.0% and 1.6% of human islets, respectively (FIG. 8A-B). C-peptide content was significantly higher in gut organoids transduced with HA-Δ256 adenovirus compared with controls (FIG. 8C) (p<0.05).

Figures 9A, 9B, 9C, 9D, 9E, 9F, 9G, 9H:
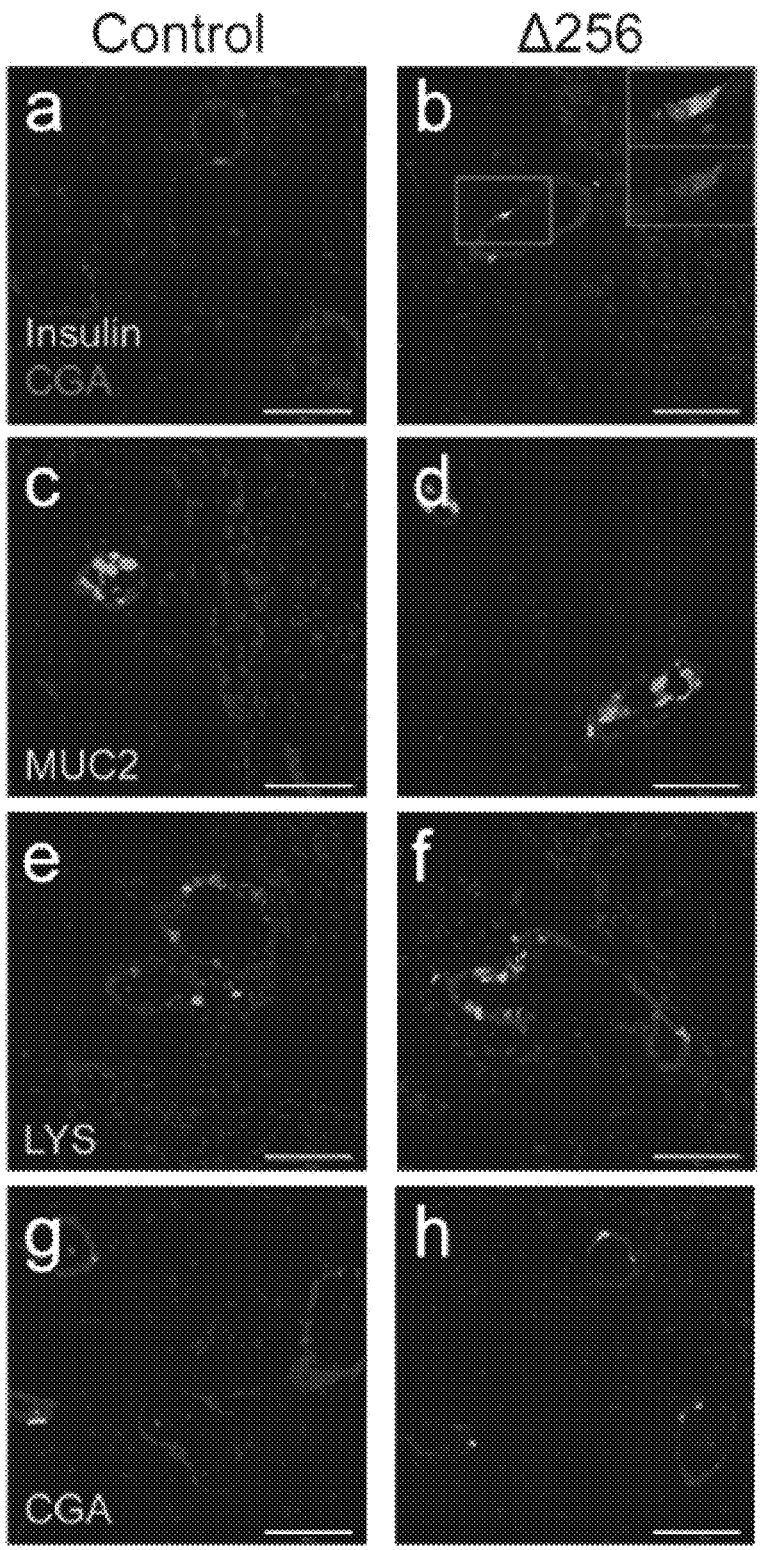
FIG. 9 Immunohistochemistry of insulin and intestinal lineage markers in 200-day-old gut organoids recovered three weeks following transplantation into immunodeficient mice. a-b, insulin (green) and CGA (red); c-d, MUC2; e-f, LYS; and g-h, CGA (green). Scale bars: 100 (n=3).

Transplantation into immunodeficient mice improved the function of endoderm-derived pancreatic β-like-cells[2,3]. To study the effect of transplantation on 200-day-old gut organoids grafts were maintained for three weeks, and at the end of this time they retained an epithelial structure and demonstrated all intestinal lineages, including insulin-positive cells (FIG. 9). The number and proportion of β-like cells was similar to pre-transplantation organoids, indicating that no significant proliferation or cell death had occurred in vivo (FIG. 9). 200-day-old gut organoids transduced with control or HA-Δ256 FOXO1 adenovirus (10 organoids in each group, n=3) were transplanted under the skin of immunodeficient NOD.Cg-Prkdcscid Il2rgtm1Wjl/SzJ mice (005557; The Jackson Laboratory), using biocompatible "Gelfoam" Dental sponges (size 4) to preserve the anatomy. Three weeks after transplantation, organoids were recovered and used in the experiment described above.

Insulin-positive gut organoid cells generated by FOXO1 inhibition displayed several important features making them suitable for administration/implantation to treat any of the enumerated diseases. These features are expected to be seen in Insulin-positive gut organoid cells generated by significantly reducing serotonin expression, biosynthesis, signaling or biological activity, with or without treating the cells to inhibit FOXO1: (1) they express markers of terminally differentiated β-cells, such as MAFA, that have proved thus far resistant to induction in endoderm-derived β-like-cells[(1)]; (2) they secrete insulin in a strictly stimulus-dependent manner, and (3) they survive following in vivo transplantation.

SUMMARY

FOXO1 immunoreactivity in the human gut is known to be restricted to endocrine progenitor and serotonin-producing cells, the latter arguably being the closest endocrine cell type to insulin-producing pancreatic β-cells[10, 17] The data presented here and the figures shows that human iPS-derived gut organoids in which FOXO1 is inhibited by at least 50%, yield insulin+ cells that secrete biologically active insulin (C-peptide) in response to physiologic stimuli. These cells are present at low frequency in "old" organoids (i.e., kept in culture for >6 months), therefore to optimize the frequency of insulin+ cells, organoids less than about 3 months old should be used.

Insulin+ enteroendocrine cells made from human cells as described herein by reducing serotonin with or without also reducing FOXO1 intended for transplantation can be autologous to a subject in need of treatment, such as a subject with Type 1 diabetes, thereby dramatically reducing the risk of rejection. These herein described insulin+ cells enteroendocrine cells obtained from human gut organoids have the advantage of rapid turnover that makes them outrun immune attack in type 1 diabetes, and establishes a reservoir of self-renewing progenitors that would replenish shed cells. There are many recent advances in manipulating gut stem cells[18] and their potential use for gut transplantation[19] that will permit a person of skill in the art to manipulate and optimize the human gut organoid cultures to produce insulin+ cells suitable for transplantation/administration to individuals having type 1 or type 2 diabetes.

| GENE ID NUMBERS FOR FOXO GENES AND mRNA | | | | |
|---|---|---|---|---|
| Gene symbol FOXO1 Alternate Symbols: Afxh, FKHR, Fkhr1, Foxo1a Organism: Mouse Gene Id: 56458 Gene Name: forkhead box O1 Accession Numbers: NM_019739 | Gene Symbol: FOXO1 Alternate Symbols: FKH1, FKHR, FOXO1A Organism: Human Gene Id: 2308 Gene Name: forkhead box O1 Accession Numbers: NM_002015 | Gene Symbol: Foxo1 Alternate Symbols: Fkhr, Foxo1a Organism: Rat Gene Id: 84482 Gene Name: forkhead box O1 Accession Numbers: XM_001056726; XM_342244 | Gene Symbol: Foxo3 Alternate Symbols: 1110048B16Rik, 2010203A17Rik, C76856, FKHRL1, Fkhr2, Foxo3a Organism: Mouse Gene Id: 56484 Gene Name: forkhead box O3 Accession Numbers: NM_019740 | Gene Symbol: FOXO3 Alternate Symbols: AF6q21, DKFZp781A0677, FKHRL1, FKHRL1P2, FOXO2, FOXO3A, MGC12739, MGC31925 Organism: Human Gene Id: 2309 Gene Name: forkhead box O3 Accession Numbers: NM_001455; NM_201559 |
| Gene Symbol: FOXO4 Alternate Symbols: AFX, AFX1, MGC120490, MLLT7 Organism: Human Gene Id: 4303 Gene Name: forkhead box O4 Accession Numbers: NM_005938 | Gene Symbol: Foxo4 Alternate Symbols: afx, Afxh, Foxo4, Afxh, MGC117660, Mllt7 Organism: mouse Gene Id: 54601 Gene Name: forkhead box O4 Accession Number NM_019739.3 | Gene Symbol: Foxo4 Alternate Symbols: LOC302415, RGD1561201 Organism: Rat Gene Id: 302415 Gene Name: forkhead box O4 Accession Number NM_001106943.1. | Gene Symbol: Foxo3 Alternate Symbols: Fkhrl1, Foxo3a Organism: Rat Gene Id: 294515 Gene Name: forkhead box O3 Accession Numbers: NM_001106395 | |

*Homo sapiens* forkhead box O1 (FOXO1), mRNA NCBI Reference Sequence: NM_002015.3

*Mus musculus* forkhead box O1 (Foxo1), mRNA NCBI Reference Sequence: NM_019739.3

*Rattus norvegicus* forkhead box O1 (Foxo1), mRNA NCBI Reference Sequence: NM_001191846.1

*Homo sapiens* forkhead box 03 (FOXO3), transcript variant 1, mRNA NCBI Reference Sequence: NM_001455.3

*Homo sapiens* forkhead box 03 (FOXO3), transcript variant 2, mRNA NCBI Reference Sequence: NM_201559.2

*Mus musculus* forkhead box 03 (Foxo3), mRNA NCBI Reference Sequence: NM_019740.2

*Rattus norvegicus* forkhead box 03 (Foxo3), mRNA NCBI Reference Sequence: NM_001106395.1 Homo In our previous work, Matsumoto et al The Journal of Clinical Investigation, Volume 116 Number 9 Sep. 2006, shRNA was used to reduce Foxo1 expression by targeting the sequence GCACCGACTTTATGAGCAACC SEQ ID NO: 1 of Foxo1 using short-hairpin RNA (from BD Biosciences) as a control siRNA target sequence. Because of the sequence homology, this sequence or a substantially homologous sequence in human FOXO1 may be a good target. Liu et al., Cancer Gene Therapy 14, 945-952 December 2007 also describe using RNA inhibitors in mice to reduce expression of Foxo1 in skeletal muscle. Labied, S, et al. Molecular Endocrinology 20(1):35-44, provides a description of antisense molecules that inactivate various human FOXO proteins, including: FOXO1-antisense (TTG GGT CAG GCG GTT CA SEQ ID NO: 2); FOXO3a-sense (CCC AGC CTA ACC AGG GAA GT SEQ ID NO: 3) and FOXO3a-antisense AGC GCC CTG GGT TTG G SEQ ID NO: 4); FOXO4-sense (CCT GCA CAG CAA GTT CAT CAA SEQ ID NO: 5) and FOXO4-antisense (TTC AGC ATC CAC CAA GAG CTT SEQ ID NO: 6). S. Stephen, et al., Cancer Research 70, 367, Jan. 1, 2010, describes using microRNA (miR) target prediction algorithms, to identify several miRs that bound to the 3'-untranslated region (UTR) of FOXO1 transcripts in human endometrial cancer cell lines thereby inhibiting FOXO1 expression. These inhibitory oligonucleotides can be used in certain embodiments of the present invention.

6. Methods Related to Experimental Results Section (5)

Intestinal Samples.

Specimens of duodenum, jejunum, ileum, and colon were obtained from patients undergoing intestinal resection procedures or from pancreatic organ donors. Informed consent was obtained from individuals or relatives who donated tissue for this study. Samples were processed immediately for paraffin embedding by formalin fixation or for frozen section preparation, as described below. The Columbia University IRB has approved all procedures.

Immunohistochemistry.

Gut organoids were isolated from Matrigel, rinsed in PBS, and fixed in 4% phosphate-buffered paraformaldehyde for 15 min at room temperature. Human gut specimens were fixed in the same buffer overnight. After fixation, organoids or gut specimens were incubated in 30% phosphate-buffered sucrose overnight at 4° C. and embedded into Cryomold (Sakura Finetek) for subsequent frozen block preparation. 6 μm-thick sections were cut from frozen blocks and incubated with HistoVT One, using Blocking One (both from Nacalai USA) to block nonspecific binding[8]. Sections were incubated with primary antibodies for 12 h at 4° C., followed by incubation with secondary antibodies for 30 min at room temperature. (Catalog numbers and dilutions used for each antibody are reported in Supplementary Table 1.) Alexa-conjugated donkey and goat secondary antibodies (Molecular Probes) were used. After the final wash, cells were viewed using a confocal microscopy (Zeiss LSM 710). DNA was counterstained with DAPI (Cell Signaling). For immunostaining of human gut, 100 sets of villi and crypts that could be viewed longitudinally were surveyed and the number and position of enteroendocrine and FOXO1-positive cells were counted. In 3 independent experiments in human duodenum, 2.8±0.3 CGA-positive, and 2.1±0.4 FOXO1-positive cells/set of villi and crypts were found. For immunohistochemistry of 200-day-old gut organoids transduced with control and 4256-HA adenovirus, at least 5 organoids were pooled, containing on average 5087±328 and 4222±851 nuclei, 346±35 and 615±225 CGA-positive cells in one section, respectively (n=3). For immunohistochemistry of 230-day-old organoids transduced with shRNA lentivirus, at least 5 organoids were scored for each virus. Each organoid contained an average of 4546±556 and 4099±646 nuclei in experiments with the control and FOXO1 shRNA (n=3). In each experiment, 224±32 and 193±36 FOXO1-positive cells, and 2.0±1.0 and 16.0±3.1 insulin-positive cells, respectively, were detected.

Fluorescent tracers for use in the embodiments include GFP and derivatives, Diamidino yellow, Fast blue, Horseradish peroxidase, Cholera toxin B, Pseudorabies virus, Hydroxystilbamidine, Texas Red, and Fluorescein isothiocyanate, and any others known in the art. Green fluorescent protein (GFP) was used in the experiments described herein, however there are now many different mutants of GFP (Shaner N, Steinbach P, Tsien R [2005] "A guide to choosing fluorescent proteins," *Nat Methods* 2 [12]: 905-9). A list of various fluorescent proteins can be found at http://ni-c.ucsf.edu/dokuwiki/doku.php?id=fluorescent_proteins.

Cell Culture.

Human iPS cells were generated from fibroblast of three healthy control subjects as previously described[3,4]. Briefly, upper arm skin biopsies were obtained from healthy subjects using local anesthesia. The biopsies were processed as described and placed in culture medium containing DMEM, fetal bovine serum, GlutMAX, and Penicillin/Streptomycin (all from Invitrogen) for 4 weeks3. The CytoTune-iPS Sendai Reprogramming Kit (Invitrogen) was used to convert primary fibroblasts into pluripotent stem cells using 50,000 cells per well in 6-well dishes. Cells were grown in human ES medium3. The Columbia University Institutional Review Board has approved all procedures. iPS cells were cultured in MTeSR (Stemgent) on Matrigel (BD Biosciences)-coated plates and passaged according to the manufacturer's instructions.

Generation of Gut Organoids.

Human iPS cells were differentiated into gut organoids as described[23] with some modifications. STEMdiff™ Definitive Endoderm Kit (Stemcell Technologies) was used instead of Activin A for differentiation towards definitive endoderm. Gut organoids were passaged every 2-3 weeks until 360 days; the morphology was assessed periodically using immunohistochemistry. Organoids from 3 different iPS cell lines were prepared all experiments were performed using at least 3 independent biological replicates. In each biological replicate at least 5 organoids were used for immunohistochemistry and at least 3 organoids for qRT-PCR.

Adenovirus and Lentivirus Transduction.

The recombinant adenoviral vector Ad-CMV-FOXO1-Δ256 expressing a mutant version of FOXO1 containing its amino domain (corresponding to amino acid residues 1-256) has been described[24]. Adenoviruses were prepared by CsCl density centrifugation to a titer of 2.5×1012 viral particles/ml (1.6×1011 plaque-forming units/ml) for Ad-CMV-FOXO1-A256, and 2.4×1012 viral particles ml (1.9×1011 pfu/ml) for the Gfp control. Gut organoids were mechanically dissociated from Matrigel, cut in half and incubated in DMEM/F12 containing 10 ⌈M ROCK inhibitor (Y27632) with 1 ⌈l of adenovirus solution for 3 hours at 37° C. in a 5% CO2 incubator and then washed with PBS three times. After transduction, mini-guts were embedded into fresh Matrigel again and incubated with intestinal growth medium[23]. For lentiviral experiments, human GIPZ lentiviral FOXO1 shRNA plasmids were purchased (Clone ID; V3LHS_405827, 638215, 638212, 638211, Thermo Scientific) and transfected in 293 FT cells (Invitrogen) with packaging mix plasmids (Thermo Scientific) using Lipofectamine™ 2000 (Invitrogen). Plasmids were diluted by Opti-MEM, and Lipofectamine™ 2000 was added and incubated at room temperature for 20 min. After incubation, the mixture was added to 293 FT cells. Viral supernatants were collected 48 and 72 h after transfection and centrifuged at 6,000 rpm×2 hr to concentrate them.

Organoid Transplantation.

200-day-old gut organoids transduced with control or HA-Δ256 FOXO1 adenovirus (10 organoids in each group, n=3) were transplanted under the skin of immunodeficient NOD.Cg-Prkdcscid Il2rgtm1Wjl/SzJ mice (005557; The Jackson Laboratory), using biocompatible "Gelfoam" Dental sponges (size 4) to preserve the anatomy. Three weeks after transplantation, organoids were recovered and immunostaining performed as described above.

RNA Isolation and RT-PCR.

Standard methods of RNA extraction and qRT-PCR (Invitrogen) were used. Primer sequences are listed in Supplementary Table 2.

C-Peptide Assay.

200-days-old organoids were incubated in serum-free medium for 3 days prior to the experiment. For each determination, 10 organoids were incubated in 1 mL of Krebs-Ringer buffer containing 10 mM HEPES, 1.19 mM MgSO4, 119 mM NaCl, 4.74 mM KCl, 1.19 mM KH2PO4, 2.54 mM CaCl2-2H2O, 25 mM $NaHCO_3$, 1% BSA) and 2.0 mM glucose, at 37° C. for 30 min before the medium was replaced and the incubation continued for 30 min. This medium was collected for basal determination. Subsequently, 1 mL of Krebs-Ringer buffer containing 22 mM glucose, or 10 mM arginine, or 30 mM KCl was added and the organoids incubated at 37° C. for 30 min, after which the medium was collected. At the end of final incubation, the organoids were lysed by buffer containing 2% SDS, 50 mM Tris-HCl, 5 mM EDTA, and protease/phosphatase inhibitors (Thermo Scientific), the extract sonicated and clarified by centrifugation. C-peptide secretion and intracellular content of organoids were measured using an ultrasensitive human C-peptide ELISA kit (Mercodia) and protein in lysate was measured using Pierce BCA Protein Assay Kit (Thermo Scientific). C-peptide release by protein levels in lysates of gut organoids (pmol/⌈g protein) was normalized.

Statistical Analysis.

Paired or unpaired t-test was used to determine statistical significance between two groups and one-way ANOVA for group comparison, with post-hoc Bonferroni correction, as appropriate. The customary threshold of p<0.05 was used to declare a statistically significant difference.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

The invention is illustrated herein by the experiments described above and by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

REFERENCES

1. Schulz, T. C., et al. A scalable system for production of functional pancreatic progenitors from human embryonic stem cells. *PLoS One* 7, e37004 (2012).
2. Blum, B., et al. Functional beta-cell maturation is marked by an increased glucose threshold and by expression of urocortin 3. *Nature biotechnology* 30, 261-264 (2012).
3. Hua, H., et al. iPSC-derived beta cells model diabetes due to glucokinase deficiency. *J Clin Invest* 123, 3146-3153 (2013).
4. Maehr, R., et al. Generation of pluripotent stem cells from patients with type 1 diabetes. *Proc Natl Acad Sci USA* 106, 15768-15773 (2009).
5. Schonhoff, S. E., Giel-Moloney, M. & Leiter, A. B. Minireview: Development and differentiation of gut endocrine cells. *Endocrinology* 145, 2639-2644 (2004).
6. Talchai, C., Xuan, S., Kitamura, T., Depinho, R. A. & Accili, D. Generation of functional insulin-producing cells in the gut by Foxo1 ablation. *Nat Genet* 44, 406-412 (2012).
7. Habib, A. M., et al. Overlap of endocrine hormone expression in the mouse intestine revealed by transcriptional profiling and flow cytometry. *Endocrinology* 153, 3054-3065 (2012).
8. Talchai, C., Xuan, S., Lin, H. V., Sussel, L. & Accili, D. Pancreatic beta Cell Dedifferentiation as a Mechanism of Diabetic beta Cell Failure. *Cell* 150, 1223-1234 (2012).
9. Thorel, F., et al. Conversion of adult pancreatic alpha-cells to beta-cells after extreme beta-cell loss. *Nature* 464, 1149-1154 (2010).
10. Xu, X., et al. Beta cells can be generated from endogenous progenitors in injured adult mouse pancreas. *Cell* 132, 197-207 (2008).
11. Accili, D. & Arden, K. C. FoxOs at the crossroads of cellular metabolism, differentiation, and transformation. *Cell* 117, 421-426 (2004).
12. Spence, J. R., et al. Directed differentiation of human pluripotent stem cells into intestinal tissue in vitro. *Nature* 470, 105-109 (2011).
13. van der Flier, L. G., Haegebarth, A., Stange, D. E., van de Wetering, M. & Clevers, H. OLFM4 is a robust marker for stem cells in human intestine and marks a subset of colorectal cancer cells. *Gastroenterology* 137, 15-17 (2009).

14. Villasenor, A., et al. EphB3 marks delaminating endocrine progenitor cells in the developing pancreas. *Dev Dyn* 241, 1008-1019 (2012).
15. Scoville, D. H., Sato, T., He, X. C. & Li, L. Current view: intestinal stem cells and signaling. *Gastroenterology* 134, 849-864 (2008).
16. Gradwohl, G., Dierich, A., LeMeur, M. & Guillemot, F. neurogenin3 is required for the development of the four endocrine cell lineages of the pancreas. *Proc Natl Acad Sci USA* 97, 1607-1611 (2000).
17. Schwitzgebel, V. M., et al. Expression of neurogenin3 reveals an islet cell precursor population in the pancreas. *Development* 127, 3533-3542 (2000).
18. Lee, C. S., Perreault, N., Brestelli, J. E. & Kaestner, K. H. Neurogenin 3 is essential for the proper specification of gastric enteroendocrine cells and the maintenance of gastriepithelial cell identity. *Genes Dev* 16, 1488-1497 (2002).
19. Ohta, Y., et al. Convergence of the insulin and serotonin programs in the pancreatic beta-cell. *Diabetes* 60, 3208-3216 (2011).
20. Gagnon, J., Mayne, J., Mbikay, M., Woulfe, J. & Chretien, M. Expression of PCSK1 (PC1/3), PCSK2 (PC2) and PCSK3 (furin) in mouse small intestine. *Regulatory peptides* 152, 54-60 (2009).
21. Fujita, Y., Asadi, A., Yang, G. K., Kwok, Y. N. & Kieffer, T. J. Differential processing of proglucose-dependent insulinotropic polypeptide in gut. *American journal of physiology. Gastrointestinal and liver physiology* 298, G608-614 (2010).
22. Nielsen, L. B., et al. Co-localisation of the Kir6.2/SUR1 channel complex with glucagonlike peptide-1 and glucose-dependent insulinotrophic polypeptide expression in human ileal cells and implications for glycaemic control in new onset type 1 diabetes. *Eur J Endocrinol* 156, 663-671 (2007).
23. McCracken, K. W., Howell, J. C., Wells, J. M. & Spence, J. R. Generating human intestinal tissue from pluripotent stem cells in vitro. *Nature protocols* 6, 1920-1928 (2011).
24. Nakae, J., Kitamura, T., Silver, D. L. & Accili, D. The forkhead transcription factor Foxo1 (Fkhr) confers insulin sensitivity onto glucose-6-phosphatase expression. *The Journal of clinical investigation* 108, 1359-1367 (2001).
25. Kitamura, T., et al. A Foxo/Notch pathway controls myogenic differentiation and fiber type specification. *The Journal of clinical investigation* 117, 2477-2485 (2007).
26. Cheung, A. T., et al. Glucose-dependent insulin release from genetically engineered K cells. *Science* 290, 1959-1962 (2000).
27. Ohara-Imaizumi, M., et al. Serotonin regulates glucose-stimulated insulin secretion from pancreatic beta cells during pregnancy. *Proc Natl Acad Sci USA* 110, 19420-19425 (2013).
28. Chen, Y. J., et al. De Novo Formation of Insulin-Producing "Neo-beta Cell Islets" from Intestinal Crypts. *Cell reports* 6, 1046-1058 (2014).
29. Pajvani, U. B., et al. Inhibition of Notch signaling ameliorates insulin resistance in a Fox01-dependent manner. *Nature medicine* 17, 961-967 (2011).
30. Kitamura, T., et al. The forkhead transcription factor Foxo1 links insulin signaling to Pdx1 regulation of pancreatic beta cell growth. *The Journal of clinical investigation* 110, 1839-1847 (2002).
31. Tanaka, H., et al. Effects of the novel Foxo1 inhibitor AS1708727 on plasma glucose and triglyceride levels in diabetic db/db mice. *Eur J Pharmacol* 645, 185-191 (2010).

Supplementary Tables

SUPPLEMENTARY TABLE 1

Primary antibodies used for immunofluorescence.

| Antigen | Species | Dilution | Vendor |
|---|---|---|---|
| α-SMA | Mouse | 100 | SIGMA-ALDRICH |
| MUC2 | Rabbit | 500 | Abcam |
| UROCORTIN 3 | Rabbit | 300 | SIGMA-ALDRICH |
| GHRELIN | Goat | 300 | Ask Lisa |
| GLUT2 | Goat | 200 | Millipore |
| SUR1 | Goat | 100 | Santa Cruz |
| PC1 | Rabbit | 500 | Millipore |
| SEROTONIN | Mouse | 100 | Novus Biologicals |
| LYSOZYME | Rabbit | 100 | Abcam |
| VILLIN | Mouse | 100 | Millipore |
| CHROMOGRANIN A | Mouse | 100 | Millipore |
| CHROMOGRANIN A | Rabbit | 400 | LSBio |
| CDX2 | Mouse | 200 | Biogenex |
| CDX2 | Rabbit | 500 | Abcam |
| CCK | Rabbit | 100 | Aviva System Biology |
| DCAMKL1 | Rabbit | 50 | LSBio |
| GLP1 | Mouse | 100 | Novus Biologicals |
| SECRETIN | Rabbit | 100 | LSBio |
| GASTRIN | Rabbit | 500 | LSBio |
| HA | Mouse | 200 | Abcam |
| PCSK2 | Rabbit | 200 | R&D system |
| PCSK2 | Rabbit | 100 | Millipore |
| C-PEPTIDE | Mouse | 1000 | Millipore |
| NKX6.1 | Mouse | 300 | DSHB |
| FOXO1 | Rabbit | 50 | Cell Signaling |
| FOXO1 | Goat | 50 | LSBio |
| GIP | Mouse | 50 | Abcam |
| SOMATOSTATIN | Rabbit | 100 | Novus Biologicals |
| SOMATOSTATIN | Rabbit | 25 | DAKO |
| INSULIN | Guinea pig | 2000 | DAKO |
| MAF A | Rabbit | 50 | Abcam |
| MAF B | Rabbit | 50 | SIGMA-ALDRICH |
| GLUCOKINASE | Rabbit | 100 | Santa Cruz |
| OLFM4 | Rabbit | 100 | LS Bio |

SUPPLEMENTARY TABLE 2
Primer sequences used for qRT-PCR.

| Gene | Forward | Seq ID No. | Reverse | Seq ID No. |
|---|---|---|---|---|
| INSULIN | CCAGCTGGTAGAGGGAGCAGAT | 7 | TACCTAGTGTGCGGGGAACGAG | 8 |
| NEUROGENIN3 | TACATCTGGGCGCTGACTCAAA | 9 | AGCCTGGGAGACTGGGGAGTAG | 10 |
| CHROMOGRANIN A | GCTCCCTGTGAACAGCCCTATG | 11 | CGAGGTCTTGGAGCTCCTTCAG | 12 |
| FOXO1 | GATGGTCAAGAGCGTGCCCTAC | 13 | TGGATTGAGCATCCACCAAGAA | 14 |
| FOXO3 | TTGCGTGCCCTACTTCAAGGAT | 15 | AGAGCTCTTGCCAGTTCCCTCA | 16 |

SUPPLEMENTARY TABLE 2
Primer sequences used for qRT-PCR.

| Gene | Forward | Seq ID No. | Reverse | Seq ID No. |
|---|---|---|---|---|
| FOXO4 | TCAAGGACAAGGGTGACAGCAA | 17 | AGGGTTCAGCATCCACCAAGAG | 18 |
| VILLIN | CAGTACCCACCAAGCACACAGG | 19 | ATGGATGTGGCATCGAACTTCA | 20 |
| LYSOZYME | TGGCTACAGGGGAATCAGCCTA | 21 | TTAACTGCTCCTGGGGTTTTGC | 22 |
| MUC2 | GTGGAGTCCAGCACGGGCAT | 23 | TCACCACCATGTGGTCCCGC | 24 |
| CDX2 | ATCGAGTGGTGTACACGGACCA | 25 | CTCTCCTTTGCTCTGCGGTTCT | 26 |
| PC1 | ATAATCACAAATGCGGGGTTGG | 27 | ATCATCATTAGGGCCCCAGCTT | 28 |
| PC2 | TTGCATAAAGGGGGAGAGGAGA | 29 | CTTCCTGCTGCAAAGCCATCTT | 30 |
| GLUT2 | TGGGATGTTTGTTTGTGCCATC | 31 | CAGGACGTGGTCCTTGACTGAA | 32 |
| GCK | TGAGTGCATCTCCGACTTCCTG | 33 | CGTTTGATAGCGTCTCGCAGAA | 34 |
| KIR6.2 | TTGATGCCAACAGCCCACTCTA | 35 | TCCTCAGCTACAATGGGCACAA | 36 |
| SUR1 | AGTGGCCACACACATTGCTCAT | 37 | GAAGGAGTGGATGCTGGTGACA | 38 |
| PAX6 | ACTCTGCGCTTGGCCAAGAACT | 39 | GGGCTGAGGGGTCCATCAAAGG | 40 |
| PAX4 | GGGCTGACTGTACCAAGGGTTG | 41 | GCAGGGCTTGAGACAGGCTTTA | 42 |
| NKX2.2 | TTCTACGACAGCAGCGACAACC | 43 | TTGTCATTGTCCGGTGACTCGT | 44 |
| NKX6.1 | GCCTATTCGTTGGGGATGACAG | 45 | CGAGTTGGGATCCAGAGGCTTA | 46 |
| ARX | GAAACGCAAACAGAGGCGCTAC | 47 | GGTTCTGGAACCAGACCTGGAC | 48 |
| NEUROD1 | AAGAGACGCGGCCCCAAAAAGA | 49 | TCTTGGCCAAGCGCAGAGTCTC | 50 |
| MAFA | TCCTTGTACAGGTCCCGCTCTT | 51 | CAGTGCCAACTCGCTCTTAGGC | 52 |
| MAFB | GTTGCTCGCCATCCAGTACAGA | 53 | TGGATTGAGCATCCACCAAGAA | 54 |
| PDX1 | CTGCCTTTCCCATGGATGAAGT | 55 | CGGCCGTGAGATGTACTTGTTG | 56 |
| ISLET1 | AGCAGCAGCCCAATGACAAAAC | 57 | CAGTTGCTGAAAAGCAGGCTGA | 58 |
| RFX6 | ATCAGCAGCATTCGTTCACTGC | 59 | GGAAGAAGGAATTGGGGTTTGC | 60 |
| SLC30A-8 | GAGCGCCTGCTGTATCCTGATT | 61 | ATGCACAAAAGCAGCTCTGACG | 62 |
| UROCORTIN3 | AGGCCTCCCCCACAAGTTCTAC | 63 | TTCTCTTTGCCCTCCTCCTCCT | 64 |
| LGR5 | TTCCTCAAACCGTCTGCAATCA | 65 | GGAGGCTAAGCAACTGCTGGAA | 66 |
| OLFM4 | TGGCTCTGAAGACCAAGCTGAA | 67 | GTAATCCCTACCCCAAGCACCA | 68 |
| BMI1 | TGCTGCCAATGGCTCTAATGAA | 69 | TTGCTGCTGGGCATCGTAAGTA | 70 |
| MATH1 | AATGGGGTGCAGAAGCAGAGAC | 71 | TCGGACAAGGCGTTGATGTAGA | 72 |
| SUBSTANCE P | TACGACAGCGACCAGATCAAGG | 73 | GAGCCTTTAACAGGGCCACTTG | 74 |
| GHRL | AAAGGAGTCGAAGAAGCCACCA | 75 | TGCTGGTACTGAACCCCTGACA | 76 |
| PPY | CCACCTGCGTGGCTCTGTTACT | 77 | CCAGCGTGTCCTCTTTGTGTCT | 78 |
| GLUCAGON | AGGCAGACCCACTCAGTGATCC | 79 | CATCGTGACGTTTGGCAATGTT | 80 |
| 5HT | CACCCACCCTAGTGGCTGAGCTT | 81 | CCATGATGGTGTAGGGGAGGAG | 82 |
| SECRETIN | AGCAGGACGCAGAGAACAGCAT | 83 | GCCAGCTGGTTCTGAAACCATA | 84 |
| CCK | AGGGTATCGCAGAGAACGGATG | 85 | GTCCCGGTCACTTATCCTGTGG | 86 |
| GASTRIN | ACCCTTAGGTACAGGGGCCAAC | 87 | GCCGAAGTCCATCCATCCATAG | 88 |
| GIP | GCCCAAAAGGGGAAGAAGAATG | 89 | GCCAACAGCTCTTGAATCAGCA | 90 |

SUPPLEMENTARY TABLE 2
Primer sequences used for qRT-PCR.

| Gene | Forward | Seq ID No. | Reverse | Seq ID No. |
|---|---|---|---|---|
| SOMATOSTATIN | GACCCCAGACTCCGTCAGTTTC | 91 | CTGCAGCTCAAGCCTCATTTCA | 92 |
| HES1 | CAACACGACACCGGATAAACCA | 93 | CATTTCCAGAATGTCCGCCTTC | 94 |
| HESR1 | CCGACGAGACCGGATCAATAAC | 95 | CTGCCGTATGCAGCATTTTCAG | 96 |
| HEYL | AAGCTGGAGAAAGCCGAGGTCT | 97 | AAACCAATGCTCCGGAAGTCAA | 98 |
| AES | GCCTCAAGCTCGAATGTGACAA | 99 | TGGTGCTCTTGGGAGAGGTAGG | 100 |
| HPRT | AATGACCAGTCAACAGGGGACA | 101 | CACTTCGTGGGGTCCTTTTCAC | 102 |

SUPPLEMENTARY TABLE 3 mRNA expression in human gut organoids during differentiation.

| | Day 0 | | Day 4 | | Day 8 | |
|---|---|---|---|---|---|---|
| Gene | Mean | SE | Mean | SE | Mean | SE |
| Foxo1 | 1.557417 | 0.120279 | 3.598765 | 0.653531 | 2.545899 | 0.079206 |
| Foxo3 | 2.252112 | 0.478212 | 0.561494 | 0.066739 | 1.093899 | 0.053874 |
| Foxo4 | 0.513709 | 0.058905 | 0.714333 | 0.061331 | 0.463877 | 0.052408 |
| Villin | 0.129686 | 0.009888 | 0.458574 | 0.054688 | 0.375812 | 0.033531 |
| Lysozyme | 0.001354 | 0.000746 | 0.001410 | 0.000792 | 0.018025 | 0.006163 |
| MUC2 | 0.000081 | 0.000036 | 0.000278 | 0.0000749 | 0.000809 | 0.000226 |
| Insulin | 0.000072 | 0.000058 | 0.000173 | 0.000084 | 0.0000440 | 0.0000024 |
| Neurog3 | 0.000243 | 0.0000301 | 0.000387 | 0.00004 | 0.0047696 | 0.0039879 |
| CgA | 1.580648 | 0.224190 | 0.175635 | 0.019760 | 0.125747 | 0.014755 |
| SLC6A4 | 0.003077 | 0.00134 | 0.037453 | 0.004358 | 0.025013 | 0.002054 |
| Glucagon | ND | ND | ND | ND | ND | ND |
| GIP | ND | ND | ND | ND | ND | ND |
| CCK | 0.016199 | 0.000109 | 0.00704 | 0.003496 | 0.017282 | 0.003594 |
| Gastrin | 0.149596 | 0.029731 | 0.239073 | 0.022239 | 0.447024 | 0.06250 |
| Ghrelin | 0.001631 | 0.000453 | 0.001623 | 0.00136 | 0.00237 | 0.000989 |
| Somatostatin | 0.011641 | 0.0001307 | 0.021783 | 0.000465 | 0.019725 | 0.002345 |

| | Day 22 | | Day 36 | | Day 184 | |
|---|---|---|---|---|---|---|
| Gene | Mean | SE | Mean | SE | Mean | SE |
| Foxo1 | 1.288813 | 0.108885 | 1.414794 | 0.191918 | 0.876028 | 0.165403 |
| Foxo3 | 1.942102 | 0.168681 | 4.019815 | 0.487795 | 4.192344 | 0.627453 |
| Foxo4 | 1.525665 | 0.256800 | 1.623709 | 0.028419 | 1.359027 | 0.270383 |
| Villin | 5.384168 | 0.761846 | 10.06858 | 1.851017 | 48.59651 | 6.159125 |
| Lysozyme | 4.725360 | 0.335488 | 42.31775 | 24.02228 | 163.4495 | 40.47131 |
| MUC2 | 0.044237 | 0.022287 | 0.024735 | 0.006228 | 6.376352 | 1.200474 |
| Insulin | 0.000165 | 0.000098 | 0.001368 | 0.000365 | 0.002680 | 0.002205 |
| Neurog3 | 0.004023 | 0.000729 | 0.005489 | 0.002548 | 0.010548 | 0.001948 |
| CgA | 0.882200 | 0.165648 | 14.01394 | 3.114811 | 82.93569 | 31.81144 |
| SLC6A4 | 0.167478 | 0.035988 | 0.421448 | 0.084309 | 0.464832 | 0.074382 |
| Glucagon | 0.110178 | 0.032389 | 1.984532 | 0.705088 | 53.51102 | 21.04996 |
| GIP | ND | ND | 0.011618 | 0.000798 | 0.028677 | 0.011618 |
| CCK | 0.008903 | 0.001499 | 0.077003 | 0.011052 | 0.049494 | 0.000391 |
| Gastrin | 1.524565 | 0.534751 | 2.783928 | 1.221507 | 1.006138 | 0.409483 |
| Ghrelin | 0.026196 | 0.016926 | 1.881976 | 0.671368 | 3.091087 | 0.839246 |
| Somatostatin | 13.5029 | 1.220281 | 30.53252 | 5.939474 | 31.15832 | 14.22948 |

SUPPLEMENTARY TABLE 4 mRNA expression in gut organoids transduced with control and HA-Δ256 FOXO1 adenovirus.

|  | Control | | Δ256 | | |
|---|---|---|---|---|---|
|  | Mean | SE | Mean | SE | p |
| Foxo1 | 0.846555 | 0.113497 | 4.009534 | 0.556462 | <0.05 |
| Foxo3 | 4.331418 | 0.359165 | 4.762217 | 1.308275 | NS |
| Foxo4 | 0.763258 | 0.042208 | 0.830801 | 0.230761 | NS |
| Insulin | 0.019516 | 0.003898 | 0.14454 | 0.000657 | <0.05 |
| Neurog3 | 0.045927 | 0.005656 | 0.260422 | 0.030423 | <0.05 |
| CgA | 13.67444 | 0.937486 | 21.14381 | 1.333514 | <0.05 |
| CDX2 | 12.43775 | 1.582346 | 16.63944 | 2.905261 | NS |
| Villin | 28.19776 | 4.682933 | 18.91874 | 6.064737 | NS |
| Lysozyme | 158.555 | 24.60191 | 136.2488 | 53.2402 | NS |
| Muc2 | 8.617466 | 2.031311 | 14.49713 | 6.156312 | NS |
| LGR5 | 1.658112 | 0.440981 | 1.650161 | 0.445046 | NS |
| Olfm4 | 85.21344 | 51.92498 | 76.29359 | 2.089699 | NS |
| Bim1 | 1.520503 | 0.149423 | 2.203499 | 0.116843 | NS |
| Math1 | 0.897732 | 0.261626 | 3.091502 | 1.093768 | NS |
| Hes1 | 13.4084 | 1.108315 | 13.91184 | 1.589168 | NS |
| HesR1 | 0.71732 | 0.105136 | 2.090294 | 0.723214 | NS |
| HeyL | 0.136213 | 0.064531 | 0.220304 | 0.075566 | NS |
| AES | 42.07569 | 14.94373 | 61.0454 | 11.41413 | NS |
| PDX1 | 0.569858 | 0.144733 | 0.898912 | 0.106247 | NS |
| Nkx2.2 | 0.001288 | 0.000205 | 0.002451 | 0.000453 | <0.05 |
| Nkx6.1 | 0.018393 | 0.005162 | 0.142881 | 0.052814 | <0.05 |
| NeuroD1 | 0.024278 | 0.014222 | 0.182801 | 0.00275 | <0.05 |
| Pax4 | 0.684699 | 0.139704 | 2.24176 | 0.020548 | <0.05 |
| Pax6 | 4.059091 | 1.956735 | 0.953035 | 2.842897 | <0.05 |
| MafA | 0.054917 | 0.017666 | 0.382146 | 0.064296 | <0.05 |
| MafB | 0.14707 | 0.031138 | 0.927882 | 0.189238 | <0.05 |
| Isl-1 | 0.211731 | 0.062167 | 0.385543 | 0.071277 | NS |
| Rfx6 | 0.107037 | 0.003212 | 0.42365 | 0.139787 | <0.05 |
| Arx | 0.013988 | 0.003166 | 0.058559 | 0.020689 | NS |
| SLC30A8 | 0.000076 | 0.000021 | 0.317700 | 0.205205 | <0.05 |
| UCN3 | 0.6474766 | 0.0753344 | 2.8092592 | 0.218692 | <0.05 |
| Kir6.2 | 0.2537708 | 0.069613 | 1.8531898 | 0.667138 | NS |
| Sur1 | 0.2713117 | 0.119167 | 0.4261289 | 0.071866 | NS |
| Glut2 | 0.2779970 | 0.0527430 | 0.4574555 | 0.086376 | NS |
| PC2 | 0.9606606 | 0.0100187 | 1.4714312 | 0.293444 | NS |
| Gck | 0.0449448 | 0.0058264 | 0.0778999 | 0.011639 | NS |
| PC1/3 | 3.8472895 | 2.1020310 | 3.9721181 | 0.879261 | NS |

What is claimed is:

1. A method comprising administering to a mammal having a disease or disorder associated with impaired pancreatic endocrine function, a therapeutically effective amount of an agent selected from the group consisting of isolated small hairpin RNA (shRNA), small interfering RNA (siRNA), antisense RNA, antisense DNA, chimeric antisense DNA/RNA, and ribozymes that is sufficiently complementary to specifically bind to a gene or mRNA encoding Foxo1 protein thereby reducing the expression, biosynthesis, signaling or biological activity of Foxo1, wherein administering comprises delivering the agent to insulin-negative, serotonin-positive enteroendocrine cells in the gut (Gut-Ins– cells) thereby producing insulin-positive cells that make and secrete biologically active insulin (Gut Ins+ cells) thereby treating the disease or disorder, and wherein the agent is targeted to serotonin-positive enteroendocrine cells.

2. The method of claim 1, wherein the insulin-positive cells are glucose-responsive cells.

3. The method of claim 1, wherein the agent is orally administered in an enteric form that releases the therapeutically effective amount in a region of the gut comprising insulin-negative, serotonin-positive enteroendocrine cells or is locally administered directly into or onto the gut region.

4. The method of claim 2, wherein the gut region is the duodenum, ileum or colon.

5. The method of claim 1, wherein the disease or disorder is selected from the group consisting of diabetes type 1, diabetes type 2, metabolic syndrome, glucose intolerance, hyperglycemia, decreased insulin sensitivity, increased fasting glucose, increased post-prandial glucose and obesity.

6. The method of claim 1, wherein the therapeutically effective amount is an amount that produces an effect selected from the group consisting of an increase in glucose tolerance, an increase in serum insulin, an increase insulin sensitivity, a decrease in fasting glucose, a decrease in post-prandial glucose, a decrease in weight gain, a decrease in fat mass, an increase in weight loss and the generation enteroendocrine cells in the gastrointestinal tract that produce and secrete insulin.

7. The method of claim 1, wherein the agent is administered orally, or parenterally or as a suppository.

8. A method for producing cells in the gut of a mammal that make and secrete biologically active insulin (Gut Ins+ cells), comprising administering to the mammal an agent selected from the group consisting of isolated small hairpin ins RNA (shRNA), small interfering RNA (siRNA), antisense RNA, antisense DNA, chimeric antisense DNA/RNA, and ribozymes that is sufficiently complementary to specifically bind to a gene or mRNA encoding Foxo1 protein thereby reducing the expression, biosynthesis, signaling or biological activity of Foxo1, wherein administering comprises delivering the agent to insulin-negative cells in the gut (Gut-Ins– cells) comprising serotonin-positive, insulin-negative enteroendocrine cells thereby producing gut cells that make and secrete biologically active insulin (Gut Ins+ cells), wherein the agent is targeted to serotonin-positive enteroendocrine cells.

9. The method of claim 8, wherein the gut+cells are glucose responsive.

* * * * *